(12) United States Patent
Pushko et al.

(10) Patent No.: US 9,968,672 B2
(45) Date of Patent: *May 15, 2018

(54) IDNA VACCINES AND METHODS FOR USING THE SAME

(71) Applicant: Medigen, Inc., Frederick, MD (US)

(72) Inventors: Peter Pushko, Frederick, MD (US); Igor Lukashevich, Cockeysville, MD (US)

(73) Assignee: MEDIGEN, INC., Frederick, MD (US)

( * ) Notice: Subject to any disclaimer, the term of this patent is extended or adjusted under 35 U.S.C. 154(b) by 55 days.

This patent is subject to a terminal disclaimer.

(21) Appl. No.: 14/168,788

(22) Filed: Jan. 30, 2014

(65) Prior Publication Data

US 2014/0178430 A1    Jun. 26, 2014

Related U.S. Application Data

(63) Continuation of application No. 13/054,372, filed as application No. PCT/US2009/004133 on Jul. 17, 2009, now Pat. No. 8,691,563.

(60) Provisional application No. 61/081,482, filed on Jul. 17, 2008.

(51) Int. Cl.
| | |
|---|---|
| *A61K 39/12* | (2006.01) |
| *C12N 7/00* | (2006.01) |
| *A61K 39/193* | (2006.01) |
| *C12N 15/85* | (2006.01) |
| *A61K 39/00* | (2006.01) |

(52) U.S. Cl.
CPC ............ *A61K 39/193* (2013.01); *A61K 39/12* (2013.01); *C12N 7/00* (2013.01); *C12N 15/85* (2013.01); *A61K 2039/53* (2013.01); *C12N 2770/24134* (2013.01); *C12N 2770/24161* (2013.01); *C12N 2770/36134* (2013.01); *C12N 2770/36161* (2013.01)

(58) Field of Classification Search
None
See application file for complete search history.

(56) References Cited

U.S. PATENT DOCUMENTS

| | | | |
|---|---|---|---|
| 6,171,854 B1 * | 1/2001 | Galler ................... | C07K 14/005 435/320.1 |
| 6,511,838 B1 | 1/2003 | Flament et al. | |
| 6,565,853 B1 | 5/2003 | Jacobs | |
| 8,691,563 B2 * | 4/2014 | Pushko ................ | A61K 39/12 424/218.1 |
| 9,101,572 B2 * | 8/2015 | Pushko ................ | A61K 39/12 |
| 2005/0276816 A1 | 12/2005 | Yamshchikov | |
| 2006/0159704 A1 | 7/2006 | Bonaldo et al. | |
| 2006/0198854 A1 | 9/2006 | Pushko | |
| 2006/0280757 A1 | 12/2006 | Khromykh | |

FOREIGN PATENT DOCUMENTS

WO    02/099035 A2    12/2002

OTHER PUBLICATIONS

Troy Querec et al., Journal of Experimental Medicine, Feb. 20, 2006, 203(2):413-424.
Extended European Search Report dated Dec. 22, 2011 by the European Patent Office in corresponding European Patent Application No. 09798313.4.
International Search Report corresponding to PCT/US 2009/004133 dated Mar. 2, 2010.
Anishchenko et al., Journal of Virology, Jan. 2004, 78(1):1-8.
Pu et al., Journal of Virology, Mar. 2011, 85(6):2927-2941.
Rice et al., New Biol., Dec. 1989, 1(3):285-96.
Partial European Search Report dated Dec. 14, 2015 corresponding to European Patent Application No. 15166439.8, 8 pages.
Extended European Search Report dated Apr. 4, 2016 corresponding to European Patent Application No. 15166439.8, 11 pages.
Kinney, R.M., et al., "Attenuation of Venezuelan Equine Encephalitis Virus Strain TC-83 Is Encoded by the 5'-Noncoding Region and the E2 Envelope Glycoprotein," Journal of Virology, vol. 67, No. 3, Mar. 1993, pp. 1269-1277.

* cited by examiner

*Primary Examiner* — Stacy B Chen

(74) *Attorney, Agent, or Firm* — Dentons US LLP

(57) ABSTRACT

Described herein are iDNA vectors and vaccines and methods for using the same. The iDNA generates live attenuated vaccines in eukaryotic cells in vitro or in vivo for pathogenic RNA viruses, particularly yellow fever virus and Venezuelan equine encephalitis virus. When iDNA is injected into the vaccine recipient, RNA of live attenuated virus is generated by in vivo transcription in the recipient's tissues. This initiates production of progeny attenuated viruses in the tissues of the vaccine recipient, as well as elicitation of an effective immune response protecting against wild-type, non-attenuated virus.

32 Claims, 31 Drawing Sheets

FIG. 1: TC-83 IDNAs FOR VACCINE PRODUCTION *IN VITRO* OR VACCINATION *IN VIVO*

FIG. 2: VEE VACCINE PRODUCTION *IN VITRO* OR *IN VIVO* FROM THE CMV-TC83 iDNA

FIG. 3: YELLOW FEVER VIRUS iDNA FOR VACCINE PRODUCTION *IN VITRO* OR VACCINATION *IN VIVO*

FIG. 4: YELLOW FEVER VACCINE PRODUCTION *IN VITRO* OR *IN VIVO* FROM THE CMV-YF17D iDNA

FIG. 5: IMMUNOFLUORESCENCE ASSAY
(A)
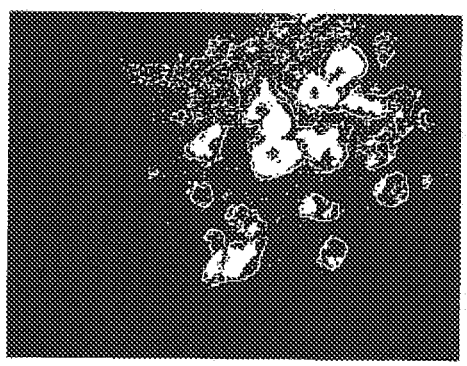
(B)
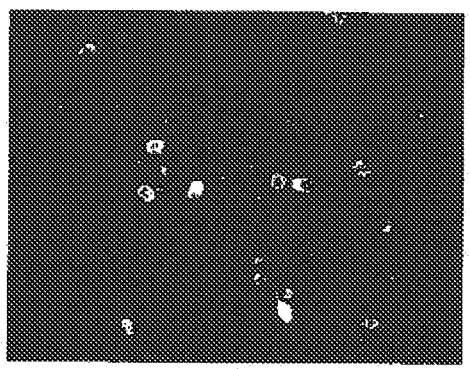

FIG. 6: iDNA SEQUENCE FRAGMENT FROM pAA_TC83 PLASMID

```
   1  ACAAGGCAAG GCTTGACCGA CAATTGCATG AAGAATCTGC TTAGGGTTAG
                                                      ↓AscI
  51  GCGTTTTGCG CTGCTTCGCG ATGTACGGGC CAGATATACG CGTGGCGCGC
                           ↓CMV promoter start
 101  CTGACATTGA TTATTGACTA GTTATTAATA GTAATCAATT ACGGGGTCAT

151  TAGTTCATAG CCCATATATG GAGTTCCGCG TTACATAACT TACGGTAAAT

201  GGCCCGCCTG GCTGACCGCC CAACGACCCC CGCCCATTGA CGTCAATAAT

251  GACGTATGTT CCCATAGTAA CGCCAATAGG GACTTTCCAT TGACGTCAAT

301  GGGTGGAGTA TTTACGGTAA ACTGCCCACT TGGCAGTACA TCAAGTGTAT

351  CATATGCCAA GTACGCCCCC TATTGACGTC AATGACGGTA AATGGCCCGC

401  CTGGCATTAT GCCCAGTACA TGACCTTATG GGACTTTCCT ACTTGGCAGT

451  ACATCTACGT ATTAGTCATC GCTATTACCA TGGTGATGCG GTTTTGGCAG

501  TACATCAATG GGCGTGGATA GCGGTTTGAC TCACGGGGAT TTCCAAGTCT

551  CCACCCCATT GACGTCAATG GGAGTTTGTT TTGGCACCAA AATCAACGGG

601  ACTTTCCAAA ATGTCGTAAC AACTCCGCCC CATTGACGCA AATGGGCGGT
                            CMV promoter end ↓
 651  AGGCGTGTAC GGTGGGAGGT CTATATAAGC AGAGCTCTCT GGCTAACTAG
        ↓ TC-83 iDNA start
 701  AGATAGGCGG CGCATGAGAG AAGCCCAGAC CAATTACCTA CCCAAAATGG

751  AGAAAGTTCA CGTTGACATC GAGGAAGACA GCCCATTCCT CAGAGCTTTG

801  CAGCGGAGCT TCCCGCAGTT TGAGGTAGAA GCCAAGCAGG TCACTGATAA

851  TGACCATGCT AATGCCAGAG CGTTTTCGCA TCTGGCTTCA AAACTGATCG

901  AAACGGAGGT GGACCCATCC GACACGATCC TTGACATTGG AAGTGCGCCC

951  GCCCGCAGAA TGTATTCTAA GCACAAGTAT CATTGTATCT GTCCGATGAG

1001  ATGTGCGGAA GATCCGGACA GATTGTATAA GTATGCAACT AAGCTGAAGA

1051  AAAACTGTAA GGAAATAACT GATAAGGAAT TGGACAAGAA AATGAAGGAG

1101  CTCGCCGCCG TCATGAGCGA CCCTGACCTG GAAACTGAGA CTATGTGCCT

1151  CCACGACGAC GAGTCGTGTC GCTACGAAGG GCAAGTCGCT GTTTACCAGG

1201  ATGTATACGC GGTTGACGGA CCGACAAGTC TCTATCACCA AGCCAATAAG

1251  GGAGTTAGAG TCGCCTACTG GATAGGCTTT GACACCACCC CTTTTATGTT

1301  TAAGAACTTG GCTGGAGCAT ATCCATCATA CTCTACCAAC TGGGCCGACG

1351  AAACCGTGTT AACGGCTCGT AACATAGGCC TATGCAGCTC TGACGTTATG

1401  GAGCGGTCAC GTAGAGGGAT GTCCATTCTT AGAAAGAAGT ATTTGAAACC

1451  ATCCAACAAT GTTCTATTCT CTGTTGGCTC GACCATCTAC CACGAGAAGA

1501  GGGACTTACT GAGGAGCTGG CACCTGCCGT CTGTATTTCA CTTACGTGGC

1551  AAGCAAAATT ACACATGTCG GTGTGAGACT ATAGTTAGTT GCGACGGGTA

1601  CGTCGTTAAA AGAATAGCTA TCAGTCCAGG CCTGTATGGG AAGCCTTCAG

1651  GCTATGCTGC TACGATGCAC CGCGAGGGAT TCTTGTGCTG CAAAGTGACA

1701  GACACATTGA ACGGGGAGAG GGTCTCTTTT CCCGTGTGCA CGTATGTGCC

1751  AGCTACATTG TGTGACCAAA TGACTGGCAT ACTGGCAACA GATGTCAGTG
```

Fig. 6 Cont.

```
1801  CGGACGACGC GCAAAACTG CTGGTTGGGC TCAACCAGCG TATAGTCGTC
1851  AACGGTCGCA CCCAGAGAAA CACCAATACC ATGAAAAATT ACCTTTTGCC
1901  CGTAGTGGCC CAGGCATTTG CTAGGTGGGC AAAGAATAT AAGGAAGATC
1951  AAGAAGATGA AAGGCCACTA GGACTACGAG ATAGACAGTT AGTCATGGGG
2001  TGTTGTTGGG CTTTTAGAAG GCACAAGATA ACATCTATTT ATAAGCGCCC
2051  GGATACCCAA ACCATCATCA AAGTGAACAG CGATTTCCAC TCATTCGTGC
2101  TGCCCAGGAT AGGCAGTAAC ACATTGGAGA TCGGGCTGAG AACAAGAATC
2151  AGGAAAATGT TAGAGGAGCA CAAGGAGCCG TCACCTCTCA TTACCGCCGA
2201  GGACGTACAA GAAGCTAAGT GCGCAGCCGA TGAGGCTAAG GAGGTGCGTG
2251  AAGCCGAGGA GTTGCGCGCA GCTCTACCAC CTTTGGCAGC TGATGTGAG
2301  GAGCCCACTC TGGAAGCCGA TGTCGACTTG ATGTTACAAG AGGCTGGGGC
2351  CGGCTCAGTG GAGACACCTC GTGGCTTGAT AAAGGTTACC AGCTACGCTG
2401  GCGAGGACAA GATCGGCTCT TACGCTGTGC TTTCTCCGCA GGCTGTACTC
2451  AAGAGTGAAA AATTATCTTG CATCCACCCT CTCGCTGAAC AAGTCATAGT
2501  GATAACACAC TCTGGCCGAA AAGGGCGTTA TGCCGTGGAA CCATACCATG
2551  GTAAAGTAGT GGTGCCAGAG GGACATGCAA TACCCGTCCA GGACTTTCAA
2601  GCTCTGAGTG AAAGTGCCAC CATTGTGTAC AACGAACGTG AGTTCGTAAA
2651  CAGGTACCTG CACCATATTG CCACACATGG AGGAGCGCTG AACACTGATG
2701  AAGAATATTA CAAAACTGTC AAGCCCAGCG AGCACGACGG CGAATACCTG
2751  TACGACATCG ACAGGAAACA GTGCGTCAAG AAAGAACTAG TCACTGGGCT
2801  AGGGCTCACA GGCGAGCTGG TGGATCCTCC CTTCCATGAA TTCGCCTACG
2851  AGAGTCTGAG AACACGACCA GCCGCTCCTT ACCAAGTACC AACCATAGGG
2901  GTGTATGGCG TGCCAGGATC AGGCAAGTCT GGCATCATTA AAAGCGCAGT
2951  CACCAAAAAA GATCTAGTGG TGAGCGCCAA GAAAGAAAAC TGTGCAGAAA
3001  TTATAAGGGA CGTCAAGAAA ATGAAAGGGC TGGACGTCAA TGCCAGAACT
3051  GTGGACTCAG TGCTCTTGAA TGGATGCAAA CACCCCGTAG AGACCCTGTA
3101  TATTGACGAA GCTTTTGCTT GTCATGCAGG TACTCTCAGA GCGCTCATAG
3151  CCATTATAAG ACCTAAAAAG GCAGTGCTCT GCGGGGATCC CAAACAGTGC
3201  GGTTTTTTTA ACATGATGTG CCTGAAAGTG CATTTAACC ACGAGATTTG
3251  CACACAAGTC TTCCACAAAA GCATCTCTCG CCGTTGCACT AAATCTGTGA
3301  CTTCGGTCGT CTCAACCTTG TTTTACGACA AAAAAATGAG AACGACGAAT
3351  CCGAAAGAGA CTAAGATTGT GATTGACACT ACCGGCAGTA CCAAACCTAA
3401  GCAGGACGAT CTCATTCTCA CTTGTTTCAG AGGGTGGGTG AAGCAGTTGC
3451  AAATAGATTA CAAAGGCAAC GAAATAATGA CGGCAGCTGC CTCTCAAGGG
3501  CTGACCCGTA AAGGTGTGTA TGCCGTTCGG TACAAGGTGA ATGAAAATCC
3551  TCTGTACGCA CCCACCTCAG AACATGTGAA CGTCCTACTG ACCCGCACGG
3601  AGGACCGCAT CGTGTGGAAA ACACTAGCCG GCGACCCATG GATAAAAACA
3651  CTGACTGCCA AGTACCCTGG GAATTTCACT GCCACGATAG AGGAGTGGCA
```

Fig. 6 Cont.

```
3701  AGCAGAGCAT GATGCCATCA TGAGGCACAT CTTGGAGAGA CCGGACCCTA
3751  CCGACGTCTT CCAGAATAAG GCAAACGTGT GTTGGGCCAA CGCTTTAGTG
3801  CCGGTGCTGA AGACCGCTGG CATAGACATG ACCACTGAAC AATGGAACAC
3851  TGTGGATTAT TTTGAAACGG ACAAAGCTCA CTCAGCAGAA TAGTATTGA
3901  ACCAACTATG CGTCAGGTTC TTTGGACTCG ATCTGGACTC CGGTCTATTT
3951  TCTGCACCCA CTGTTCCGTT ATCCATTAGG AATAATCACT GGGATAACTC
4001  CCGGTCGCCT AACATGTACG GGCTGAATAA AGAAGTGGTC CGTCAGCTCT
4051  CTCGCAGGTA CCCACAACTG CCTCGGGCAG TTGCCACTGG AAGAGTCTAT
4101  GACATGAACA CTGGTACACT GCGCAATTAT GATCCGCGCA TAAACCTAGT
4151  ACCTGTAAAC AGAAGACTGC CTCATGCTTT AGTCCTCCAC CATAATGAAC
4201  ACCCACAGAG TGACTTTTCT TCATTCGTCA GCAAATTGAA GGGCAGAACT
4251  GTCCTGGTGG TCGGGGAAAA GTTGTCCGTC CCAGGCAAAA TGGTTGACTG
4301  GTTGTCAGAC CGGCCTGAGG CTACCTTCAG AGCTCGGCTG GATTTAGGCA
4351  TCCCAGGTGA TGTGCCCAAA TATGACATAA TATTTGTTAA TGTGAGGACC
4401  CCATATAAAT ACCATCACTA TCAGCAGTGT GAAGACCATG CCATTAAGCT
4451  TAGCATGTTG ACCAAGAAAG CTTGTCTGCA TCTGAATCCC GGCGGAACCT
4501  GTGTCAGCAT AGGTTATGGT TACGCTGACA GGGCCAGCGA AAGCATCATT
4551  GGTGCTATAG CGCGGCAGTT CAAGTTTTCC CGGGTATGCA AACCGAAATC
4601  CTCACTTGAA GAGACGGAAG TTCTGTTTGT ATTCATTGGG TACGATCGCA
4651  AGGCCCGTAC GCACAATCCT TACAAGCTTT CATCAACCTT GACCAACATT
4701  TATACAGGTT CCAGACTCCA CGAAGCCGGA TGTGCACCCT CATATCATGT
4751  GGTGCGAGGG GATATTGCCA CGGCCACCGA AGGAGTCATT ATAAATGCTG
4801  CTAACAGCAA AGGACAACCT GGCGGAGGGG TGTGCGGAGC GCTGTATAAG
4851  AAGTTCCCGG AAAGCTTCGA TTTACAGCCG ATCGAAGTAG GAAAAGCGCG
4901  ACTGGTCAAA GGTGCAGCTA AACATATCAT TCATGCCGTA GGACCAAACT
4951  TCAACAAAGT TTCGGAGGTT GAAGGTGACA AACAGTTGGC AGAGGCTTAT
5001  GAGTCCATCG CTAAGATTGT CAACGATAAC AATTACAAGT CAGTAGCGAT
5051  TCCACTGTTG TCCACCGGCA TCTTTTCCGG GAACAAAGAT CGACTAACCC
5101  AATCATTGAA CCATTTGCTG ACAGCTTTAG ACACCACTGA TGCAGATGTA
5151  GCCATATACT GCAGGGACAA GAAATGGGAA ATGACTCTCA AGGAAGCAGT
5201  GGCTAGGAGA GAAGCAGTGG AGGAGATATG CATATCCGAC GACTCTTCAG
5251  TGACAGAACC TGATGCAGAG CTGGTGAGGG TGCATCCGAA GAGTTCTTTG
5301  GCTGGAAGGA AGGGCTACAG CACAAGCGAT GGCAAAACTT TCTCATATTT
5351  GGAACGGACC AAGTTTCACC AGGCGGCCAA GGATATAGCA CAAATTAATG
5401  CCATGTGGCC CGTTGCAACG GAGGCCAATG AGCAGGTATG CATGTATATC
5451  CTCGGAGAAA GCATGAGCAG TATTAGGTCG AAATGCCCCG TCGAAGAGTC
5501  GGAAGCCTCC ACACCACCTA GCACGCTGCC TTGCTTGTGC ATCCATGCCA
5551  TGACTCCAGA AAGAGTACAG CGGCTAAAAG CCTCACGTCC AGAACAAATT
```

Fig. 6 Cont.

```
5601  ACTGTGTGCT CATCCTTTCC ATTGCCGAAG TATAGAATCA CTGGTGTGCA
5651  GAAGATCCAA TGCTCCCAGC CTATATTGTT CTCACCGAAA GTGCCTGCGT
5701  ATATTCATCC AAGGAAGTAT CTCGTGGAAA CACCACCGGT AGACGAGACT
5751  CCGGAGCCAT CGGCAGAGAA CCAATCCACA GAGGGGACAC CTGAACAACC
5801  ACCACTTATA ACCGAGGATG AGACCAGGAC TAGAACGCCT GAGCCGATCA
5851  TCATCGAAGA GGAAGAAGAG GATAGCATAA GTTTGCTGTC AGATGGCCCG
5901  ACCCACCAGG TGCTGCAAGT CGAGGCAGAC ATTCACGGGC CGCCCTCTGT
5951  ATCTAGCTCA TCCTGGTCCA TTCCTCATGC ATCCGACTTT GATGTGGACA
6001  GTTTATCCAT ACTTGACACC CTGGAGGGAG CTAGCGTGAC CAGCGGGGCA
6051  ACGTCAGCCG AGACTAACTC TTACTTCGCA AAGAGTATGG AGTTTCTGGC
6101  GCGACCGGTG CCTGCGCCTC GAACAGTATT CAGGAACCCT CCACATCCCG
6151  CTCCGCGCAC AAGAACACCG TCACTTGCAC CCAGCAGGGC CTGCTCGAGA
6201  ACCAGCCTAG TTTCCACCCC GCCAGGCGTG AATAGGGTGA TCACTAGAGA
6251  GGAGCTCGAG GCGCTTACCC CGTCACGCAC TCCTAGCAGG TCGGTCTCGA
6301  GAACCAGCCT GGTCTCCAAC CCGCCAGGCG TAAATAGGGT GATTACAAGA
6351  GAGGAGTTTG AGGCGTTCGT AGCACAACAA CAATGACGGT TTGATGCGGG
6401  TGCATACATC TTTTCCTCCG ACACCGGTCA AGGGCATTTA CAACAAAAAT
6451  CAGTAAGGCA AACGGTGCTA TCCGAAGTGG TGTTGGAGAG GACCGAATTG
6501  GAGATTTCGT ATGCCCCGCG CCTCGACCAA GAAAAAGAAG AATTACTACG
6551  CAAGAAATTA CAGTTAAATC CCACACCTGC TAACAGAAGC AGATACCAGT
6601  CCAGGAAGGT GGAGAACATG AAAGCCATAA CAGCTAGACG TATTCTGCAA
6651  CGGCTAGGGC ATTATTTGAA GGCAGAAGGA AAAGTGGAGT GCTACCGAAC
6701  CCTGCATCCT GTTCCTTTGT ATTCATCTAG TGTGAACCGT GCCTTTTCAA
6751  GCCCCAAGGT CGCAGTCGAA GCCTGTAACG CCATGTTGAA AGAGAACTTT
6801  CCGACTGTGG CTTCTTACTG TATTATTCCA GAGTACGATG CCTATTTGGA
6851  CATGGTTGAC GGAGCTTCAT GCTGCTTAGA CACTGCCAGT TTTTGCCCTG
6901  CAAAGCTGCG CAGCTTTCCA AAGAAACACT CCTATTTGGA ACCCACAATA
6951  CGATCGGCAG TGCCTTCAGC GATCCAGAAC ACGCTCCAGA ACGTCCTGGC
7001  AGCTGCCACA AAAGAAATT GCAATGTCAC GCAAATGAGA GAATTGCCCG
7051  TATTGGATTC GGCGGCCTTT AATGTGGAAT GCTTCAAGAA ATATGCGTGT
7101  AATAATGAAT ATTGGAAAC GTTAAAGAA AACCCCATCA GGCTTACTGA
7151  AGAAAACGTG GTAAATTACA TTACCAAATT AAAAGGACCA AAAGCTGCTG
7201  CTCTTTTTGC GAAGACACAT AATTTGAATA TGTTGCAGGA CATACCAATG
7251  GACAGGTTTG TAATGGACTT AAAGAGAGAG GTGAAAGTGA CTCCAGGAAC
7301  AAAACATACT GAAGAACGGC CCAAGGTACA GGTGATCCAG GCTGCCGATC
7351  CGCTAGCAAC AGCGTATCTG TGCGGAATCC ACCGAGAGCT GGTTAGGAGA
7401  TTAAATGCGG TCCTGCTTCC GAACATTCAT ACACTGTTTG ATATGTCGGC
7451  TGAAGACTTT GACGCTATTA TAGCCGAGCA CTTCCAGCCT GGGGATTGTG
```

FIG. 6 CONT.

```
7501  TTCTGGAAAC TGACATCGCG TCGTTTGATA AAAGTGAGGA CGACGCCATG
7551  GCTCTGACCG CGTTAATGAT TCTGGAAGAC TTAGGTGTGG ACGCAGAGCT
7601  GTTGACGCTG ATTGAGGCGG CTTTCGGCGA AATTTCATCA ATACATTTGC
7651  CCACTAAAAC TAAATTTAAA TTCGGAGCCA TGATGAAATC TGGAATGTTC
7701  CTCACACTGT TTGTGAACAC AGTCATTAAC ATTGTAATCG CAAGCAGAGT
7751  GTTGAGAGAA CGGCTAACCG GATCACCATG TGCAGCATTC ATTGGAGATG
7801  ACAATATCGT GAAAGGAGTC AAATCGGACA AATTAATGGC AGACAGGTGC
7851  GCCACCTGGT TGAATATGGA AGTCAAGATT ATAGATGCTG TGGTGGGCGA
7901  GAAAGCGCCt TATTTCTGTG GAGGGTTTAT TTGTGTGAC TCCGTGACCG
7951  GCACAGCGTG CCGTGTGGCA GACCCCCTAA AAACGGCTGTT TAAGCTTGGC
8001  AAACCTCTGG CAGCAGACGA TGAACATGAT GATGACAGGA GAAGGGCATT
8051  GCATGAAGAG TCAACACGCT GGAACCGAGT GGGTATTCTT TCAGAGCTGT
8101  GCAAGGCAGT AGAATCAAGG TATGAAACCG TAGGAACTTC CATCATAGTT
8151  ATGGCCATGA CTACTCTAGC TAGCAGTGTT AAATCATTCA GCTACCTGAG
      ; 26S promoter
8201  AGGGGCCCCT ATAACTCTCT ACGGCTAACC TGAATGGACT ACGACATAGT
8251  CTAGTCCGCC AAGATGTTCC CGTTCCAGCC AATGTATCCG ATGCAGCCAA
8301  TGCCCTATCG CAACCCGTTC GCGGCCCCGC GCAGGCCCTG GTTCCCAGA
8351  ACCGACCCTT TTCTGGCGAT GCAGGTGCAG GAATTAACCC GCTCGATGGC
8401  TAACCTGACG TTCAAGCAAC GCCGGGACGC GCCACCTGAG GGGCCATCCG
8451  CTAAGAAACC GAAGAAGGAG GCCTCGCAAA AACAGAAAGG GGGAGGCCAA
8501  GGGAAGAAGA AGAAGAACCA AGGGAAGAAG AAGGCTAAGA CAGGGCCGCC
8551  TAATCCGAAG GCACAGAATG GAAACAAGAA GAAGACCAAC AAGAAACCAG
8601  GCAAGAGACA GCGCATGGTC ATGAAATTGG AATCTGACAA GACGTTCCCA
8651  ATCATGTTGG AAGGGAAGAT AAACGGCTAC GCTTGTGTCG TCGGAGGGAA
8701  GTTATTCAGG CCGATGCATG TGGAAGGCAA GATCGACAAC GACGTTCTGG
8751  CCGCGCTTAA GACGAAGAAA GCATCCAAAT ACGATCTTGA GTATGCAGAT
8801  GTGCCACAGA ACATGCGGGC CGATACATTC AAATACACCC ATGAGAAACC
8851  CCAAGGCTAT TACAGCTGGC ATCATGGAGC AGTCCAATAT GAAAATGGGC
8901  GTTTCACGGT GCCGAAAGGA GTTGGGGCCA AGGGAGACAG CGGACGACCC
8951  ATTCTGGATA ACCAGGGACG GGTGGTCGCT ATTGTGCTGG GAGGTGTGAA
9001  TGAAGGATCT AGGACAGCCC TTTCAGTCGT CATGTGGAAC GAGAAGGGAG
9051  TTACCGTGAA GTATACTCCG GAGAACTGCG AGCAATGGTC ACTAGTGACC
9101  ACCATGTGTC TGCTCGCCAA TGTGACGTTC CCATGTGCTC AACCACCAAT
9151  TTGCTACGAC AGAAAACCAG CAGAGACTTT GGCCATGCTC AGCGGTTAACG
9201  TTGACAACCC GGGCTACGAT GAGCTGCTGG AAGCAGCTGT TAAGTGCCCC
9251  GGAAGGAAAA GGAGATCCAC CGAGGAGCTG TTTAATGAGT ATAAGCTAAC
9301  GCGCCCTTAC ATGGCCAGAT GCATCAGATG TGCAGTTGGG AGCTGCCATA
9351  GTCCAATAGC AATCGAGGCA GTAAAGAGCG ACGGCACGA CGGTTATGTT
```

Fig. 6 Cont.

```
9401  AGACTTCAGA CTTCCTCGCA GTATGGCCTG GATTCCTCCG GCAACTTAAA
9451  GGGCAGGACC ATGCGGTATG ACATGCACGG GACCATTAAA GAGATACCAC
9501  TACATCAAGT GTCACTCTAT ACATCTCGCC CGTGTCACAT TGTGGATGGG
9551  CACGGTTATT TCCTGCTTGC CAGGTGCCCG GCAGGGGACT CCATCACCAT
9601  GGAATTTAAG AAAGATTCCG TCAGACACTC CTGCTCGGTG CCGTATGAAG
9651  TGAAATTTAA TCCTGTAGGC AGAGAACTCT ATACTCATCC CCCAGAACAC
9701  GGAGTAGAGC AAGCGTGCCA AGTCTACGCA CATGATGCAC AGAACAGAGG
9751  AGCTTATGTC GAGATGCACC TCCCGGGCTC AGAAGTGGAC AGCAGTTTGG
9801  TTTCCTTGAG CGGCAGTTCA GTCACCGTGA CACCTCCTGA TGGGACTAGC
9851  GCCCTGGTGG AATGCGAGTG TGGCGGCACA AAGATCTCCG AGACCATCAA
9901  CAAGACAAAA CAGTTCAGCC AGTGCACAAA GAAGGAGCAG TGCAGAGCAT
9951  ATCGGCTGCA GAACGATAAG TGGGTGTATA ATTCTGACAA ACTGCCCAAA
10001 GCAGCGGCAG CCACCTTAAA AGGAAAACTG CATGTCCCAT TCTTGCTGGC
10051 AGACGGCAAA TGCACCGTGC CTCTAGCACC AGAACCTATG ATAACCTTCG
10101 GTTTCAGATC AGTGTCACTG AAACTGCACC CTAAGAATCC CACATATCTA
10151 ATCACCCGCC AACTTGCTGA TGAGCCTCAC TACACGCACG AGCTCATATC
10201 TGAACCAGCT GTTAGGAATT TTACCGTCAC CGAAAAAGGG TGGGAGTTTG
10251 TATGGGGAAA CCACCCGCCG AAAAGGTTTT GGGCACAGGA AACAGCACCC
10301 GGAAATCCAC ATGGGCTACC GCACGAGGTG ATAACTCATT ATTACCACAG
10351 ATACCCTATG TCCACCATCC TGGGTTTGTC AATTTGTGCC GCCATTGCAA
10401 CCGTTTCCGT TGCAGCGTCT ACCTGGCTGT TTTGCAGATC TAGAGTTGCG
10451 TGCCTAACTC CTTACCGGCT AACACCTAAC GCTAGGATAC CATTTTGTCT
10501 GGCTGTGCTT TGCTGCGCCC GCACTGCCCG GGCCGAGACC ACCTGGGAGT
10551 CCTTGGATCA CCTATGGAAC AATAACCAAC AGATGTTCTG GATTCAATTG
10601 CTGATCCCTC TGGCCGCCTT GATCGTAGTG ACTCGCCCGC TCAGGTGCGT
10651 GTGCTGTGTC GTGCCTTTTT TAGTCATGGC CGGCGCCGCA GGCGCCGGCG
10701 CCTACGAGCA CGCGACCACG ATGCCCAGCC AAGCGGGAAT CTCCTATAAC
10751 ACTATAGTCA ACAGAGCAGG CTACGCACCA CTCCCTATCA GCATAACACC
10801 AACAAAGATC AAGCTGATAC CTACAGTGAA CTTGGAGTAC GTCACCTGCC
10851 ACTACAAAAC AGGAATGGAT TCACCAGCCA TCAAATGCTG CGGATCTCAG
10901 GAATGCACTC CAACTTACAG GCCTGATGAA CAGTGCAAAG TCTTCACAGG
10951 GGTTTACCCG TTCATGTGGG GTGGTGCATA TTGCTTTTGC GACACTGAGA
11001 ACACCCAAGT CAGCAAGGCC TACGTAATGA AATCTGACGA CTGCCTTGCG
11051 GATCATGCTG AAGCATATAA AGCGCACACA GCCTCAGTGC AGGCGTTCCT
11101 CAACATCACA GTGGAGAAC ACTCTATTGT GACTACCGTG TATGTGAATG
11151 GAGAAACTCC TGTGAATTTC AATGGGGTCA AAATAACTGC AGGTCCGCTT
11201 TCCACAGCTT GGACACCCTT TGATCGCAAA ATCGTGCAGT ATGCCCGGGA
11251 GATCTATAAT TATGATTTTC CTGAGTATGG GGCAGGACAA CCAGGAGCAT
```

FIG. 6 CONT.

```
11301  TTGGAGATAT ACAATCCAGA ACAGTCTCAA GCTCTGATCT GTATGCCAAT
11351  ACCAACCTAG TGCTGCAGAG ACCCAAAGCA GGAGCGATCC ACGTGCCATA
11401  CACTCAGGCA CCTTCGGGTT TTGAGCAATG GAAGAAAGAT AAAGCTCCAT
11451  CATTGAAATT TACCGCCCCT TTCGGATGCG AAATATATAC AAACCCCATT
11501  CGCGCCGAAA ACTGTGCTGT AGGGTCAATT CCATTAGCCT TTGACATTCC
11551  CGACGCCTTG TTCACCAGGG TGTCAGAAAC ACCGACACTT TCAGCGGCCG
11601  AATGCACTCT TAACGAGTGC GTGTATTCTT CCGACTTTGG TGGGATCGCC
11651  ACGGTCAAGT ACTCGGCCAG CAAGTCAGGC AAGTGCGCAG TCCATGTGCC
11701  ATCAGGGACT GCTACCCTAA AAGAAGCAGC AGTCGAGCTA ACCGAGCAAG
11751  GGTCGGCGAC TATCCATTTC TCGACCGCAA ATATCCACCC GGAGTTCAGG
11801  CTCCAAATAT GCACATCATA TGTTACGTGC AAAGGTGATT GTCACCCCCC
11851  GAAAGACCAT ATTGTGACAC ACCCTCAGTA TCACGCCCAA ACATTTACAG
11901  CCGCGGTGTC AAAAACCGCG TGGACGTGGT TAACATCCCT GCTGGGAGGA
11951  TCAGCCGTAA TTATTATAAT TGGCTTGGTG CTGGCTACTA TTGTGGCCAT
12001  GTACGTGCTG ACCAACCAGA AACATAATTG AATACAGCAG CAATTGGCAA
12051  GCTGCTTACA TAGAACTCGC GGCGATTGGC ATGCCGCCTT AAAATTTTTA
12101  TTTTATTTTT TCTTTTCTTT TCCGAATCGG ATTTTGTTTT TAATATTTCA
                                  ; TC-83 sequence end
12151  AAAAAAAAAA AAAAAAAAAA GGGTACGCGG CCGCCACTGT GCTGGATATC
12201  TGCAGAATTC CACCACACTG GACTAGTGGA TCAGCTTAAG TTTAAACCGC
12251  TGATCAGCCT CGACTGTGCC TTCTAGTTGC CAGCCATCTG TTGTTTGCCC
12301  CTCCCCCGTG CCTTCCTTGA CCCTGGAAGG TGCCACTCCC ACTGTCCTTT
             ; Poly(A) site
12351  CCTAATAAAA TGAGGAAATT GCATCGCATT GTCTGAGTAG GTGTCATTCT
12401  ATTCTGGGGG GTGGGGTGGG GCAGGAC
```

FIG. 7: IDNA SEQUENCE FRAGMENT OF MODIFIED pAA_TC-83_C_GP
PLASMID

```
   1   ACAAGGCAAG GCTTGACCGA CAATTGCATG AAGAATCTGC TTAGGGTTAG
                                                           ;AscI
  51   GCGTTTTGCG CTGCTTCGCG ATGTACGGGC CAGATATACG CGTGGCGCGC
                                    ;CMV promoter start
 101   CTGACATTGA TTATTGACTA GTTATTAATA GTAATCAATT ACGGGGTCAT
 151   TAGTTCATAG CCCATATATG GAGTTCCGCG TTACATAACT TACGGTAAAT
 201   GGCCCGCCTG GCTGACCGCC CAACGACCCC CGCCCATTGA CGTCAATAAT
 251   GACGTATGTT CCCATAGTAA CGCCAATAGG GACTTTCCAT TGACGTCAAT
 301   GGGTGGAGTA TTTACGGTAA ACTGCCCACT TGGCAGTACA TCAAGTGTAT
 351   CATATGCCAA GTACGCCCCC TATTGACGTC AATGACGGTA AATGGCCCGC
 401   CTGGCATTAT GCCCAGTACA TGACCTTATG GGACTTTCCT ACTTGGCAGT
 451   ACATCTACGT ATTAGTCATC GCTATTACCA TGGTGATGCG GTTTTGGCAG
 501   TACATCAATG GGCGTGGATA GCGGTTTGAC TCACGGGGAT TTCCAAGTCT
 551   CCACCCCATT GACGTCAATG GGAGTTTGTT TTGGCACCAA AATCAACGGG
 601   ACTTTCCAAA ATGTCGTAAC AACTCCGCCC CATTGACGCA AATGGGCGGT
                                                       ; CMV promoter end
 651   AGGCGTGTAC GGTGGGAGGT CTATATAAGC AGAGCTCTCT GGCTAACTAG
       ; TC-83 iDNA start
 701   AGATAGGCGG CGCATGAGAG AAGCCCAGAC CAATTACCTA CCCAAAATGG
 751   AGAAAGTTCA CGTTGACATC GAGGAAGACA GCCCATTCCT CAGAGCTTTG
 801   CAGCGGAGCT TCCCGCAGTT TGAGGTAGAA GCCAAGCAGG TCACTGATAA
 851   TGACCATGCT AATGCCAGAG CGTTTTCGCA TCTGGCTTCA AAACTGATCG
 901   AAACGGAGGT GGACCCATCC GACACGATCC TTGACATTGG AAGTGCGCCC
 951   GCCCGCAGAA TGTATTCTAA GCACAAGTAT CATTGTATCT GTCCGATGAG
1001   ATGTGCGGAA GATCCGGACA GATTGTATAA GTATGCAACT AAGCTGAAGA
1051   AAAACTGTAA GGAAATAACT GATAAGGAAT TGGACAAGAA AATGAAGGAG
1101   CTCGCCGCCG TCATGAGCGA CCCTGACCTG GAAACTGAGA CTATGTGCCT
1151   CCACGACGAC GAGTCGTGTC GCTACGAAGG GCAAGTCGCT GTTTACCAGG
1201   ATGTATACGC GGTTGACGGA CCGACAAGTC TCTATCACCA AGCCAATAAG
1251   GGAGTTAGAG TCGCCTACTG GATAGGCTTT GACACCACCC CTTTTATGTT
1301   TAAGAACTTG GCTGGAGCAT ATCCATCATA CTCTACCAAC TGGGCCGACG
1351   AAACCGTGTT AACGGCTCGT AACATAGGCC TATGCAGCTC TGACGTTATG
1401   GAGCGGTCAC GTAGAGGGAT GTCCATTCTT AGAAGAAGT ATTTGAAACC
1451   ATCCAACAAT GTTCTATTCT CTGTTGGCTC GACCATCTAC CACGAGAAGA
1501   GGGACTTACT GAGGAGCTGG CACCTGCCGT CTGTATTTCA CTTACGTGGC
1551   AAGCAAAATT ACACATGTCG GTGTGAGACT ATAGTTAGTT GCGACGGGTA
1601   CGTCGTTAAA AGAATAGCTA TCAGTCCAGG CCTGTATGGG AAGCCTTCAG
1651   GCTATGCTGC TACGATGCAC CGCGAGGGAT TCTTGTGCTG CAAAGTGACA
1701   GACACATTGA ACGGGGAGAG GGTCTCTTTT CCCGTGTGCA CGTATGTGCC
```

Fig. 7 Cont.

```
1751 AGCTACATTG TGTGACCAAA TGACTGGCAT ACTGGCAACA GATGTCAGTG
1801 CGGACGACGC GCAAAAACTG CTGGTTGGGC TCAACCAGCG TATAGTCGTC
1851 AACGGTCGCA CCCAGAGAAA CACCAATACC ATGAAAAATT ACCTTTTGCC
1901 CGTAGTGGCC CAGGCATTTG CTAGGTGGGC AAAGGAATAT AAGGAAGATC
1951 AAGAAGATGA AAGGCCACTA GGACTACGAG ATAGACAGTT AGTCATGGGG
2001 TGTTGTTGGG CTTTTAGAAG GCACAAGATA ACATCTATTT ATAAGCGCCC
2051 GGATACCCAA ACCATCATCA AAGTGAACAG CGATTTCCAC TCATTCGTGC
2101 TGCCCAGGAT AGGCAGTAAC ACATTGGAGA TCGGGCTGAG AACAAGAATC
2151 AGGAAAATGT TAGAGGAGCA CAAGGAGCCG TCACCTCTCA TTACCGCCGA
2201 GGACGTACAA GAAGCTAAGT GCGCAGCCGA TGAGGCTAAG GAGGTGCGTG
2251 AAGCCGAGGA GTTGCGCGCA GCTCTACCAC CTTTGGCAGC TGATGTTGAG
2301 GAGCCCACTC TGGAAGCCGA TGTCGACTTG ATGTTACAAG AGGCTGGGGC
2351 CGGCTCAGTG GAGACACCTC GTGGCTTGAT AAAGGTTACC AGCTACGCTG
2401 GCGAGGACAA GATCGGCTCT TACGCTGTGC TTTCTCCGCA GGCTGTACTC
2451 AAGAGTGAAA AATTATCTTG CATCCACCCT CTCGCTGAAC AAGTCATAGT
2501 GATAACACAC TCTGGCCGAA AAGGGCGTTA TGCCGTGGAA CCATACCATG
2551 GTAAAGTAGT GGTGCCAGAG GGACATGCAA TACCCGTCCA GGACTTTCAA
2601 GCTCTGAGTG AAAGTGCCAC CATTGTGTAC AACGAACGTG AGTTCGTAAA
2651 CAGGTACCTG CACCATATTG CCACACATGG AGGAGCGCTG AACACTGATG
2701 AAGAATATTA CAAAACTGTC AAGCCCAGCG AGCACGACGG CGAATACCTG
2751 TACGACATCG ACAGGAAACA GTGCGTCAAG AAAGAACTAG TCACTGGGCT
2801 AGGGCTCACA GGCGAGCTGG TGGATCCTCC CTTCCATGAA TTCGCCTACG
2851 AGAGTCTGAG AACACGACCA GCCGCTCCTT ACCAAGTACC AACCATAGGG
2901 GTGTATGGCG TGCCAGGATC AGGCAAGTCT GGCATCATTA AAAGCGCAGT
2951 CACCAAAAAA GATCTAGTGG TGAGCGCCAA GAAAGAAAAC TGTGCAGAAA
3001 TTATAAGGGA CGTCAAGAAA ATGAAAGGGC TGGACGTCAA TGCCAGAACT
3051 GTGGACTCAG TGCTCTTGAA TGGATGCAAA CACCCCGTAG AGACCCTGTA
3101 TATTGACGAA GCTTTTGCTT GTCATGCAGG TACTCTCAGA GCGCTCATAG
3151 CCATTATAAG ACCTAAAAAG GCAGTGCTCT GCGGGGATCC CAAACAGTGC
3201 GGTTTTTTTA ACATGATGTG CCTGAAAGTG CATTTAACC ACGAGATTTG
3251 CACACAAGTC TTCCACAAAA GCATCTCTCG CCGTTGCACT AAATCTGTGA
3301 CTTCGGTCGT CTCAACCTTG TTTTACGACA AAAAAATGAG AACGACGAAT
3351 CCGAAAGAGA CTAAGATTGT GATTGACACT ACCGGCAGTA CCAAACCTAA
3401 GCAGGACGAT CTCATTCTCA CTTGTTTCAG AGGGTGGGTG AAGCAGTTGC
3451 AAATAGATTA CAAAGGCAAC GAAATAATGA CGGCAGCTGC CTCTCAAGGG
3501 CTGACCCGTA AAGGTGTGTA TGCCGTTCGG TACAAGGTGA ATGAAAATCC
3551 TCTGTACGCA CCCACCTCAG AACATGTGAA CGTCCTACTG ACCCGCACGG
3601 AGGACCGCAT CGTGTGGAAA ACACTAGCCG GCGACCCATG GATAAAAACA
```

FIG. 7 CONT.

```
3651  CTGACTGCCA AGTACCCTGG GAATTTCACT GCCACGATAG AGGAGTGGCA
3701  AGCAGAGCAT GATGCCATCA TGAGGCACAT CTTGGAGAGA CCGGACCCTA
3751  CCGACGTCTT CCAGAATAAG GCAAACGTGT GTTGGGCCAA GGCTTTAGTG
3801  CCGGTGCTGA AGACCGCTGG CATAGACATG ACCACTGAAC AATGGAACAC
3851  TGTGGATTAT TTTGAAACGG ACAAAGCTCA CTCAGCAGAG ATAGTATTGA
3901  ACCAACTATG CGTGACGTTC TTTGGACTCG ATCTGGACTC CGGTCTATTT
3951  TCTGCACCCA CTGTTCCGTT ATCCATTAGG AATAATCACT GGGATAACTC
4001  CCCGTCGCCT AACATGTACC GGCTGAATAA AGAAGTGGTC CGTCAGCTCT
4051  CTGCAGGTA CCCACAACTG CCTCGGGCAG TTGCCACTGG AAGAGTCTAT
4101  GACATGAACA CTGGTACACT GCGCAATTAT GATCCGCGCA TAAACCTAGT
4151  ACCTGTAAAC AGAAGACTGC CTCATGCTTT AGTCCTCCAC CATAATGAAC
4201  ACCCACAGAG TGACTTTTCT TCATTCGTCA GCAAATTGAA GGGCAGAACT
4251  GTCCTGGTGG TCGGGAAAA GTTGTCCGTC CCAGGCAAAA TGGTTGACTG
4301  GTTGTCAGAC CGGCCTGAGG CTACCTTCAG AGCTCGGCTG GATTTAGGCA
4351  TCCCAGGTGA TGTGCCCAAA TATGACATAA TATTTGTTAA TGTGAGGACC
4401  CCATATAAAT ACCATCACTA TCAGCAGTGT GAAGACCATG CCATTAAGCT
4451  TAGCATGTTG ACCAAGAAAG CTTGTCTGCA TCTGAATCCC GGCGGAACCT
4501  GTGTCAGCAT AGGTTATGGT TACGCTGACA GGGCCAGCGA AAGCATCATT
4551  GGTGCTATAG CGCGGCAGTT CAAGTTTTCC CGGGTATGCA AACCGAAATC
4601  CTCACTTGAA GAGACGGAAG TTCTGTTTGT ATTCATTGGG TACGATCGCA
4651  AGGCCCGTAC GCACAATCCT TACAAGCTTT CATCAACCTT GACCAACATT
4701  TATACAGGTT CCAGACTCCA CGAAGCCGGA TGTGCACCCT CATATCATGT
4751  GGTGCGAGCG GATATTGCCA CGCCCACCGA AGGAGTGATT ATAAATGCTG
4801  CTAACAGCAA AGGACAACCT GGCGGAGGGG TGTGCGGAGC GCTGTATAAG
4851  AAGTTCCCGG AAAGCTTCGA TTTACAGCCG ATCGAAGTAG GAAAAGCGCG
4901  ACTGGTCAAA GGTGCAGCTA ACATATCAT TCATGCCGTA GGACCAAACT
4951  TCAACAAAGT TTCGGAGGTT GAAGGTGACA AACAGTTCGC AGAGGCTTAT
5001  GAGTCCATCG CTAAGATTGT CAACGATAAC AATTACAAGT CAGTAGCGAT
5051  TCCACTGTTG TCCACCGGCA TCTTTTCCGG GAACAAAGAT CGACTAACCC
5101  AATCATTGAA CCATTTGCTG ACAGCTTTAG ACACCACTGA TGCAGATGTA
5151  GCCATATACT GCAGGGACAA GAAATGGGAA ATGACTCTCA AGGAAGCAGT
5201  GGCTAGGAGA GAAGCAGTGG AGGAGATATG CATATCCGAC GACTCTTCAG
5251  TGACAGAACC TGATGCAGAG CTGGTGAGGG TGCATCCGAA GAGTTCTTTG
5301  GCTGGAAGGA AGGGCTACAG CACAAGCGAT GGCAAAACTT TCTCATATTT
5351  GGAAGGGACC AAGTTTCACC AGGCGGCCAA GGATATAGCA GAAATTAATG
5401  CCATGTGGCC CGTTGCAACG GAGGCCAATG AGCAGGTATG CATGTATATC
5451  CTCGGAGAAA GCATGAGCAG TATTAGGTCG AAATGCCCCG TCGAAGAGTC
5501  GGAAGCCTCC ACACCACCTA GCACGCTGCC TTGCTTGTGC ATCCATGCCA
```

Fig. 7 Cont.

```
5551  TGACTCCAGA AAGAGTACAG CGCCTAAAAG CCTCACGTCC AGAACAAATT
5601  ACTGTGTGCT CATCCTTTCC ATTGCCGAAG TATAGAATCA CTGCTGTGCA
5651  GAAGATCCAA TGCTCCCAGC CTATATTGTT CTCACCGAAA GTGCCTGCGT
5701  ATATTCATCC AAGGAAGTAT CTCGTGGAAA CACCACCGGT AGACGAGACT
5751  CCGGAGCCAT CGGCAGAGAA CCAATCCACA GAGGGACAC CTGAACAACC
5801  ACCACTTATA ACGAGGATG AGACCAGGAC TAGAACGCCT GAGCCGATCA
5851  TCATCGAAGA GGAAGAAGAG GATAGCATAA GTTTGCTGTC AGATGGCCCG
5901  ACCCACCAGG TGCTGCAAGT CGAGGCAGAC ATTCACGGGC CGCCCTCTGT
5951  ATCTAGCTCA TCCTGGTCCA TTCCTCATGC ATCCGACTTT GATGTGGACA
6001  GTTATCCAT ACTTGACACC CTGGAGGGAG CTAGCGTGAC CAGCGGGGCA
6051  ACGTCAGCCG AGACTAACTC TTACTTCGCA AAGAGTATGG AGTTTCTGGC
6101  GCGACCGGTG CCTGCGCCTC GAACAGTATT CAGGAACCCT CCACATCCCG
6151  CTCCGCGCAC AAGAACACCG TCACTTGCAC CCAGCAGGGC CTGCTCGAGA
6201  ACCAGCCTAG TTTCCACCCC GCCAGGCGTG AATAGGGTGA TCACTAGAGA
6251  GGAGCTCGAG GCGCTTACCC CGTCACGCAC TCCTAGCAGG TCGGTCTCGA
6301  GAACCAGCCT GGTCTCCAAC CCGCCAGGCG TAAATAGGGT GATTACAAGA
6351  GAGGAGTTTG AGGCGTTCGT AGCACAACAA CAATGACGGT TTGATGCGGG
6401  TGCATACATC TTTTCCTCCG ACACCGGTCA AGGGCATTTA CAACAAAAAT
6451  CAGTAAGGCA AACGGTGCTA TCCGAAGTGG TGTTGGAGAG GACCGAATTG
6501  GAGATTTCGT ATGCCCCGCG CCTCGACCAA GAAAAGAAG AATTACTACG
6551  CAAGAAATTA CAGTTAAATC CCACACCTGC TAACAGAAGC AGATACCAGT
6601  CCAGGAAGGT GGAGAACATG AAAGCCATAA CAGCTAGACG TATTCTGCAA
6651  GGCCTAGGGC ATTATTTGAA GGCAGAAGGA AAAGTGGAGT GCTACCGAAC
6701  CCTGCATCCT GTTCCTTTGT ATTCATCTAG TGTGAACCGT GCCTTTCAA
6751  GCCCCAAGGT CGCAGTGGAA GCCTGTAACG CCATGTTGAA AGAGAACTTT
6801  CCGACTGTGG CTTCTTACTG TATTATTCCA GAGTACGATG CCTATTTGGA
6851  CATGGTTGAC GGAGCTTCAT GCTGCTTAGA CACTGCCAGT TTTTGCCCTG
6901  CAAAGCTGCG CAGCTTTCCA AAGAAACACT CCTATTTGGA ACCCACAATA
6951  CGATCGGCAG TGCCTTCAGC GATCCAGAAC ACGCTCCAGA ACGTCCTGGC
7001  AGCTGCCACA AAAAGAAATT GCAATGTCAC GCAAATGAGA GAATTGCCCG
7051  TATTGGATTC GGCGGCCTTT AATGTGGAAT GCTTCAAGAA ATATGCGTGT
7101  AATAATGAAT ATTGGGAAAC GTTTAAAGAA AACCCCATCA GGCTTACTGA
7151  AGAAAACGTC GTAAATTACA TTACCAAATT AAAAGGACCA AAAGCTGCTG
7201  CTCTTTTTGC GAAGACACAT AATTTGAATA TGTTGCAGGA CATACCAATG
7251  GACAGGTTTG TAATGGACTT AAAGACAGAC GTGAAAGTGA CTCCAGGAAC
7301  AAAACATACT GAAGAACGGC CAAGGTACA GGTGATCCAG GCTGCCGATC
7351  CGCTAGCAAC AGCGTATCTG TGCGGAATCC ACCGAGAGCT GGTTAGGAGA
7401  TTAAATGCGG TCCTGCTTCC GAACATTCAT ACACTGTTTG ATATGTCGGC
```

FIG. 7 CONT.

```
7451 TGAAGACTTT GACGCTATTA TAGCCCGAGCA CTTCCAGCCT GGGGATTGTG
7501 TTCTGGAAAC TGACATCGCG TCGTTTGATA AAAGTGAGGA CGACGCCATG
7551 GCTCTGACCG CGTTAATGAT TCTGGAAGAC TTAGGTGTGG ACGCAGAGCT
7601 GTTGACGCTG ATTGAGGCGG CTTTCGGCGA AATTTCATCA ATACATTTGC
7651 CCACTAAAAC TAAATTTAAA TTCGGAGCCA TGATGAAATC TGGAATGTTC
7701 CTCACACTGT TTGTGAACAC AGTCATTAAC ATTGTAATCG CAAGCAGAGT
7751 GTTGAGAGAA CGGCTAACCG GATCACCATG TGCAGCATTC ATTGGAGATG
7801 ACAATATCGT GAAAGGAGTC AAATCGGACA AATTAATGGC AGACAGGTGC
7851 GCCACCTGGT TGAATATGGA AGTCAAGATT ATAGATGCTG TGGTGGGCGA
7901 GAAAGCGCCt TATTTCTGTG GAGGGTTTAT TTTGTGTGAC TCCGTGACCG
7951 GCACAGCGTG CCGTGTGGCA GACCCCCTAA AAAGGCTGTT TAAGCTTGGC
8001 AAACCTCTGG CAGCAGACGA TGAACATGAT GATGACAGGA GAAGGGCATT
8051 GCATGAAGAG TCAACACGCT GGAACCGAGT GGGTATTCTT TCAGAGCTGT
8101 GCAAGGCAGT AGAATCAAGG TATGAAACCG TAGGAACTTC CATCATAGTT
8151 ATGGCCATGA CTACTCTAGC TAGCAGTGTT AAATCATTCA GCTACCTGAG
            i26S promoter
8201 AGgGGCCCCT ATAACTCTCT ACGGCTAACC TGAATGGACT ACGACATAGT
8251 CTAGTCCGCC AAGATGTTCC CGTTCCAGCC AATGTATCCG ATGCAGCCAA
8301 TGCCCTATCG CAACCCGTTC GCGGCCCCGC GCAGGCCCTG GTTCCCAGA
8351 ACCGACCCTT TTCTGGCGAT GCAGGTGCAG GAATTAACCC GCTCGATGGC
8401 TAACCTGACG TTCAAGCAAC GCCGGGACGC GCCACCTGAG GGGCCATCCG
8451 CTAAGAAACC GAAGAAGGAG GCCTCGCAAA AACAGAAAGG GGGAGGCCAA
8501 GGGAAGAAGA AGAAGAACCA AGGGAAGAAG AAGGCTAAGA CAGGGCCGCC
8551 TAATCCGAAG GCACAGAATG GAAACAAGAA GAAGACCAAC AAGAAACCAG
8601 GCAAGAGACA GCGCATGGTC ATGAAATTGG AATCTGACAA GACGTTCCCA
8651 ATCATGTTGG AAGGCAAGAT AAACGGCTAC GCTTGTGTGG TCGGAGGGAA
8701 GTTATTCAGG CCGATGCATG TGGAAGGCAA GATCGACAAC GACGTTCTGG
8751 CCGCGCTTAA GACGAAGAAA GCATCCAAAT ACGATCTTGA GTATGCAGAT
8801 GTGCCACAGA ACATGCGGGC CGATACATTC AAATACACCC ATGAGAAACC
8851 CCAAGGCTAT TACAGCTGGC ATCATGGAGC AGTCCAATAT GAAAATGGGC
8901 GTTTCACGGT GCCGAAAGGA GTTGGGGCCA AGGGAGACAG CGGACGACCC
8951 ATTCTGGATA ACCAGGGACG GGTGGTCGCT ATTGTGCTGG GAGGTGTGAA
9001 TGAAGGATCT AGGACAGCCC TTTCAGTCGT CATGTGGAAC GAGAAGGGAG
9051 TTACCGTGAA GTATACTCCG GAGAACTGCG AGCAATGGTG ACTAGTGACC
9101 ACCATGTGTC TGCTCGCCAA TGTGACGTTC CCATGTGCTC AACCACCAAT
                                                      26St
9151 TTGCTACGAC AGAAAACCAG CAGAGACTTT GGCCATGCTC AGCGTTCCTA
9201 TAACTCTCTA CGGCTAACCT GAATGGACTA Cgacatagtc tagtccgcca
9251 agatgtcact agtgaccacc atgtgtctgc tgccaatgt gacgttccca
9301 tgtgctcaac caccaatttg ctacgacaga aaaccagcag agactttggc
```

FIG. 7 CONT.

```
9351  catgctcagc gttaacgttg acaacccggg ctacgatgag ctgctggaag
9401  cagctgttaa gtgcccggga aggaaaagga gatccaccga ggagctgttt
9451  aatgagtata agctaacgcg cccttacatg gccagatgca tcagatgtgc
9501  agttgggagc tgccatagtc caatagcaat cgaggcagta aagagcgacg
9551  ggcacgacgg ttatgttaga cttcagactt cctcgcagta tggcctggat
9601  tcctccggca acttaaaggg caggaccatg cggtatgaca tgcacgggac
9651  cattaaagag ataccactac atcaagtgtc actctatca tctcgcccgt
9701  gtcacattgt ggatgggcac ggttatttcc tgcttgccag gtgcccggca
9751  ggggactcca tcaccatgga atttaagaaa gattccgtca gacactcctg
9801  ctcggtgccg tatgaagtga aatttaatcc tgtaggcaga gaactctata
9851  ctcatccccc agaacacgga gtagagcaag cgtgccaagt ctacgcacat
9901  gatgcacaga acagaggagc ttatgtcgag atgcactcc cgggctcaga
9951  agtggacagc agtttggttt ccttgagcgg cagttcagtc accgtgacac
10001 ctcctgatgg gactagcgcc ctggtggaat gcgagtgtgg cggcacaaag
10051 atctccgaga ccatcaacaa gacaaacag ttcagccagt gcacaaagaa
10101 ggagcagtgc agagcatatc ggctgcagaa cgataagtgg gtgtataatt
10151 ctgacaaact gcccaaagca gcgggagcca ccttaaaagg aaaactgcat
10201 gtcccattct tgctggcaga cggcaaatgc accgtgcctc tagcaccaga
10251 acctatgata accttcggtt tcagatcagt gtcactgaaa ctgcaccta
10301 agaatcccac atatctaatc acccgccaac ttgctgatga gcctcactac
10351 acgcacgagc tcatatctga accagctgtt aggaatttta ccgtcaccga
10401 aaaagggtgg gagtttgtat ggggaaacca cccgccgaaa aggttttggg
10451 cacaggaaac agcaccggga aatccacatg ggctaccgca cgaggtgata
10501 actcattatt accacagata ccctatgtcc accatcctgg gtttgtcaat
10551 ttgtgccgcc attgcaaccg tttccgttgc agcgtctacc tggctgtttt
10601 gcagatctag agttgcgtgc ctaactcctt accggctaac acctaacgct
10651 aggataccat tttgtctggc tgtgctttgc tgcgcccgca ctgccgggc
10701 cgagaccacc tgggagtcct tggatcacct atggaacaat aaccaacaga
10751 tgttctggat tcaattgctg atccctctgg ccgccttgat cgtagtgact
10801 cgcctgctca ggtgcgtgtg ctgtgtcgtg ccttttttag tcatggccgg
10851 cgccgcaggc gccggcgcct acgagcacgc gaccacgatg ccgagccaag
10901 cgggaatctc gtataacact atagtcaaca gagcaggcta cgcaccactc
10951 cctatcagca taacaccaac aaagatcaag ctgataccta cagtgaactt
11001 ggagtacgtc acctgccact acaaacagg aatggattca ccagccatca
11051 aatgctgcgg atctcaggaa tgcactccaa cttacaggcc tgatgaacag
11101 tgcaaagtct tcacaggggt ttacccgttc atgtggggtg gtgcatattg
11151 cttttgcgac actgagaaca cccaagtcag caggcctac gtaatgaaat
11201 ctgacgactg ccttgggggat catgctgaag catataaagc gcacacagcc
```

FIG. 7 CONT.

```
11251  tcagtgcagg cgttcctcaa catcacagtg ggagaacact ctattgtgac
11301  taccgtgtat gtgaatggag aaactcctgt gaatttcaat ggggtcaaaa
11351  taactgcagg tccgctttcc acagcttgga cacccttga tcgcaaaatc
11401  gtgcagtatg ccggggagat ctataattat gattttcctg agtatggggc
11451  aggacaacca ggagcatttg gagatataca atccagaaca gtctcaagct
11501  ctgatctgta tgccaatacc aacctagtgc tgcagagacc caaagcagga
11551  gcgatccacg tgccatacac tcaggcacct tcgggttttg agcaatggaa
11601  gaaagataaa gctccatcat tgaaatttac cgcccctttc ggatgcgaaa
11651  tatatacaaa ccccattcgc gccgaaaact gtgctgtagg gtcaattcca
11701  ttagcctttg acattcccga cgccttgttc accagggtgt cagaaacacc
11751  gacactttca gcggccgaat gcactcttaa cgagtgcgtg tattcttccg
11801  actttggtgg gatcgccacg gtcaagtact cggccagcaa gtcaggcaag
11851  tgcgcagtcc atgtgccatc agggactgct accctaaaag aagcagcagt
11901  cgagctaacc gagcaagggt cggcgactat ccatttctcg accgcaaata
11951  tccacccgga gttcaggctc caaatatgca catcatatgt tacgtgcaaa
12001  ggtgattgtc acccccccgaa agaccatatt gtgacacacc ctcagtatca
12051  cgcccaaaca tttacagccg cggTGTCAAA AACCGCGTGG ACGTGGTTAA
12101  CATCCCTGCT GGGAGGATCA GCCGTAATTA TTATAATTGG CTTGGTGCTG
12151  GCTACTATTG TGGCCATGTA CGTGCTGACC AACCAGAAAC ATAATTGAAT
12201  ACAGCAGCAA TTGGCAAGCT GCTTACATAG AACTCGCGGC GATTGGCATG
12251  CCGCCTTAAA ATTTTTATTT TATTTTTTCT TTTCTTTTCC GAATCGGATT
                                     ; TC-83 sequence end
12301  TTGTTTTTAA TATTTCAAAA AAAAAAAAAA AAAAAAAGGG TACGCGGCCG
12351  CCACTGTGCT GGATATCTGC AGAATTCCAC CACACTGGAC TAGTGGATCA
12401  GCTTAAGTTT AAACCGCTGA TCAGCCTCGA CTGTGCCTTC TAGTTGCCAG
12451  CCATCTGTTG TTTGCCCCTC CCCCGTGCCT TCCTTGACCC TGGAAGGTGC
                       ; Poly(A) site
12501  CACTCCCACT GTCCTTTCCT AATAAAATGA GGAAATTGCA TCGCATTGTC
12551  TGAGTAGGTG TCATTCTATT CTGGGGGGTG GGGTGGGGCA GGAC
```

FIG. 8: iDNA SEQUENCE FRAGMENT OF pCMV_YF17D

```
   1  ACAAGGCAAG GCTTGACCGA CAATTGCATG AAGAATCTGC TTAGGGTTAG
  51  GCGTTTTGCG CTGCTTCGCG ATGTACGGGC CAGATATACG CGTGGCGCGC
                            ↓CMV PROMOTER START
 101  CTGACATTGA TTATTGACTA GTTATTAATA GTAATCAATT ACGGGGTCAT
 151  TAGTTCATAG CCCATATATG GAGTTCCGCG TTACATAACT TACGGTAAAT
 201  GGCCCGCCTG GCTGACCGCC CAACGACCCC CGCCCATTGA CGTCAATAAT
 251  GACGTATGTT CCCATAGTAA CGCCAATAGG GACTTTCCAT TGACGTCAAT
 301  GGGTGGAGTA TTTACGGTAA ACTGCCCACT TGGCAGTACA TCAAGTGTAT
 351  CATATGCCAA GTACGCCCCC TATTGACGTC AATGACGGTA AATGGCCCGC
 401  CTGGCATTAT GCCCAGTACA TGACCTTATG GGACTTTCCT ACTTGGCAGT
 451  ACATCTACGT ATTAGTCATC GCTATTACCA TGGTGATGCG GTTTTGGCAG
 501  TACATCAATG GGCGTGGATA GCGGTTTGAC TCACGGGGAT TTCCAAGTCT
 551  CCACCCCATT GACGTCAATG GGAGTTTGTT TTGGCACCAA AATCAACGGG
 601  ACTTTCCAAA ATGTCGTAAC AACTCCGCCC CATTGACGCA AATGGGCGGT
                                                ↓CMV PROMOTER END
 651  AGGCGTGTAC GGTGGGAGGT CTATATAAGC AGAGCTCTCT GGCTAACTAG
        ↓ YF 17D iDNA start
 701  AGAGTAAATC CTGTGTGCTA ATTGAGGTGC ATTGGTCTGC AAATCGAGTT
 751  GCTAGGCAAT AAACACATTT GGATTAATTT TAATCGTTCG TTGAGCGATT
 801  AGCAGAGAAC TGACCAGAAC ATGTCTGGTC GTAAAGCTCA GGGAAAAACC
 851  CTGGGCGTCA ATATGGTACG ACGAGGAGTT CGCTCCTTGT CAAACAAAAT
 901  AAAACAAAAA ACAAAACAAA TTGGAAACAG ACCTGGACCT TCAAGAGGTG
 951  TTCAAGGATT TATCTTTTTC TTTTTGTTCA ACATTTTGAC TGGAAAAAAG
1001  ATCACAGCCC ACCTAAAGAG GTTGTGGAAA ATGCTGGACC CAAGACAAGG
1051  CTTGGCTGTT CTAAGGAAAG TCAAGAGAGT GGTGGCCAGT TTGATGAGAG
1101  GATTGTCCTC AAGGAAACGC CGTTCCCATG ATGTTCTGAC TGTGCAATTC
1151  CTAATTTTGG GAATGCTGTT GATGACGGGT GGAGTGACCT TGGTGCGGAA
1201  AAACAGATGG TTGCTCCTAA ATGTGACATC TGAGGACCTC GGGAAAACAT
1251  TCTCTGTGGG CACAGGCAAC TGCACAACAA ACATTTTGGA AGCCAAGTAC
1301  TGGTGCCCAG ACTCAATGGA ATACAACTGT CCCAATCTCA GTCCAAGAGA
1351  GGAGCCAGAT GACATTGATT GCTGGTGCTA TGGGGTGGAA AACGTTAGAG
1401  TCGCATATGG TAAGTGTGAC TCAGCAGGCA GGTCTAGGAG GTCAAGAAGG
1451  GCCATTGACT TGCCTACGCA TGAAAACCAT GGTTTGAAGA CCCGGCAAGA
1501  AAAATGGATG ACTGGAAGAA TGGGTGAAAG GCAACTCCAA AAGATTGAGA
1551  GATGGTTCGT GAGGAACCCC TTTTTTGCAG TGACGGCTCT GACCATTGCC
1601  TACCTTGTGG GAAGCAACAT GACGCAACGA GTCGTGATTG CCCTACTGGT
1651  CTTGGCTGTT GGTCCGGCCT ACTCAGCTCA CTGCATTGGA ATTACTGACA
1701  GGGATTTCAT TGAGGGGGTG CATGGAGGAA CTTGGGTTTC AGCTACCCTG
1751  GAGCAAGACA AGTGTGTCAC TGTTATGGCC CCTGACAAGC CTTCATTGGA
```

FIG. 8 CONT.

```
1801  CATCTCACTA GAGACAGTAG CCATTGATAG ACCTGCTGAG GTGAGGAAAG
1851  TGTGTTACAA TGCAGTTCTC ACTCATGTGA AGATTAATGA CAAGTGCCCC
1901  AGCACTGGAG AGGCCCACCT AGCTGAAGAG AACGAAGGGG ACAATGCGTG
1951  CAAGCGCACT TATTCTGATA GAGGCTGGGG CAATGGCTGT GGCCTATTTG
2001  GGAAAGGGAG CATTGTGGCA TGCGCCAAAT TCACTTGTGC CAAATCCATG
2051  AGTTTGTTTG AGGTTGATCA GACCAAAATT CAGTATGTCA TCAGAGCACA
2101  ATTGCATGTA GGGGCCAAGC AGGAAAATTG GAATACCGAC ATTAAGACTC
2151  TCAAGTTTGA TGCCCTGTCA GGCTCCCAGG AAGTCGAGTT CATTGGGTAT
2201  GGAAAAGCTA CACTGGAATG CCAGGTGCAA ACTGCGGTGG ACTTTGGTAA
2251  CAGTTACATC GCTGAGATGG AAACAGAGAG CTGGATACTG GACAGACAGT
2301  GGGCCCAGGA CTTGACCCTG CCATGGCAGA GTGGAAGTGG CGGGGTGTGG
2351  AGAGAGATGC ATCATCTTGT CGAATTTGAA CCTCCGCATG CCGCCACTAT
2401  CAGAGTACTG GCCCTGGGAA ACCAGGAAGG CTCCTTGAAA ACAGCTCTTA
2451  CTGGCCCAAT GAGGGTTACA AAGGACACAA ATGACAACAA CCTTTACAAA
2501  CTACATGGTG GACATGTTTC TTGCAGAGTG AAATTGTCAG CTTTGACACT
2551  CAAGGGGACA TCCTACAAAA TATGCACTGA CAAAATGTTT TTTGTCAAGA
2601  ACCCAACTGA CACTGGCCAT GGCACTGTTG TGATGCAGGT GAAAGTGTCA
2651  AAAGGAGCCC CCTGCAGGAT TCCAGTGATA GTAGCTGATG ATCTTACAGC
2701  GGCAATCAAT AAAGGCATTT TGGTTACAGT TAACCCCATC GCCTCAACCA
2751  ATGATGATGA AGTGCTGATT GAGGTGAACC CACCTTTTGG AGACAGCTAC
2801  ATTATCGTTG GGAGAGGAGA TTCACGTCTC ACTTACCAGT GGCACAAAGA
2851  GGGAAGCTCA ATAGGAAAGT TGTTCACTCA GACCATGAAA GGCGTGGAAC
2901  GCCTGGCCGT CATGGGAGAC ACCGCCTGGG ATTTCAGCTC CGCTGGAGGG
2951  TTCTTCACTT CGGTTGGGAA AGGAATTCAT ACGGTGTTTG GCTCTGCCTT
3001  TCAGGGGCTA TTTGGCGGCT TGAACTGGAT AACAAAGGTC ATCATGGGGG
3051  CGGTACTTAT ATGGGTTGGC ATCAACACAA GAAACATGAC AATGTCCATG
3101  AGCATGATCT TGGTAGGAGT GATCATGATG TTTTTGTCTC TAGGAGTTGG
3151  GGCGGATCAA GGATGCGCCA TCAACTTTGG CAAGAGAGAG CTCAAGTGCG
3201  GAGATGGTAT CTTCATATTT AGAGACTCTG ATGACTGGCT GAACAAGTAC
3251  TCATACTATC CAGAAGATCC TGTGAAGCTT GCATCAATAG TGAAAGCCTC
3301  TTTTGAAGAA GGGAAGTGTG GCCTAAATTC AGTTGACTCC CTTGAGCATG
3351  AGATGTGGAG AAGCAGGGCA GATGAGATCA ATGCCATTTT TGAGGAAAAC
3401  GAGGTGGACA TTTCTGTTGT CGTGCAGGAT CCAAAGAATG TTTACCAGAG
3451  AGGAACTCAT CCATTTTCCA GAATTCGGGA TGGTCTGCAG TATGGTTGGA
3501  AGACTTGGGG TAAGAACCTT GTGTTCTCCC CAGGGAGGAA GAATGGAAGC
3551  TTCATCATAG ATGGAAAGTC CAGGAAAGAA TGCCCGTTTT CAAACCGGGT
3601  CTGGAATTCT TTCCAGATAG AGGAGTTTGG GACGGGAGTG TTCACCACAC
3651  GCGTGTACAT GGACGCAGTC TTTGAATACA CCATAGACTG CGATGGATCT
```

Fig. 8 Cont.

```
3701  ATCTTGGGTG CAGCGGTGAA CCGAAAAAAG AGTGCCCATG GCTCTCCAAC
3751  ATTTTGGATG GGAAGTCATG AAGTAAATGG GACATGGATG ATCCACACCT
3801  TGGAGGCATT AGATTACAAG GAGTGTGAGT GGCCACTGAC ACATACGATT
3851  GGAACATCAG TTGAAGAGAG TGAAATCTTC ATGCCAGAT CAATCGGAGG
3901  CCCAGTTAGC TCTCACAATC ATATCCCTGG ATACAAGGTT CAGACGAACG
3951  GACCTTGGAT GCAGGTACCA CTAGAAGTGA AGAGAGAAGC TTGCCCAGGG
4001  ACTAGCGTGA TCATTGATGG CAACTCTGAT GGACGGGGAA AATCAACCAG
4051  ATCCACCACG GATAGCGGGA AAGTTATTCC TGAATGGTCT TGCCGCTCCT
4101  GCACAATGCC GCCTGTGAGC TTCCATGGTA GTGATGCGTG TTGGTATCCC
4151  ATGGAAATTA GGCCAAGGAA AACGCATGAA AGCCATCTCG TGCGCTCCTG
4201  GGTTACAGCT GGAGAAATAC ATGCTGTCCC TTTTGGTTTG GTGAGCATGA
4251  TGATAGCAAT GGAAGTGGTC CTAAGCAAAA GACAGGGACC AAAGCAAATG
4301  TTGGTTGGAG GAGTAGTGCT CTTGGGAGCA ATGCTGGTCG GGCAAGTAAC
4351  TCTCCTTGAT TTGCTGAAAC TCACAGTGGC TGTGGGATTG CATTTCCATG
4401  AGATGAACAA TGGAGGAGAC GCCATGTATA TGGCGTTGAT TGCTGCCTTT
4451  TCAATCAGAC CAGGGCTGCT CATCGGCTTT GGGCTCAGGA CCCTATGGAG
4501  CCCTCGGGAA CGCCTTCTGC TGACCCTAGG AGCAGCCATG GTGGAGATTG
4551  CCTTGGGTGG CGTGATGGGC GGCCTGTGGA AGTATCTAAA TGCAGTTTCT
4601  CTCTGCATCC TGACAATAAA TGCTGTTGCT TCTAGGAAAG CATCAAATAC
4651  CATCTTGCCC CTCATGGCTC TGTTGACACC TGTCACTATG GCTGAGGTGA
4701  GACTTGCCGC AATGTTCTTT TGTGCCGTGG TTATCATAGG GGTCCTTCAC
4751  CAGAATTTCA AGGACACCTC CATGCAGAAG ACTATACCTC TGCTGGCCCT
4801  CACACTCACA TCTTACCTGG GCTTGACACA ACCTTTTTTG GGCCTGTGTG
4851  CATTTCTGGC AACCCGCATA TTTGGGCGAA GGAGTATCCC AGTGAATGAG
4901  GCACTCGCAG CAGCTGGTCT AGTGGGAGTG CTGGCAGGAC TGGCTTTTCA
4951  GGAGATGGAG AACTTCCTTG GTCCGATTGC AGTTGGAGGA CTCCTGATGA
5001  TGCTGGTTAG CGTGGCTGGG AGGGTGGATG GGCTAGAGCT CAAGAAGCTT
5051  GGTGAAGTTT CATGGGAAGA GGAGGCGGAG ATCAGCGGGA GTTCCGCCCG
5101  CTATGATGTG GCACTCAGTG AACAAGGGGA GTTCAAGCTG CTTTCTGAAG
5151  AGAAAGTGCC ATGGGACCAG GTTGTGATGA CCTCGCTGGC CTTGGTTGGG
5201  GCTGCCCTCC ATCCATTTGC TCTTCTGCTG GTCCTTGCTG GGTGGCTGTT
5251  TCATGTCAGG GGAGCTAGGA GAAGTGGGGA TGTCTTGTGG GATATTCCCA
5301  CTCCTAAGAT CATCGAGGAA TGTGAACATC TGGAGGATGG GATTTATGGC
5351  ATATTCCAGT CAACCTTCTT GGGGGCCTCC CAGCGAGGAG TGGGAGTGGC
5401  ACAGGGAGGG GTGTTCCACA CAATGTGGCA TGTCACAAGA GGAGCTTTCC
5451  TTGTCAGGAA TGGCAAGAAG TTGATTCCAT CTTGGGCTTC AGTAAAGGAA
5501  GACCTTGTCG CCTATGGTGG CTCATGGAAG TTGGAAGGCA GATGGCATCG
5551  AGAGGAAGAG GTCCAGTTGA TGGCGGCTCT TCCAGGAAAG AACGTGGTCA
```

Fig. 8 Cont.

```
5601  ACGTCCAGAC AAAACCGAGC TTGTTCAAAG TGAGGAATGG GGGAGAAATC
5651  GGGGCTGTCG CTCTTGACTA TCCGAGTGGC ACTTCAGGAT CTCCTATTGT
5701  TAACAGGAAC GGAGAGGTGA TTGGGCTGTA CGGCAATGGC ATCCTTGTCG
5751  GTGACAACTC CTTCGTGTCC GCCATATCCC AGACTGAGGT GAAGGAAGAA
5801  GGAAAGGAGG AGCTCCAAGA GATCCCGACA ATGCTAAAGA AAGGAATGAC
5851  AACTGTCCTT GATTTTCATC CTGGAGCTGG GAAGACAAGA CGTTTCCTCC
5901  CACAGATCTT GGCCGAGTGC GCACGGAGAC GCTTGCGCAC TCTTGTGTTG
5951  GCCCCCACCA GGGTTGTTCT TTCTGAAATG AAGGAGGCTT TTCACGGCCT
6001  GGACGTGAAA TTCCACACAC AGGCTTTTTC CGCTCACGGC AGCGGAGAG
6051  AAGTCATTGA TGCCATGTGC CATGCCACCC TAACTTACAG GATGTTGGAA
6101  CCAACTAGGG TTGTTAACTG GAAGTGATC ATTATGGATG AAGCCCATTT
6151  TTTGGATCCA GCTAGCATAG CCGCTAGAGG TTGGGCAGCG CACAGAGCTA
6201  GGGCAAATGA AAGTGCAACA ATCTTGATGA CAGCCACACC GCCTGGGACT
6251  AGTGATGAAT TTCCACATTC AAATGGTGAA ATAGAAGATG TTCAAACGGA
6301  CATACCCAGT GAGCCCTGGA ACACAGGGCA TGACTGGATC CTAGCTGACA
6351  AAAGGCCCAC GGCATGGTTC CTTCCATCCA TCAGAGCTGC AAATGTCATG
6401  GCTGCCTCTT TGCGTAAGGC TGGAAAGAGT GTGGTGGTCC TGAACAGGAA
6451  AACCTTTGAG AGAGAATACC CCACGATAAA GCAGAAGAAA CCTGACTTTA
6501  TATTGGCCAC TGACATAGCT GAAATGGGAG CCAACCTTTG CGTGGAGCGA
6551  GTGCTGGATT GCAGGACGGC TTTTAAGCCT GTGCTTGTGG ATGAAGGGAG
6601  GAAGGTGGCA ATAAAAGGGC CACTTCGTAT CTCCGCATCC TCTGCTGCTC
6651  AAAGGAGGGG GCGCATTGGG AGAAATCCCA ACAGAGATGG AGACTCATAC
6701  TACTATTCTG AGCCTACAAG TGAAAATAAT GCCCACCACG TCTGCTGGTT
6751  GGAGGCCTCA ATGCTCTTGG ACAACATGGA GGTGAGGGGT GGAATGGTCG
6801  CCCCACTCTA TGGCGTTGAA GGAACTAAAA CACCAGTTTC CCCTGGTGAA
6851  ATGACACTGA GGGATGACCA GAGGAAAGTC TTCAGAGAAC TAGTGAGGAA
6901  TTGTGACCTG CCCGTTTGGC TTTCGTGGCA AGTGGCCAAG GCTGGTTTGA
6951  AGACGAATGA TCGTAAGTGG TGTTTTGAAG GCCCTGAGGA ACATGAGATC
7001  TTGAATGACA GCGGTGAAAC AGTGAAGTGC AGGGCTCCTG GAGGAGCAAA
7051  GAAGCCTCTG CGCCCAAGGT GGTGTGATGA AAGGGTGTCA TCTGACCAGA
7101  GTGCGCTGTC TGAATTTATT AAGTTTGCTG AAGGTAGGAG GGGAGCTGCT
7151  GAAGTGCTAG TTGTGCTGAG TGAACTCCCT GATTTCCTGG CTAAAAAAGG
7201  TGGAGAGGCA ATGGATACCA TCAGTGTGTT CCTCCACTCT GAGGAAGGCT
7251  CTAGGGCTTA CCGCAATGCA CTATCAATGA TGCCTGAGGC AATGACAATA
7301  GTCATGCTGT TTATACTGGC TGGACTACTG ACATCGGGAA TGGTCATCTT
7351  TTTCATGTCT CCCAAAGGCA TCAGTAGAAT GTCTATGGCG ATGGGCACAA
7401  TGGCCGGCTG TGGATATCTC ATGTTCCTTG GAGGCGTCAA ACCCACTCAC
7451  ATCTCCTATG TCATGCTCAT ATTCTTTGTC CTGATGGTGG TTGTGATCCC
```

Fig. 8 Cont.

```
7501 CGAGCCAGGG CAACAAAGGT CCATCCAAGA CAACCAAGTG GCATACCTCA
7551 TTATTGGCAT CCTGACGCTG GTTTCAGCGG TGGCAGCCAA CGAGCTAGGC
7601 ATGCTGGAGA AAACCAAAGA GGACCTCTTT GGGAAGAAGA ACTTAATTCC
7651 ATCTAGTGCT TCACCCTGGA GTTGGCCGGA TCTTGACCTG AAGCCAGGAG
7701 CTGCCTGGAC AGTGTACGTT GGCATTGTTA CAATGCTCTC TCCAATGTTG
7751 CACCCACTGGA TCAAAGTCGA ATATGGCAAC CTGTCTCTGT CTGGAATAGC
7801 CCAGTCAGCC TCAGTCCTTT CTTTCATGGA CAAGGGGATA CCATTCATGA
7851 AGATGAATAT CTCGGTCATA ATGCTGCTGG TCAGTGGCTG GAATTCAATA
7901 ACAGTGATGC CTCTGCTCTG TGGCATAGGG TGCGCCATGC TCCACTGGTC
7951 TCTCATTTTA CCTGGAATCA AAGCGCAGCA GTCAAAGCTT GCACAGAGAA
8001 GGGTGTTCCA TGGCGTTGCC GAGAACCCTG TGGTTGATGG GAATCCAACA
8051 GTTGACATTG AGGAAGCTCC TGAAATGCCT GCCCTTTATG AGAAGAAACT
8101 GGCTCTATAT CTCCTTCTTG CTCTCAGCCT AGCTTCTGTT GCCATGTGCA
8151 GAACGCCCTT TTCATTGGCT GAAGGCATTG TCCTAGCATC AGCTGCCTTA
8201 GGGCCGCTCA TAGAGGGAAA CACCAGCCTT CTTTGGAATG GACCCATGGC
8251 TGTCTCCATG ACAGGAGTCA TGAGGGGGAA TCACTATGCT TTTGTGGGAG
8301 TCATGTACAA TCTATGGAAG ATGAAAACTG GACGCCGGGG GAGCGCGAAT
8351 GGAAAAACTT TGGGTGAAGT CTGGAAGAGG GAACTGAATC TGTTGGACAA
8401 GCGACAGTTT GAGTTGTATA AAAGGACCGA CATTGTGGAG GTGGATCGTG
8451 ATACGGCACG CAGGCATTTG GCCGAAGGGA AGGTGGACAC CGGGGTGGCG
8501 GTCTCCAGGG GGACCGCAAA GTTAAGGTGG TTCCATGAGC GTGGCTATGT
8551 CAAGCTGGAA GGTAGGGTGA TTGACCTGGG GTGTGGCCGC GGAGGCTGGT
8601 GTTACTACGC TGCTGCGCAA AAGGAAGTGA GTGGGGTCAA AGGATTTACT
8651 CTTGGAAGAG ACGGCCATGA GAAACCCATG AATGTGCAAA GTCTGGGATG
8701 GAACATCATC ACCTTCAAGG ACAAAACTGA TATCCACCGC CTAGAACCAG
8751 TGAAATGTGA CACCCTTTTG TGTGACATTG GAGAGTCATC ATCGTCATCG
8801 GTCACAGAGG GGGAAAGGAC CGTGAGAGTT CTTGATACTG TAGAAAAATG
8851 GCTGGCTTGT GGGGTTGACA ACTTCTGTGT GAAGGTGTTA GCTCCATACA
8901 TGCCAGATGT TCTCGAGAAA CTGGAATTGC TCCAAAGGAG GTTTGGCGGA
8951 ACAGTGATCA GGAACCCTCT CTCCAGGAAT TCCACTCATG AAATGTACTA
9001 CGTGTCTGGA GCCCGCAGCA ATGTCACATT TACTGTGAAC CAAACATCCC
9051 GCCTCCTGAT GAGGAGAATG AGGCGTCCAA CTGGAAAAGT GACCCTGGAG
9101 GCTGACGTCA TCCTCCCAAT TGGGACACGC AGTGTTGAGA CAGACAAGGG
9151 ACCCCTGGAC AAAGAGGCCA TAGAAGAAAG GGTTGAGAGG ATAAAATCTG
9201 AGTACATGAC CTCTTGGTTT TATGACAATG ACAACCCCTA CAGGACCTGG
9251 CACTACTGTG GCTCCTATGT CACAAAAACC TCAGGAAGTG CGGCGAGCAT
9301 GGTAAATGGT GTTATTAAAA TTCTGACATA TCCATGGGAC AGGATAGAGG
9351 AGGTCACAAG AATGGCAATG ACTGACACAA CCCCTTTTGG ACAGCAAAGA
```

Fig. 8 Cont.

```
9401   GTGTTTAAAG AAAAAGTTGA CACCAGAGCA AAGGATCCAC CAGCGGGAAC
9451   TAGGAAGATC ATGAAAGTTG TCAACAGGTG GCTGTTCCGC CACCTGGCCA
9501   GAGAAAAGAA CCCCAGACTG TGCACAAAGG AAGAATTTAT TGCAAAAGTC
9551   CGAAGTCATG CAGCCATTGG AGCTTACCTG GAAGAACAAG AACAGTGGAA
9601   GACTGCCAAT GAGGCTGTCC AAGACCCAAA GTTCTGGGAA CTGGTGGATG
9651   AAGAAAGGAA GCTGCACCAA CAAGGCAGGT GTCGGACTTG TGTGTACAAC
9701   ATGATGGGGA AAAGAGAGAA GAAGCTGTCA GAGTTTGGGA AAGCAAACGG
9751   AAGCCGTGCC ATATGGTATA TGTGGCTGGG AGCGCGGTAT CTTGAGTTTG
9801   AGGCCCTGGG ATTCCTGAAT GAGGACCATT GGGCTTCCAG GGAAAACTCA
9851   GGAGGAGGAG TGGAAGGCAT TGGCTTACAA TACCTAGGGAT ATGTGATCAG
9901   AGACCTGGCT GCAATGGATG GTGGTGGATT CTACGCGGAT GACACCGCTG
9951   GATGGGACAC GCGCATCACA GAGGCAGACC TTGATGATGA ACAGGAGATC
10001  TTGAACTACA TGAGCCCACA TCACAAAAAA CTGGCACAAG CAGTGATGGA
10051  AATGACATAC AAGAACAAAG TGGTGAAAGT GTTGAGACCA GCCCCAGGAG
10101  GGAAAGCCTA CATGGATGTC ATAAGTCGAC GAGACCAGAG AGGATCCGGG
10151  CAGGTAGTGA CTTATGCTCT GAACACCATC ACCAACTTGA AAGTCCAATT
10201  GATCAGAATG GCAGAAGCAG AGATGGTGAT ACATCACCAA CATGTTCAAG
10251  ATTGTGATGA ATCAGTTCTG ACCAGGCTGG AGGCATGGCT CACTGAGCAC
10301  GGATGTGACA GACTGAAGAG GATGGCGGTG AGTGGAGACG ACTGTGTGGT
10351  CCGGCCCATC GATGACAGGT TCGCCCTGGC CCTGTCCCAT CTCAACGCCA
10401  TGTCCAAGGT TAGAAAGGAC ATATCTGAAT GGCAGCCATC AAAAGGGTGG
10451  AATGATTGGG AGAATGTGCC CTTCTGTTCC CACCACTTCC ATGAACTACA
10501  GCTGAAGGAT GGCAGGAGGA TTGTGGTGCC TTGCCGAGAA CAGGACGAGC
10551  TCATTGGGAG AGGAAGGGTG TCTCCAGGAA ACGGCTGGAT GATCAAGGAA
10601  ACAGCTTGCC TCAGCAAAGC CTATGCCAAC ATGTGGTCAC TGATGTATTT
10651  TCACAAAAGG GACATGAGGC TACTGTCATT GGCTGTTTCC TCAGCTGTTC
10701  CCACCTCATG GGTTCCACAA GGACGCACAA CATGGTCGAT TCATGGGAAA
10751  GGGGAGTGGA TGACCACGGA AGACATGCTT GAGGTGTGGA ACAGAGTATG
10801  GATAACCAAC AACCCACACA TGCAGGACAA GACAATGGTG AAAAAATGGA
10851  GAGATGTCCC TTATCTAACC AAGAGACAAG ACAAGCTGTG CGGATCACTG
10901  ATTGGAATGA CCAATAGGGC CACCTGGGCC TCCCACATCC ATTTAGTCAT
10951  CCATCGTATC CGAACGCTGA TTGGACAGGA GAAATACACT GACTACCTAA
11001  CAGTCATGGA CAGGTATTCT GTGGATGCTG ACCTGCAACT GGGTGAGCTT
11051  ATCTGAAACA CCATCTAACA GGAATAACCG GGATACAAAC CACGGGTGGA
11101  GAACCGGACT CCCCACAACC TGAAACCGGG ATATAAACCA CGGCTGGAGA
11151  ACCGGGCTCC GCACTTAAAA TGAAACAGAA ACCGGGATAA AAACTACGGA
11201  TGGAGAACCG GACTCCACAC ATTGAGACAG AAGAAGTTGT CAGCCCAGAA
11251  CCCCACACGA GTTTTGCCAC TGCTAAGCTG TGAGGCAGTG CAGGCTGGGA
```

FIG. 8 CONT.

```
11301  CAGCCGACCT CCAGGTTGCG AAAAACCTGG TTTCTGGGAC CTCCCACCCC
11351  AGAGTAAAAA GAACGGAGCC TCCGCTACCA CCCTCCCACG TGGTGGTAGA
11401  AAGACGGGGT CTAGAGGTTA GAGGAGACCC TCCAGGGAAC AAATAGTGGG
11451  ACCATATTGA CGCCAGGGAA AGACCGGAGT GGTTCTCTGC TTTTCCTCCA
11501  GAGGTCTGTG AGCACAGTTT GCTCAAGAAT AAGCAGACCT TTGGATGACA
                                  ↓ YF 17D iDNA end
11551  AACACAAAAC CACT - Ribozyme-Transcription Termination - Poly(A)
```

FIG. 9: Optimization of Distance Between the 3' End of the CMV Promoter and the 5' End of the TC-83 cDNA by Encapsidation Assay Using HA- or N-Vectors and the DNA c-Helpers

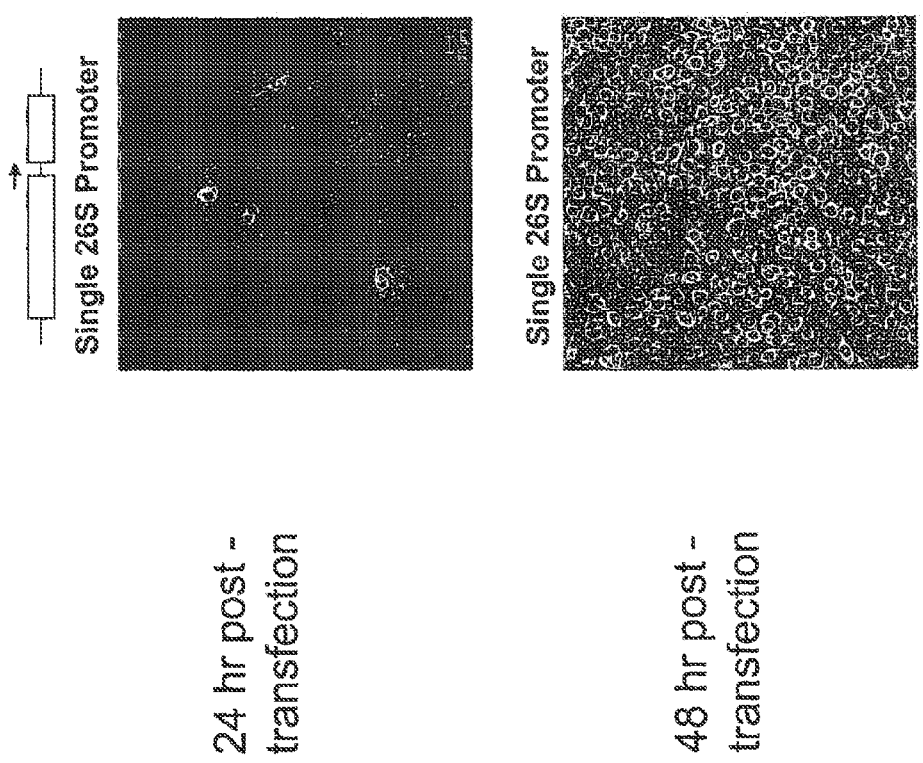
FIG. 10: Transfection of CHO Cells with TC-83 i-DNA #13-1 (wild-type)

FIG. 11: Transfection of CHO Cells with TC-83 i-DNA #12 (Double 26S Promoter)

FIG. 12: TC-83 Viruses Generated from Infectious Clones
In Vitro are Avirulent in BALB/c Mice

| TC-83 Clone | TC-83 Antigen Expression * | CPE** | Titer, PFU/ml | Virulence ***, Dead/Total |
|---|---|---|---|---|
| #12 | Yes | +++ | not detectable | NT |
| #13-1 | Yes | +++ | 7 x 10$^7$ | 0/10 |
| VEE Control | NT | NT | NT | 10/10 |

\* By immunofluorescence, 24 hr post transfection
\*\* Cytopathic effect, 96 hr post transfection
\*\*\* Determined in BALB/c mice NT, not tested in this experiment.
VEE Control, Trd strain

FIG. 13

| | |
|---|---|
| 5'aaagagctcTctggctaactagagaacccactggAtgggcggcgcatgagagaagcc3' | CM25/26 |
| 5'aaagagctcTctggctaactagagaacccacgAtgggcggcgcatgagagaagcc3' | CM23/24 |
| 5'aaagagctcTctggctaactagagaacccgAtgggcggcgcatgagagaagcc3' | CM21/22 |
| 5'aaagagctcTctggctaactagagaacgAtgggcggcgcatgagagaagcc3' | CM19/20 |
| 5'aaagagctcTctggctaactagagagAtgggcggcgcatgagagaagcc3' | CM17/18 |
| 5'aaagagctcTctggctaactagagAtgggcggcgcatgagagaagcc3' | CM15/16 |
| 5'aaagagctcTctggctaactagAtgggcggcgcatgagagaagcc3' | CM13/14 |
| 5'aaagagctcTctggctaactgAtgggcggcgcatgagagaagcc3' | CM12/13 |
| 5'aaagagctcTctggctaagAtgggcggcgcatgagagaagcc3' | CM10/11 |
| 5'aaagagctcTctggctgAtgggcggcgcatgagagaagcc3' | CM8/9 |
| | |
| 5'ttataggggcccctctcaggtagctgaatg3' | VEE26SR |

SEQUENCE LISTING

```
<160> NUMBER OF SEQ ID NOS: 3

<210> SEQ ID NO 1
<211> LENGTH: 12427
<212> TYPE: DNA
<213> ORGANISM: Venezuelan equine encephalitis virus

<400> SEQUENCE: 1
acaaggcaag gcttgaccga caattgcatg aagaatctgc ttagggttag gcgttttgcg      60
ctgcttcgcg atgtacgggc cagatatacg cgtggcgcgc ctgacattga ttattgacta     120
gttattaata gtaatcaatt acggggtcat tagttcatag cccatatatg gagttccgcg     180
ttacataact tacggtaaat ggcccgcctg gctgaccgcc caacgacccc cgcccattga     240
cgtcaataat gacgtatgtt cccatagtaa cgccaatagg gactttccat tgacgtcaat     300
gggtggagta tttacggtaa actgcccact tggcagtaca tcaagtgtat catatgccaa     360
gtacgccccc tattgacgtc aatgacggta aatggcccgc ctggcattat gcccagtaca     420
tgaccttatg ggactttcct acttggcagt acatctacgt attagtcatc gctattacca     480
tggtgatgcg gttttggcag tacatcaatg ggcgtggata gcggtttgac tcacggggat     540
ttccaagtct ccaccccatt gacgtcaatg ggagtttgtt ttggcaccaa aatcaacggg     600
actttccaaa atgtcgtaac aactccgccc cattgacgca aatgggcggt aggcgtgtac     660
ggtgggaggt ctatataagc agagctctct ggctaactag agataggcgg cgcatgagag     720
aagcccagac caattaccta cccaaaatgg agaaagttca cgttgacatc gaggaagaca     780
gcccattcct cagagctttg cagcggagct tcccgcagtt tgaggtagaa gccaagcagg     840
```

-continued

```
tcactgataa tgaccatgct aatgccagag cgttttcgca tctggcttca aaactgatcg    900
aaacggaggt ggacccatcc gacacgatcc ttgacattgg aagtgcgccc gcccgcagaa    960
tgtattctaa gcacaagtat cattgtatct gtccgatgag atgtgcggaa gatccggaca   1020
gattgtataa gtatgcaact aagctgaaga aaaactgtaa ggaataact gataaggaat    1080 tggacaagaa aatgaaggag ctcgccgccg tcatgagcga ccctgacctg gaaactgaga   1140
ctatgtgcct ccacgacgac gagtcgtgtc gctacgaagg gcaagtcgct gtttaccagg   1200
atgtatacgc ggttgacgga ccgacaagtc tctatcacca agccaataag ggagttagag   1260
tcgcctactg gataggcttt gacaccaccc cttttatgtt taagaacttg gctggagcat   1320
atccatcata ctctaccaac tgggccgacg aaaccgtgtt aacggctcgt aacataggcc   1380
tatgcagctc tgacgttatg gagcggtcac gtagagggat gtccattctt agaaagaagt   1440
atttgaaacc atccaacaat gttctattct ctgttggctc gaccatctac cacgagaaga   1500
gggacttact gaggagctgg cacctgccgt ctgtatttca cttacgtggc aagcaaaatt   1560
acacatgtcg gtgtgagact atagttagtt gcgacggta cgtcgttaaa agaatagcta    1620
tcagtccagg cctgtatggg aagccttcag gctatgctgc tacgatgcac cgcgagggat   1680
tcttgtgctg caaagtgaca gacacattga acggggagag ggtctctttt cccgtgtgca   1740
cgtatgtgcc agctacattg tgtgaccaaa tgactggcat actggcaaca gatgtcagtg   1800
cggacgacgc gcaaaaactg ctggttgggc tcaaccagcg tatagtcgtc aacggtcgca   1860
cccagagaaa caccaatacc atgaaaaatt accttttgcc cgtagtggcc caggcatttg   1920
ctaggtgggc aaaggaatat aaggaagatc aagaagatga aaggccacta ggactacgag   1980
atagacagtt agtcatgggg tgttgttggg cttttagaag gcacaagata acatctattt   2040
ataagcgccc ggatacccaa accatcatca aagtgaacag cgatttccac tcattcgtgc   2100
tgcccaggat aggcagtaac acattggaga tcgggctgag aacaagaatc aggaaaatgt   2160
tagaggagca caaggagccg tcacctctca ttaccgccga ggacgtacaa gaagctaagt   2220
gcgcagccga tgaggctaag gaggtgcgtg aagccgagga gttgcgcgca gctctaccac   2280 cttttggcagc tgatgttgag gagcccactc tggaagccga tgtcgacttg atgttacaag   2340 aggctgggc cggctcagtg gagacacctc gtggcttgat aaaggttacc agctacgctg    2400
gcgaggacaa gatcggctct tacgctgtgc tttctccgca ggctgtactc aagagtgaaa   2460
aattatcttg catccaccct ctcgctgaac aagtcatagt gataacacac tctggccgaa   2520
aagggcgtta tgccgtggaa ccataccatg gtaaagtagt ggtgccagag ggacatgcaa   2580
tacccgtcca ggactttcaa gctctgagtg aaagtgccac cattgtgtac aacgaacgtg   2640
agttcgtaaa caggtacctg caccatattg ccacacatgg aggagcgctg aacactgatg   2700
aagaatatta caaaactgtc aagcccagcg agcacgacgg cgaatacctg tacgacatcg   2760
acaggaaaca gtgcgtcaag aaagaactag tcactgggct agggctcaca ggcgagctgg   2820
tggatcctcc cttccatgaa ttcgcctacg agagtctgag aacacgacca gccgctcctt   2880
accaagtacc aaccataggg gtgtatggcg tgccaggatc aggcaagtct ggcatcatta   2940
aaagcgcagt caccaaaaaa gatctagtgg tgagcgccaa gaaagaaaac tgtgcagaaa   3000
ttataaggga cgtcaagaaa atgaaagggc tggacgtcaa tgccagaact gtggactcag   3060 tgctccttgaa tggatgcaaa caccccgtag agaccctgta tattgacgaa gcttttgctt   3120
gtcatgcagg tactctcaga gcgctcatag ccattataag acctaaaaag gcagtgctct   3180
gcggggatcc caaacagtgc ggttttttta acatgatgtg cctgaaagtg cattttaacc   3240
```

```
acgagatttg cacacaagtc ttccacaaaa gcatctctcg ccgttgcact aaatctgtga    3300
cttcggtcgt ctcaaccttg ttttacgaca aaaaaatgag aacgacgaat ccgaaagaga    3360
ctaagattgt gattgacact accggcagta ccaaacctaa gcaggacgat ctcattctca    3420
cttgtttcag agggtgggtg aagcagttgc aaatagatta caaaggcaac gaaataatga    3480
cggcagctgc ctctcaaggg ctgacccgta aggtgtgta tgccgttcgg tacaaggtga    3540
atgaaaatcc tctgtacgca cccacctcag aacatgtgaa cgtcctactg acccgcacgg    3600
aggaccgcat cgtgtggaaa acactagccg gcgacccatg gataaaaaca ctgactgcca    3660
agtaccctgg gaatttcact gccacgatag aggagtggca agcagagcat gatgccatca    3720
tgaggcacat cttggagaga ccggaccctaccgacgtctt ccagaataag gcaaacgtgt    3780
gttgggccaa ggctttagtg ccggtgctga agaccgctgg catagacatg accactgaac    3840
aatggaacac tgtggattat tttgaaacgg acaaagctca ctcagcagag atagtattga    3900
accaactatg cgtgaggttc tttggactcg atctggactc cggtctattt tctgcaccca    3960
ctgttccgtt atccattagg aataatcact gggataactc cccgtcgcct aacatgtacg    4020
ggctgaataa agaagtggtc cgtcagctct ctcgcaggta cccacaactg cctcgggcag    4080
ttgccactgg aagagtctat gacatgaaca ctggtacact gcgcaattat gatccgcgca    4140
taaacctagt acctgtaaac agaagactgc ctcatgcttt agtcctccac cataatgaac    4200
acccacagag tgacttttct tcattcgtca gcaaattgaa gggcagaact gtcctggtgg    4260
tcggggaaaa gttgtccgtc ccaggcaaaa tggttgactg gttgtcagac cggcctgagg    4320
ctaccttcag agctcggctg gatttaggca tcccaggtga tgtgcccaaa tatgacataa    4380
tatttgttaa tgtgaggacc ccatataaat accatcacta tcagcagtgt gaagaccatg    4440
ccattaagct tagcatgttg accaagaaag cttgtctgca tctgaatccc ggcggaacct    4500
gtgtcagcat aggttatggt tacgctgaca gggccagcga aagcatcatt ggtgctatag    4560
cgcggcagtt caagttttcc cgggtatgca aaccgaaatc ctcacttgaa gagacggaag    4620
ttctgttttgt attcattggg tacgatcgca aggcccgtac gcacaatcct tacaagcttt    4680
catcaacctt gaccaacatt tatacaggtt ccagactcca cgaagccgga tgtgcaccct    4740
catatcatgt ggtgcgaggg gatattgcca cggccaccga aggagtgatt ataaatgctg    4800
ctaacagcaa aggacaacct ggcggagggg tgtgcgagc ctgtataag aagttcccgg    4860
aaagcttcga tttacagccg atcgaagtag gaaaagcgcg actggtcaaa ggtgcagcta    4920
aacatatcat tcatgccgta ggaccaaact tcaacaaagt ttcggaggtt gaaggtgaca    4980
aacagttggc agaggcttat gagtccatcg ctaagattgt caacgataac aattacaagt    5040
cagtagcgat tccactgttg tccaccggca tcttttccgg gaacaaagat cgactaaccc    5100
aatcattgaa ccatttgctg acagctttag acaccactga tgcagatgta gccatatact    5160
gcagggacaa gaaatgggaa atgactctca aggaagcagt ggctaggaga gaagcagtgg    5220
aggagatatg catatccgac gactcttcag tgacagaacc tgatgcagag ctggtgaggg    5280
tgcatccgaa gagttctttg gctggaagga agggctacag cacaagcgat ggcaaaactt    5340
tctcatattt ggaagggacc aagtttcacc aggcggccaa ggatatagca gaaattaatg    5400
ccatgtggcc cgttgcaacg gaggccaatg agcaggtatg catgtatatc ctcggagaaa    5460
gcatgagcag tattaggtcg aaatgccccg tcgaagagtc ggaagcctcc acaccaccta    5520
gcacgctgcc ttgcttgtgc atccatgcca tgactccaga aagagtacag cgcctaaaag    5580
```

```
cctcacgtcc agaacaaatt actgtgtgct catcctttcc attgccgaag tatagaatca      5640
ctggtgtgca agatccaa tgctcccagc ctatattgtt ctcaccgaaa gtgcctgcgt        5700
atattcatcc aaggaagtat ctcgtggaaa caccaccggt agacgagact ccggagccat      5760
cggcagagaa ccaatccaca gaggggacac ctgaacaacc accacttata accgaggatg     5820
agaccaggac tagaacgcct gagccgatca tcatcgaaga ggaagaagag gatagcataa     5880
gtttgctgtc agatggcccg acccaccagg tgctgcaagt cgaggcagac attcacgggc     5940
cgccctctgt atctagctca tcctggtcca ttcctcatgc atccgacttt gatgtggaca    6000
gtttatccat acttgacacc ctggaggag ctagcgtgac cagcggggca acgtcagccg      6060
agactaactc ttacttcgca aagagtatgg agtttctggc gcgaccggtg cctgcgcctc    6120
gaacagtatt caggaaccct ccacatcccg ctccgcgcac aagaacaccg tcacttgcac    6180
ccagcagggc ctgctcgaga accagcctag ttccacccc gccaggcgtg aatagggtga      6240
tcactagaga ggagctcgag gcgcttaccc cgtcacgcac tcctagcagg tcggtctcga    6300
gaaccagcct ggtctccaac ccgccaggcg taaatagggt gattacaaga gaggagtttg     6360
aggcgttcgt agcacaacaa caatgacggt ttgatgcggg tgcatacatc ttttcctccg     6420
acaccggtca agggcattta caacaaaaat cagtaaggca acggtgcta tccgaagtgg      6480 tgttggagag gaccgaattg gagatttcgt atgccccgcg cctcgaccaa gaaaaagaag    6540
aattactacg caagaaatta cagttaaatc ccacacctgc taacagaagc agataccagt    6600
ccaggaaggt ggagaacatg aaagccataa cagctagacg tattctgcaa ggcctagggc    6660
attatttgaa ggcagaagga aaagtggagt gctaccgaac cctgcatcct gttcctttgt     6720
attcatctag tgtgaaccgt gcctttcaa gccccaaggt cgcagtggaa gcctgtaacg     6780
ccatgttgaa agagaacttt ccgactgtgg cttcttactg tattattcca gagtacgatg    6840
cctatttgga catggttgac ggagcttcat gctgcttaga cactgccagt ttttgccctg    6900
caaagctgcg cagcttttcca agaaacact cctatttgga acccacaata cgatcggcag    6960
tgccttcagc gatccagaac acgctccaga acgtcctggc agctgccaca aaaagaaatt    7020
gcaatgtcac gcaaatgaga gaattgcccg tattggattc ggcggccttt aatgtggaat    7080
gcttcaagaa atatgcgtgt aataatgaat attgggaaac gtttaaagaa aaccccatca    7140
ggcttactga agaaaacgtg gtaaattaca ttaccaaatt aaaaggacca aaagctgctg    7200 ctcttttgc gaagacacat aatttgaata tgttgcagga cataccaatg gacaggttg      7260 taatggactt aaagagagac gtgaaagtga ctccaggaac aaaacatact gaagaacggc    7320
ccaaggtaca ggtgatccag gctgccgatc cgctagcaac agcgtatctg tgcggaatcc    7380
accgagagct ggttaggaga ttaaatgcgg tcctgcttcc gaacattcat acactgtttg    7440
atatgtcggc tgaagacttt gacgctatta tagccgagca cttccagcct ggggattgtg    7500
ttctggaaac tgacatcgcg tcgtttgata aaagtgagga cgacgccatg gctctgaccg    7560
cgttaatgat tctggaagac ttaggtgtgg acgcagagct gttgacgctg attgaggcgg    7620
ctttcggcga atttcatca atacatttgc ccactaaaac taaatttaaa ttcggagcca    7680
tgatgaaatc tggaatgttc ctcacactgt ttgtgaacac agtcattaac attgtaatcg    7740
caagcagagt gttgagagaa cggctaaccg gatcaccatg tgcagcattc attggagatg    7800
acaatatcgt gaaaggagtc aaatcggaca aattaatggc agacaggtgc gccacctggt    7860
tgaatatgga agtcaagatt atagatgctg tggtgggcga gaaagcgcct tatttctgtg    7920
gagggtttat tttgtgtgac tccgtgaccg gcacagcgtg ccgtgtggca gacccccTaa    7980
```

```
aaaggctgtt taagcttggc aaacctctgg cagcagacga tgaacatgat gatgacagga    8040
gaagggcatt gcatgaagag tcaacacgct ggaaccgagt gggtattctt tcagagctgt    8100
gcaaggcagt agaatcaagg tatgaaaccg taggaacttc catcatagtt atggccatga    8160
ctactctagc tagcagtgtt aaatcattca gctacctgag aggggcccct ataactctct    8220
acggctaacc tgaatggact acgacatagt ctagtccgcc aagatgttcc cgttccagcc    8280
aatgtatccg atgcagccaa tgccctatcg caacccgttc gcggcccgc gcaggccctg     8340 gttccccaga accgaccctt ttctggcgat gcaggtgcag gaattaaccc gctcgatggc    8400
taacctgacg ttcaagcaac gccgggacgc gccacctgag gggccatccg ctaagaaacc    8460
gaagaaggag gcctcgcaaa acagaaagg gggaggccaa gggaagaaga agaagaacca     8520
agggaagaag aaggctaaga cagggccgcc taatccgaag gcacagaatg gaaacaagaa    8580
gaagaccaac aagaaaccag gcaagagaca gcgcatggtc atgaaattgg aatctgacaa    8640
gacgttccca atcatgttgg aagggaagat aaacggctac gcttgtgtgg tcggagggaa    8700
gttattcagg ccgatgcatg tggaaggcaa gatcgacaac gacgttctgg ccgcgcttaa    8760
gacgaagaaa gcatccaaat acgatcttga gtatgcagat gtgccacaga acatgcgggc    8820
cgatacattc aaatacaccc atgagaaacc ccaaggctat tacagctggc atcatggagc    8880
agtccaatat gaaatgggc gtttcacggt gccgaaagga gttggggcca agggagacag     8940
cggacgaccc attctggata ccagggacg ggtggtcgct attgtgctgg gaggtgtgaa     9000
tgaaggatct aggacagccc tttcagtcgt catgtggaac gagaagggag ttaccgtgaa    9060
gtatactccg gagaactgcg agcaatggtc actagtgacc accatgtgtc tgctcgccaa    9120
tgtgacgttc ccatgtgctc aaccaccaat ttgctacgac agaaaaccag cagagacttt    9180
ggccatgctc agcgttaacg ttgacaaccc gggctacgat gagctgctgg aagcagctgt    9240
taagtgcccc ggaaggaaaa ggagatccac cgaggagctg tttaatgagt ataagctaac    9300
gcgcccttac atggccagat gcatcagatg tgcagttggg agctgccata gtccaatagc    9360
aatcgaggca gtaaagagcg acgggcacga cggttatgtt agacttcaga cttcctcgca    9420
gtatggcctg gattcctccg gcaacttaaa gggcaggacc atgcggtatg acatgcacgg    9480
gaccattaaa gagataccac tacatcaagt gtcactctat acatctcgcc cgtgtcacat    9540
tgtggatggg cacggttatt tcctgcttgc caggtgcccg gcaggggact ccatcaccat    9600
ggaatttaag aaagattccg tcagacactc ctgctcggtg ccgtatgaag tgaaatttaa    9660
tcctgtaggc agagaactct atactcatcc cccagaacac ggagtagagc aagcgtgcca    9720
agtctacgca catgatgcac agaacagagg agcttatgtc gagatgcacc tcccgggctc    9780
agaagtggac agcagtttgg tttccttgag cggcagttca gtcaccgtga cacctcctga    9840
tgggactagc gccctggtgg aatgcgagtg tggcggcaca aagatctccg agaccatcaa    9900
caagacaaaa cagttcagcc agtgcacaaa gaaggagcag tgcagagcat atcggctgca    9960
gaacgataag tgggtgtata ttctgacaa actgcccaaa gcagcgggag ccaccttaaa    10020
aggaaaactg catgtcccat tcttgctggc agacggcaaa tgcaccgtgc ctctagcacc    10080
agaacctatg ataaccttcg gtttcagatc agtgtcactg aaactgcacc ctaagaatcc    10140
cacatatcta atcacccgcc aacttgctga tgagcctcac tacacgcacg agctcatatc    10200
tgaaccagct gttaggaatt ttaccgtcac cgaaaaaggg tgggagtttg tatggggaaa    10260
ccacccgccg aaaaggtttt gggcacagga aacagcaccc ggaaatccac atgggctacc    10320
```

```
gcacgaggtg ataactcatt attaccacag atacccctatg tccaccatcc tgggtttgtc    10380
aatttgtgcc gccattgcaa ccgtttccgt tgcagcgtct acctggctgt tttgcagatc    10440
tagagttgcg tgcctaactc cttaccggct aacacctaac gctaggatac cattttgtct    10500
ggctgtgctt tgctgcgccc gcactgcccg ggccgagacc acctgggagt ccttggatca    10560
cctatggaac aataaccaac agatgttctg gattcaattg ctgatccctc tggccgcctt    10620
gatcgtagtg actcgcctgc tcaggtgcgt gtgctgtgtc gtgcctttt tagtcatggc     10680 cggcgccgca ggcgccggcg cctacgagca cgcgaccacg atgccgagcc aagcgggaat    10740
ctcgtataac actatagtca acagagcagg ctacgcacca ctccctatca gcataacacc    10800
aacaaagatc aagctgatac ctacagtgaa cttggagtac gtcacctgcc actacaaaac    10860
aggaatggat tcaccagcca tcaaatgctg cggatctcag gaatgcactc caacttacag    10920
gcctgatgaa cagtgcaaag tcttcacagg ggtttacccg ttcatgtggg gtggtgcata    10980 ttgctttttgc gacactgaga cacccaagt cagcaaggcc tacgtaatga aatctgacga    11040
ctgccttgcg gatcatgctg aagcatataa agcgcacaca gcctcagtgc aggcgttcct    11100
caacatcaca gtgggagaac actctattgt gactaccgtg tatgtgaatg gagaaactcc    11160
tgtgaatttc aatggggtca aataactgc aggtccgctt tccacagctt ggacacctt     11220 tgatcgcaaa atcgtgcagt atgccgggga gatctataat tatgatttc ctgagtatgg    11280 ggcaggacaa ccaggagcat ttggagatat acaatccaga acagtctcaa gctctgatct    11340
gtatgccaat accaacctag tgctgcagag acccaaagca ggagcgatcc acgtgccata    11400
cactcaggca ccttcgggtt tgagcaatg gaagaaagat aaagctccat cattgaaatt    11460
taccgcccct ttcggatgcg aaatatatac aaaccccatt cgcgccgaaa actgtgctgt    11520
agggtcaatt ccattagcct ttgacattcc cgacgccttg ttcaccaggg tgtcagaaac    11580
accgacactt tcagcggccg aatgcactct taacgagtgc gtgtattctt ccgactttgg    11640
tgggatcgcc acggtcaagt actcggccag caagtcaggc aagtgcgcag tccatgtgcc    11700
atcagggact gctaccctaa agaagcagc agtcgagcta accgagcaag gtcggcgac    11760 tatccatttc tcgaccgcaa atatccaccc ggagttcagg ctccaaatat gcacatcata    11820
tgttacgtgc aaaggtgatt gtcacccccc gaaagaccat attgtgacac ccctcagta    11880 tcacgcccaa acatttacag ccgcggtgtc aaaaacgcg tggacgtggt taacatccct    11940
gctgggagga tcagccgtaa ttattataat tggcttggtg ctggctacta ttgtggccat    12000
gtacgtgctg accaaccaga acataattg aatacagcag caattggcaa gctgcttaca    12060
tagaactcgc ggcgattggc atgccgcctt aaaattttta tttattttt tcttttcttt     12120 tccgaatcgg atttgtttt taatatttca aaaaaaaaa aaaaaaaaa gggtacgcgg       12180 ccgccactgt gctggatatc tgcagaattc caccacactg gactagtgga tcagcttaag    12240
tttaaaccgc tgatcagcct cgactgtgcc ttctagttgc cagccatctg ttgtttgccc    12300
ctcccccgtg ccttccttga ccctggaagg tgccactccc actgtccttt cctaataaaa    12360
tgaggaaatt gcatcgcatt gtctgagtag gtgtcattct attctggggg gtggggtggg    12420
gcaggac                                                              12427

<210> SEQ ID NO 2
<211> LENGTH: 12594
<212> TYPE: DNA
<213> ORGANISM: Venezuelan equine encephalitis virus

<400> SEQUENCE: 2
```

```
acaaggcaag gcttgaccga caattgcatg aagaatctgc ttagggttag gcgttttgcg      60
ctgcttcgcg atgtacgggc cagatatacg cgtggcgcgc ctgacattga ttattgacta     120
gttattaata gtaatcaatt acggggtcat tagttcatag cccatatatg gagttccgcg     180
ttacataact tacggtaaat ggcccgcctg gctgaccgcc caacgacccc cgcccattga     240
cgtcaataat gacgtatgtt cccatagtaa cgccaatagg gactttccat tgacgtcaat     300
gggtggagta tttacggtaa actgcccact tggcagtaca tcaagtgtat catatgccaa     360
gtacgccccc tattgacgtc aatgacggta atggcccgc ctggcattat gcccagtaca     420
tgaccttatg ggactttcct acttggcagt acatctacgt attagtcatc gctattacca     480
tggtgatgcg gttttggcag tacatcaatg ggcgtggata gcggtttgac tcacggggat     540
ttccaagtct ccaccccatt gacgtcaatg ggagtttgtt ttggcaccaa aatcaacggg     600
actttccaaa atgtcgtaac aactccgccc cattgacgca aatgggcggt aggcgtgtac     660
ggtgggaggt ctatataagc agagctctct ggctaactag agataggcgg cgcatgagag     720
aagcccagac caattaccta cccaaaatgg agaaagttca cgttgacatc gaggaagaca     780
gcccattcct cagagctttg cagcggagct tcccgcagtt tgaggtagaa gccaagcagg     840
tcactgataa tgaccatgct aatgccagag cgttttcgca tctggcttca aaactgatcg     900
aaacggaggt ggacccatcc gacacgatcc ttgacattgg aagtgcgccc gcccgcagaa     960
tgtattctaa gcacaagtat cattgtatct gtccgatgag atgtgcggaa gatccggaca    1020
gattgtataa gtatgcaact aagctgaaga aaaactgtaa ggaataact gataaggaat    1080
tggacaagaa aatgaaggag ctcgccgccg tcatgagcga ccctgacctg gaaactgaga    1140
ctatgtgcct ccacgacgac gagtcgtgtc gctacgaagg gcaagtcgct gtttaccagg    1200
atgtatacgc ggttgacgga ccgacaagtc tctatcacca agccaataag ggagttagag    1260
tcgcctactg gataggcttt gacaccaccc cttttatgtt taagaacttg gctggagcat    1320
atccatcata ctctaccaac tgggccgacg aaaccgtgtt aacggctcgt aacataggcc    1380
tatgcagctc tgacgttatg gagcggtcac gtagagggat gtccattctt agaaagaagt    1440
atttgaaacc atccaacaat gttctattct ctgttggctc gaccatctac cacgagaaga    1500
gggacttact gaggagctgg cacctgccgt ctgtatttca cttacgtggc aagcaaaatt    1560
acacatgtcg gtgtgagact atagttagtt gcgacggta cgtcgttaaa gaatagcta    1620
tcagtccagg cctgtatggg aagccttcag gctatgctgc tacgatgcac cgcgagggat    1680
tcttgtgctg caaagtgaca gacacattga acggggagag ggtctctttt cccgtgtgca    1740
cgtatgtgcc agctacattg tgtgaccaaa tgactggcat actggcaaca gatgtcagtg    1800
cggacgacgc gcaaaaactg ctggttgggc tcaaccagcg tatagtcgtc aacggtcgca    1860
cccagagaaa caccaatacc atgaaaaatt accttttgcc cgtagtggcc caggcatttg    1920
ctaggtgggc aaaggaatat aaggaagatc aagaagatga aaggccacta ggactacgag    1980
atagacagtt agtcatgggg tgttgttggg ctttttagaag gcacaagata acatctattt    2040
ataagcgccc ggatacccaa accatcatca aagtgaacag cgatttccac tcattcgtgc    2100
tgcccaggat aggcagtaac acattggaga tcgggctgag aacaagaatc aggaaaatgt    2160
tagaggagca caaggagccg tcacctctca ttaccgccga ggacgtacaa gaagctaagt    2220
gcgcagccga tgaggctaag gaggtgcgtg aagccgagga gttgcgcgca gctctaccac    2280
ctttggcagc tgatgttgag gagcccactc tggaagccga tgtcgacttg atgttacaag    2340
```

```
aggctggggc cggctcagtg gagacacctc gtggcttgat aaaggttacc agctacgctg    2400
gcgaggacaa gatcggctct tacgctgtgc tttctccgca ggctgtactc aagagtgaaa    2460
aattatcttg catccaccct ctcgctgaac aagtcatagt gataacacac tctggccgaa    2520
aagggcgtta tgccgtggaa ccataccatg gtaaagtagt ggtgccagag ggacatgcaa    2580
tacccgtcca ggactttcaa gctctgagtg aaagtgccac cattgtgtac aacgaacgtg    2640
agttcgtaaa caggtacctg caccatattg ccacacatgg aggagcgctg aacactgatg    2700
aagaatatta caaaactgtc aagcccagcg agcacgacgg cgaatacctg tacgacatcg    2760
acaggaaaca gtgcgtcaag aaagaactag tcactgggct agggctcaca ggcgagctgg    2820
tggatcctcc cttccatgaa ttcgcctacg agagtctgag aacacgacca gccgctcctt    2880
accaagtacc aaccataggg gtgtatggcg tgccaggatc aggcaagtct ggcatcatta    2940
aaagcgcagt caccaaaaaa gatctagtgg tgagcgccaa gaaagaaaac tgtgcagaaa    3000
ttataaggga cgtcaagaaa atgaaagggc tggacgtcaa tgccagaact gtggactcag    3060
tgctcttgaa tggatgcaaa caccccgtag agaccctgta tattgacgaa gcttttgctt    3120
gtcatgcagg tactctcaga gcgctcatag ccattataag acctaaaaag gcagtgctct    3180
gcggggatcc caaacagtgc ggttttttta acatgatgtg cctgaaagtg cattttaacc    3240
acgagatttg cacacaagtc ttccacaaaa gcatctctcg ccgttgcact aaatctgtga    3300
cttcggtcgt ctcaaccttg ttttacgaca aaaaatgag aacgacgaat ccgaaagaga    3360
ctaagattgt gattgacact accggcagta ccaaacctaa gcaggacgat ctcattctca    3420
cttgtttcag agggtgggtg aagcagttgc aaatagatta caaaggcaac gaaataatga    3480
cggcagctgc ctctcaaggg ctgacccgta aggtgtgta tgccgttcgg tacaaggtga    3540
atgaaaatcc tctgtacgca cccacctcag aacatgtgaa cgtcctactg acccgcacgg    3600
aggaccgcat cgtgtggaaa acactagccg gcgacccatg gataaaaaca ctgactgcca    3660
agtaccctgg gaatttcact gccacgatag aggagtggca agcagagcat gatgccatca    3720
tgaggcacat cttggagaga ccggacccta ccgacgtctt ccagaataag gcaaacgtgt    3780
gttgggccaa ggctttagtg ccggtgctga agaccgctgg catagacatg accactgaac    3840
aatggaacac tgtggattat ttgaaacgg acaaagctca ctcagcagag atagtattga    3900
accaactatg cgtgaggttc tttggactcg atctggactc cggtctattt tctgcaccca    3960
ctgttccgtt atccattagg aataatcact gggataactc cccgtcgcct aacatgtacg    4020
ggctgaataa agaagtggtc cgtcagctct ctcgcaggta cccacaactg cctcgggcag    4080
ttgccactgg aagagtctat gacatgaaca ctggtacact gcgcaattat gatccgcgca    4140
taaacctagt acctgtaaac agaagactgc ctcatgcttt agtcctccac cataatgaac    4200
acccacagag tgacttttct tcattcgtca gcaaattgaa gggcagaact gtcctggtgg    4260
tcggggaaaa gttgtccgtc ccaggcaaaa tggttgactg gttgtcagac ggcctgaggg    4320
ctaccttcag agctcggctg gatttaggca tcccaggtga tgtgcccaaa tatgacataa    4380
tatttgttaa tgtgaggacc ccatataaat accatcacta tcagcagtgt gaagaccatg    4440
ccattaagct tagcatgttg accaagaaag cttgtctgca tctgaatccc ggcggaacct    4500
gtgtcagcat aggttatggt tacgctgaca gggccagcga agcatcatt ggtgctatag    4560 cgcggcagtt caagttttcc cgggtatgca aaccgaaatc ctcacttgaa gagacggaag    4620
ttctgtttgt attcattggg tacgatcgca aggcccgtac gcacaatcct tacaagcttt    4680
catcaacctt gaccaacatt tatacaggtt ccagactcca cgaagccgga tgtgcaccct    4740
```

```
catatcatgt ggtgcgaggg gatattgcca cggccaccga aggagtgatt ataaatgctg    4800
ctaacagcaa aggacaacct ggcggagggg tgtgcggagc gctgtataag aagttcccgg    4860
aaagcttcga tttacagccg atcgaagtag gaaaagcgcg actggtcaaa ggtgcagcta    4920
aacatatcat tcatgccgta ggaccaaact tcaacaaagt ttcggaggtt gaaggtgaca    4980
aacagttggc agaggcttat gagtccatcg ctaagattgt caacgataac aattacaagt    5040
cagtagcgat tccactgttg tccaccggca tcttttccgg gaacaaagat cgactaaccc    5100
aatcattgaa ccatttgctg acagctttag acaccactga tgcagatgta gccatatact    5160
gcagggacaa gaaatgggaa atgactctca aggaagcagt ggctaggaga gaagcagtgg    5220
aggagatatg catatccgac gactcttcag tgacagaacc tgatgcagag ctggtgaggg    5280
tgcatccgaa gagttctttg gctggaagga agggctacag cacaagcgat ggcaaaactt    5340
tctcatattt ggaagggacc aagtttcacc aggcggccaa ggatatagca gaaattaatg    5400
ccatgtggcc cgttgcaacg gaggccaatg agcaggtatg catgtatatc ctcggagaaa    5460
gcatgagcag tattaggtcg aaatgccccg tcgaagagtc ggaagcctcc acaccaccta    5520
gcacgctgcc ttgcttgtgc atccatgcca tgactccaga aagagtacag cgcctaaaag    5580
cctcacgtcc agaacaaatt actgtgtgct catccttttcc attgccgaag tatagaatca    5640
ctggtgtgca gaagtccaa tgctcccagc ctatattgtt ctcaccgaaa gtgcctgcgt    5700
atattcatcc aaggaagtat ctcgtggaaa caccaccggt agacgagact ccggagccat    5760
cggcagagaa ccaatccaca gaggggacac ctgaacaacc accacttata accgaggatg    5820
agaccaggac tagaacgcct gagccgatca tcatcgaaga ggaagaagag gatagcataa    5880
gtttgctgtc agatggcccg acccaccagg tgctgcaagt cgaggcagac attcacgggc    5940
cgccctctgt atctagctca tcctggtcca ttcctcatgc atccgacttt gatgtggaca    6000
gtttatccat acttgacacc ctggaggag ctagcgtgac cagcggggca acgtcagccg    6060
agactaactc ttacttcgca aagagtatgg agtttctggc gcgaccggtg cctgcgcctc    6120
gaacagtatt caggaaccct ccacatcccg ctccgcgcac aagaacaccg tcacttgcac    6180
ccagcagggc ctgctcgaga accagcctag ttttccacccc gccaggcgtg aatagggtga    6240
tcactagaga ggagctcgag gcgcttaccc cgtcacgcac tcctagcagg tcggtctcga    6300
gaaccagcct ggtctccaac ccgccaggcg taaataggt gattacaaga gaggagtttg    6360
aggcgttcgt agcacaacaa caatgacggt ttgatgcggg tgcatacatc ttttcctccg    6420
acaccggtca agggcattta caacaaaaat cagtaaggca aacggtgcta tccgaagtgg    6480
tgttggagag gaccgaattg gagatttcgt atgccccgcg cctcgaccaa gaaaagaag    6540 aattactacg caagaaatta cagttaaatc ccacacctgc taacagaagc agataccagt    6600
ccaggaaggt ggagaacatg aaagccataa cagctagacg tattctgcaa ggcctagggc    6660
attatttgaa ggcagaagga aaagtggagt gctaccgaac cctgcatcct gttcctttgt    6720
attcatctag tgtgaaccgt gcctttttcaa gccccaaggt cgcagtggaa gcctgtaacg    6780
ccatgttgaa agagaacttt ccgactgtgg cttcttactg tattattcca gagtacgatg    6840
cctatttgga catggttgac ggagcttcat gctgcttaga cactgccagt ttttgccctg    6900
caaagctgcg cagctttcca agaaacact cctatttgga acccacaata cgatcggcag    6960
tgccttcagc gatccagaac acgctccaga acgtcctggc agctgccaca aaaagaaatt    7020
gcaatgtcac gcaaatgaga gaattgcccg tattggattc ggcggccttt aatgtggaat    7080
```

```
gcttcaagaa atatgcgtgt aataatgaat attgggaaac gtttaaagaa aaccccatca    7140
ggcttactga agaaaacgtg gtaaattaca ttaccaaatt aaaaggacca aaagctgctg    7200 ctcttttttgc gaagacacat aatttgaata tgttgcagga cataccaatg gacaggtttg    7260
taatggactt aaagagagac gtgaaagtga ctccaggaac aaaacatact gaagaacggc    7320
ccaaggtaca ggtgatccag gctgccgatc cgctagcaac agcgtatctg tgcggaatcc    7380
accgagagct ggttaggaga ttaaatgcgg tcctgcttcc gaacattcat acactgtttg    7440
atatgtcggc tgaagacttt gacgctatta tagccgagca cttccagcct ggggattgtg    7500
ttctggaaac tgcatcgcg tcgtttgata aaagtgagga cgacgccatg gctctgaccg    7560
cgttaatgat tctggaagac ttaggtgtgg acgcagagct gttgacgctg attgaggcgg    7620
ctttcggcga aatttcatca atacatttgc ccactaaaac taaatttaaa ttcggagcca    7680
tgatgaaatc tggaatgttc ctcacactgt ttgtgaacac agtcattaac attgtaatcg    7740
caagcagagt gttgagagaa cggctaaccg gatcaccatg tgcagcattc attggagatg    7800
acaatatcgt gaaaggagtc aaatcggaca aattaatggc agacaggtgc gccacctggt    7860
tgaatatgga agtcaagatt atagatgctg tggtgggcga gaaagcgcct tatttctgtg    7920
gagggtttat tttgtgtgac tccgtgaccg gcacagcgtg ccgtgtggca gacccccctaa    7980 aaaggctgtt taagcttggc aaacctctgg cagcagacga tgaacatgat gatgacagga    8040
gaagggcatt gcatgaagag tcaacacgct ggaaccgagt gggtattctt tcagagctgt    8100
gcaaggcagt agaatcaagg tatgaaaccg taggaacttc catcatagtt atggccatga    8160
ctactctagc tagcagtgtt aaatcattca gctacctgag aggggcccct ataactctct    8220
acggctaacc tgaatggact acgacatagt ctagtccgcc aagatgttcc cgttccagcc    8280
aatgtatccg atgcagccaa tgccctatcg caacccgttc gcggcccccgc gcaggccctg    8340 gttccccaga accgacccct ttctggcgat gcaggtgcag gaattaaccc gctcgatggc    8400
taacctgacg ttcaagcaac gccgggacgc gccacctgag gggccatccg ctaagaaacc    8460
gaagaaggag gcctcgcaaa aacagaaagg gggaggccaa gggaagaaga agaagaacca    8520
agggaagaag aaggctaaga cagggccgcc taatccgaag gcacagaatg gaaacaagaa    8580
gaagaccaac aagaaaccag gcaagagaca gcgcatggtc atgaaattgg aatctgacaa    8640
gacgttccca atcatgttgg aagggaagat aaacggctac gcttgtgtgg tcggagggaa    8700
gttattcagg ccgatgcatg tggaaggcaa gatcgacaac gacgttctgg ccgcgcttaa    8760
gacgaagaaa gcatccaaat acgatcttga gtatgcagat gtgccacaga acatgcgggc    8820
cgatacattc aaatacaccc atgagaaacc ccaaggctat tacagctggc atcatggagc    8880
agtccaatat gaaaatgggc gtttcacggt gccgaaagga gttggggcca agggagacag    8940
cggacgaccc attctggata accagggacg ggtggtcgct attgtgctgg gaggtgtgaa    9000
tgaaggatct aggacagccc tttcagtcgt catgtggaac gagaagggag ttaccgtgaa    9060
gtatactccg gagaactgcg agcaatggtg actagtgacc accatgtgtc tgctcgccaa    9120
tgtgacgttc ccatgtgctc aaccaccaat ttgctacgac agaaaaccag cagagacttt    9180
ggccatgctc agcgttccta taactctcta cggctaacct gaatggacta cgacatagtc    9240
tagtccgcca agatgtcact agtgaccacc atgtgtctgc tcgccaatgt gacgttccca    9300
tgtgctcaac caccaatttg ctacgacaga aaaccagcag agactttggc catgctcagc    9360
gttaacgttg acaacccggg ctacgatgag ctgctggaag cagctgttaa gtgccccgga    9420
aggaaaagga gatccaccga ggagctgttt aatgagtata agctaacgcg cccttacatg    9480
```

```
gccagatgca tcagatgtgc agttgggagc tgccatagtc caatagcaat cgaggcagta   9540
aagagcgacg ggcacgacgg ttatgttaga cttcagactt cctcgcagta tggcctggat   9600
tcctccggca acttaaaggg caggaccatg cggtatgaca tgcacgggac cattaaagag   9660
ataccactac atcaagtgtc actctataca tctcgcccgt gtcacattgt ggatgggcac   9720
ggttatttcc tgcttgccag gtgcccggca ggggactcca tcaccatgga atttaagaaa   9780
gattccgtca gacactcctg ctcggtgccg tatgaagtga aatttaatcc tgtaggcaga   9840
gaactctata ctcatccccc agaacacgga gtagagcaag cgtgccaagt ctacgcacat   9900
gatgcacaga acagaggagc ttatgtcgag atgcacctcc cgggctcaga agtggacagc   9960
agtttggttt ccttgagcgg cagttcagtc accgtgacac ctcctgatgg gactagcgcc  10020
ctggtggaat gcgagtgtgg cggcacaaag atctccgaga ccatcaacaa gacaaaacag  10080
ttcagccagt gcacaaagaa ggagcagtgc agagcatatc ggctgcagaa cgataagtgg  10140
gtgtataatt ctgacaaact gcccaaagca gcgggagcca ccttaaaagg aaaactgcat  10200
gtcccattct tgctggcaga cggcaaatgc accgtgcctc tagcaccaga acctatgata  10260
accttcggtt tcagatcagt gtcactgaaa ctgcaccctca agaatcccac atatctaatc  10320
acccgccaac ttgctgatga gcctcactac acgcacgagc tcatatctga accagctgtt  10380
aggaatttta ccgtcaccga aaaagggtgg gagtttgtat ggggaaacca cccgccgaaa  10440
aggttttggg cacaggaaac agcacccgga aatccacatg ggctaccgca cgaggtgata  10500
actcattatt accacagata ccctatgtcc accatcctgg gtttgtcaat ttgtgccgcc  10560
attgcaaccg tttccgttgc agcgtctacc tggctgtttt gcagatctag agttgcgtgc  10620
ctaactcctt accggctaac acctaacgct aggataccat tttgtctggc tgtgcttttgc 10680 tgcgcccgca ctgccgggc cgagaccacc tgggagtcct tggatcacct atggaacaat  10740
aaccaacaga tgttctggat tcaattgctg atccctctgg ccgccttgat cgtagtgact  10800
cgcctgctca ggtgcgtgtg ctgtgtcgtg ccttttttag tcatggccgg cgccgcaggc  10860
gccggcgcct acgagcacgc gaccacgatg ccgagccaag cgggaatctc gtataacact  10920
atagtcaaca gagcaggcta cgcaccactc cctatcagca taacaccaac aaagatcaag  10980
ctgataccta cagtgaactt ggagtacgtc acctgccact acaaaacagg aatggattca  11040
ccagccatca aatgctgcgg atctcaggaa tgcactccaa cttacaggcc tgatgaacag  11100
tgcaaagtct tcacaggggt ttacccgttc atgtggggtg gtgcatattg cttttgcgac  11160
actgagaaca cccaagtcag caaggcctac gtaatgaaat ctgacgactg ccttgcggat  11220
catgctgaag catataaagc gcacacagcc tcagtgcagg cgttcctcaa catcacagtg  11280
ggagaacact ctattgtgac taccgtgtat gtgaatggag aaactcctgt gaatttcaat  11340
ggggtcaaaa taactgcagg tccgctttcc acagcttgga cacccctttga tcgcaaaatc  11400 gtgcagtatg ccggggagat ctataattat gattttcctg agtatgggc aggacaacca  11460 ggagcatttg gagatataca atccagaaca gtctcaagct ctgatctgta tgccaatacc  11520
aacctagtgc tgcagagacc caaagcagga gcgatccacg tgccatacac tcaggcacct  11580
tcgggttttg agcaatggaa gaaagataaa gctccatcat tgaaatttac cgcccctttc  11640
ggatgcgaaa tatatacaaa ccccattcgc gccgaaaact gtgctgtagg gtcaattcca  11700
ttagcctttg acattcccga cgccttgttc accagggtgt cagaaacacc gacactttca  11760
gcggccgaat gcactcttaa cgagtgcgtg tattcttccg actttggtgg gatcgccacg  11820
```

| | | | | |
|---|---|---|---|---|
| gtcaagtact | cggccagcaa | gtcaggcaag | tgcgcagtcc | atgtgccatc | agggactgct | 11880 |
| accctaaaag | aagcagcagt | cgagctaacc | gagcaagggt | cggcgactat | ccatttctcg | 11940 |
| accgcaaata | tccacccgga | gttcaggctc | caaatatgca | catcatatgt | tacgtgcaaa | 12000 |
| ggtgattgtc | accccccgaa | agaccatatt | gtgacacacc | ctcagtatca | cgcccaaaca | 12060 |
| tttacagccg | cggtgtcaaa | aaccgcgtgg | acgtggttaa | catccctgct | gggaggatca | 12120 |
| gccgtaatta | ttataattgg | cttggtgctg | ctactattg | tggccatgta | cgtgctgacc | 12180 |
| aaccagaaac | ataattgaat | acagcagcaa | ttggcaagct | gcttacatag | aactcgcggc | 12240 |
| gattggcatg | ccgccttaaa | attttttattt | tattttttct | tttcttttcc | gaatcggatt | 12300 |
| ttgttttttaa | tatttcaaaa | aaaaaaaaaa | aaaaaagggg | tacgcggccg | ccactgtgct | 12360 |
| ggatatctgc | agaattccac | cacactgac | tagtggatca | gcttaagttt | aaaccgctga | 12420 |
| tcagcctcga | ctgtgccttc | tagttgccag | ccatctgttg | tttgcccctc | cccgtgcct | 12480 |
| tccttgaccc | tggaaggtgc | cactcccact | gtcctttcct | aataaaatga | ggaaattgca | 12540 |
| tcgcattgtc | tgagtaggtg | tcattctatt | ctggggggtg | ggtgggga | ggac | 12594 |

<210> SEQ ID NO 3
<211> LENGTH: 11564
<212> TYPE: DNA
<213> ORGANISM: Yellow fever virus

<400> SEQUENCE: 3

| | | | | | |
|---|---|---|---|---|---|
| acaaggcaag | gcttgaccga | caattgcatg | aagaatctgc | ttagggttag | gcgttttgcg | 60 |
| ctgcttcgcg | atgtacgggc | cagatatacg | cgtggcgcgc | ctgacattga | ttattgacta | 120 |
| gttattaata | gtaatcaatt | acggggtcat | tagttcatag | cccatatatg | gagttccgcg | 180 |
| ttacataact | tacggtaaat | ggcccgcctg | gctgaccgcc | caacgacccc | cgcccattga | 240 |
| cgtcaataat | gacgtatgtt | cccatagtaa | cgccaatagg | gactttccat | tgacgtcaat | 300 |
| gggtggagta | tttacggtaa | actgcccact | tggcagtaca | tcaagtgtat | catatgccaa | 360 |
| gtacgccccc | tattgacgtc | aatgacggta | aatggcccgc | ctggcattat | gcccagtaca | 420 |
| tgaccttatg | ggactttcct | acttggcagt | acatctacgt | attagtcatc | gctattacca | 480 |
| tggtgatgcg | gttttggcag | tacatcaatg | ggcgtggata | gcggtttgac | tcacggggat | 540 |
| ttccaagtct | ccaccccatt | gacgtcaatg | ggagtttgtt | ttggcaccaa | aatcaacggg | 600 |
| actttccaaa | atgtcgtaac | aactccgccc | cattgacgca | aatgggcggt | aggcgtgtac | 660 |
| ggtgggaggt | ctatataagc | agagctctct | ggctaactag | agagtaaatc | ctgtgtgcta | 720 |
| attgaggtgc | attggtctgc | aaatcgagtt | gctaggcaat | aaacacattt | ggattaatttt | 780 |
| taatcgttcg | ttgagcgatt | agcagagaac | tgaccagaac | atgtctggtc | gtaaagctca | 840 |
| gggaaaaacc | ctgggcgtca | atatggtacg | acgaggagtt | cgctccttgt | caaacaaaat | 900 |
| aaaacaaaaa | acaaaacaaa | ttggaaacag | acctggaccct | tcaagaggtg | ttcaaggatt | 960 |
| tatcttttc | ttttgttca | acatttttgac | tggaaaaaag | atcacagccc | acctaaagag | 1020 |
| gttgtggaaa | atgctggacc | caagacaagg | cttggctgtt | ctaaggaaag | tcaagagagt | 1080 |
| ggtggccagt | tgatgagag | gattgtcctc | aaggaaacgc | cgttcccatg | atgttctgac | 1140 |
| tgtgcaattc | ctaattttgg | gaatgctgtt | gatgacgggt | ggagtgaccct | tggtgcggaa | 1200 |
| aaacagatgg | ttgctcctaa | atgtgacatc | tgaggacctc | gggaaaacat | tctctgtggg | 1260 |
| cacaggcaac | tgcacaacaa | acattttgga | agccaagtac | tggtgcccag | actcaatgga | 1320 |
| atacaactgt | cccaatctca | gtccaagaga | ggagccagat | gacattgatt | gctggtgcta | 1380 |

```
tggggtggaa aacgttagag tcgcatatgg taagtgtgac tcagcaggca ggtctaggag    1440
gtcaagaagg gccattgact tgcctacgca tgaaaaccat ggtttgaaga cccggcaaga    1500
aaaatggatg actggaagaa tgggtgaaag gcaactccaa aagattgaga gatggttcgt    1560
gaggaacccc ttttttgcag tgacggctct gaccattgcc taccttgtgg gaagcaacat    1620
gacgcaacga gtcgtgattg ccctactggt cttggctgtt ggtccggcct actcagctca    1680
ctgcattgga attactgaca gggatttcat tgagggggtg catggaggaa cttgggtttc    1740
agctaccctg gagcaagaca agtgtgtcac tgttatggcc cctgacaagc cttcattgga    1800
catctcacta gagacagtag ccattgatag acctgctgag gtgaggaaag tgtgttacaa    1860
tgcagttctc actcatgtga agattaatga caagtgcccc agcactggag aggcccacct    1920
agctgaagag aacagagggg acaatgcgtg caagcgcact tattctgata gaggctgggg    1980
caatggctgt ggcctatttg ggaaagggag cattgtggca tgcgccaaat tcacttgtgc    2040
caaatccatg agtttgtttg aggttgatca gaccaaaatt cagtatgtca tcagagcaca    2100
attgcatgta ggggccaagc aggaaaattg gaataccgac attaagactc tcaagtttga    2160
tgccctgtca ggctcccagg aagtcgagtt cattgggtat ggaaaagcta cactggaatg    2220
ccaggtgcaa actgcggtgg actttggtaa cagttacatc gctgagatgg aaacagagag    2280
ctggatagtg gacagacagt gggcccagga cttgaccctg ccatggcaga gtggaagtgg    2340
cggggtgtgg agagagatgc atcatcttgt cgaatttgaa cctcgcatgc cgccactat    2400 cagagtactg gccctgggaa accaggaagg ctccttgaaa acagctctta ctggcgcaat    2460
gagggttaca aaggacacaa atgacaacaa cctttacaaa ctacatggtg acatgtttc     2520 ttgcagagtg aaattgtcag ctttgacact caagggaca tcctacaaaa tatgcactga    2580
caaaatgttt tttgtcaaga acccaactga cactggccat ggcactgttg tgatgcaggt    2640
gaaagtgtca aaaggagccc cctgcaggat tccagtgata gtagctgatg atcttacagc    2700
ggcaatcaat aaaggcattt tggttacagt taaccccatc gcctcaacca atgatgatga    2760
agtgctgatt gaggtgaacc cacctttttgg agacagctac attatcgttg ggagaggaga    2820
ttcacgtctc acttaccagt ggcacaaaga gggaagctca ataggaaagt tgttcactca    2880
gaccatgaaa ggcgtggaac gcctggccgt catgggagac accgcctggg atttcagctc    2940
cgctggaggg ttcttcactt cggttgggaa aggaattcat acggtgtttg gctctgcctt    3000 tcagggcta tttggcggct tgaactggat aacaaaggtc atcatggggg cggtacttat    3060
atgggttggc atcaacacaa gaaacatgac aatgtccatg agcatgatct tggtaggagt    3120
gatcatgatg ttttttgtctc taggagttgg ggcggatcaa ggatgcgcca tcaactttgg    3180
caagagagag ctcaagtgcg gagatggtat cttcatattt agagactctg atgactggct    3240
gaacaagtac tcatactatc agaagatcc tgtgaagctt gcatcaatag tgaaagcctc    3300
ttttgaagaa gggaagtgtg gcctaaattc agttgactcc cttgagcatg agatgtggag    3360
aagcagggca gatgagatca atgccatttt tgaggaaaac gaggtggaca tttctgttgt    3420
cgtgcaggat ccaaagaatg tttaccagag aggaactcat ccattttcca gaattcggga    3480
tggtctgcag tatggttgga aagacttggg taagaacctt gtgttctccc cagggaggaa    3540
gaatggaagc ttcatcatag atggaaagtc caggaaagaa tgcccgtttt caaaccgggt    3600
ctggaattct ttccagatag aggagtttgg gacgggagtg ttcaccacac gcgtgtacat    3660
ggacgcagtc tttgaataca ccatagactg cgatggatct atcttgggtg cagcggtgaa    3720
```

```
cggaaaaaag agtgcccatg gctctccaac attttggatg ggaagtcatg aagtaaatgg      3780
gacatggatg atccacacct tggaggcatt agattacaag gagtgtgagt ggccactgac      3840
acatacgatt ggaacatcag ttgaagagag tgaaatgttc atgccgagat caatcggagg      3900
cccagttagc tctcacaatc atatccctgg atacaaggtt cagacgaacg gaccttggat      3960
gcaggtacca ctagaagtga agagagaagc ttgcccaggg actagcgtga tcattgatgg      4020
caactgtgat ggacggggaa atcaaccag atccaccacg gatagcggga aagttattcc       4080
tgaatggtgt tgccgctcct gcacaatgcc gcctgtgagc ttccatggta gtgatgggtg      4140
ttggtatccc atggaaatta ggccaaggaa aacgcatgaa agccatctgg tgcgctcctg      4200
ggttacagct ggagaaatac atgctgtccc ttttggtttg gtgagcatga tgatagcaat      4260
ggaagtggtc ctaaggaaaa gacagggacc aaagcaaatg ttggttggag gagtagtgct      4320
cttgggagca atgctggtcg ggcaagtaac tctccttgat ttgctgaaac tcacagtggc      4380
tgtgggattg catttccatg agatgaacaa tggaggagac gccatgtata tggcgttgat      4440
tgctgccttt tcaatcagac cagggctgct catcggcttt gggctcagga ccctatggag      4500
ccctcgggaa cgccttgtgc tgaccctagg agcagccatg gtggagattg ccttgggtgg      4560
cgtgatgggc ggcctgtgga gtatctaaa tgcagtttct ctctgcatcc tgacaataaa       4620
tgctgttgct tctaggaaag catcaaatac catcttgccc ctcatggctc tgttgacacc      4680
tgtcactatg gctgaggtga acttgccgc aatgttcttt tgtgccgtgg ttatcatagg       4740
ggtccttcac cagaatttca aggacacctc catgcagaag actataccctc tggtggccct    4800 cacactcaca tcttacctgg gcttgacaca acctttttg ggcctgtgtg catttctggc       4860
aacccgcata tttgggcgaa ggagtatccc agtgaatgag gcactcgcag cagctggtct      4920
agtgggagtg ctggcaggac tggcttttca ggagatggag aacttccttg gtccgattgc      4980
agttggagga ctcctgatga tgctggttag cgtggctggg agggtggatg gctagagct       5040 caagaagctt ggtgaagttt catgggaaga ggaggcggga atcagcggga gttccgcccg      5100
ctatgatgtg gcactcagtg aacaaggga gttcaagctg ctttctgaag agaaagtgcc       5160
atgggaccag gttgtgatga cctcgctggc cttggttggg gctgccctcc atccatttgc      5220
tcttctgctg gtccttgctg ggtggctgtt tcatgtcagg ggagctagga gaagtgggga     5280
tgtcttgtgg gatattccca ctcctaagat catcgaggaa tgtgaacatc tggaggatgg      5340
gatttatggc atattccagt caaccttctt gggggcctcc cagcgaggag tgggagtggc     5400
acagggaggg gtgttccaca caatgtggca tgtcacaaga ggagctttcc ttgtcaggaa      5460
tggcaagaag ttgattccat cttgggcttc agtaaaggaa gaccttgtcg cctatggtgg     5520 ctcatgaag ttgaaggca gatgggatgg agaggaagag gtccagttga tcgcggctgt        5580
tccaggaaag aacgtggtca acgtccagac aaaaccgagc ttgttcaaag tgaggaatgg     5640
gggagaaatc ggggctgtcg ctcttgacta tccgagtggc acttcaggat ctcctattgt      5700
taacaggaac ggagaggtga ttgggctgta cggcaatggc atccttgtcg gtgacaactc      5760
cttcgtgtcc gccatatccc agactgaggt gaaggaagaa ggaaaggagg agctccaaga     5820
gatcccgaca atgctaaaga aaggaatgac aactgtcctt gattttcatc ctggagctgg      5880
gaagacaaga cgtttcctcc cacagatctt ggccgagtgc gcacggagac gcttgcgcac      5940
tcttgtgttg gccccacca gggttgttct ttctgaaatg aaggaggctt ttcacggcct       6000
ggacgtgaaa ttccacacac aggctttttc cgctcacggc agcgggagag aagtcattga      6060
tgccatgtgc catgccaccc taacttacag gatgttggaa ccaactaggg ttgttaactg      6120
```

```
ggaagtgatc attatggatg aagcccattt tttggatcca gctagcatag ccgctagagg    6180
ttgggcagcg cacagagcta gggcaaatga aagtgcaaca atcttgatga cagccacacc    6240
gcctgggact agtgatgaat ttccacattc aaatggtgaa atagaagatg ttcaaacgga    6300
catacccagt gagccctgga acacagggca tgactggatc ctagctgaca aaaggcccac    6360
ggcatggttc cttccatcca tcagagctgc aaatgtcatg gctgcctctt tgcgtaaggc    6420
tggaaagagt gtggtggtcc tgaacaggaa aacctttgag agagaatacc ccacgataaa    6480
gcagaagaaa cctgacttta tattggccac tgacatagct gaaatgggag ccaacctttg    6540
cgtggagcga gtgctggatt gcaggacggc ttttaagcct gtgcttgtgg atgaagggag    6600
gaaggtggca ataaaagggc acttcgtat ctccgcatcc tctgctgctc aaaggagggg    6660
gcgcattggg agaaatccca acagagatgg agactcatac tactattctg agcctacaag    6720
tgaaaataat gcccaccacg tctgctggtt ggaggcctca atgctcttgg acaacatgga    6780
ggtgaggggg ggaatggtcg ccccactcta tggcgttgaa ggaactaaaa caccagtttc    6840
ccctggtgaa atgagactga gggatgacca gaggaaagtc ttcagagaac tagtgaggaa    6900
ttgtgacctg cccgttggc tttcgtggca agtggccaag gctggtttga agacgaatga    6960
tcgtaagtgg tgttttgaag gccctgagga acatgagatc ttgaatgaca gcggtgaaac    7020
agtgaagtgc agggctcctg gaggagcaaa gaagcctctg cgcccaaggt ggtgtgatga    7080
aagggtgtca tctgaccaga gtgcgctgtc tgaatttatt aagtttgctg aaggtaggag    7140
gggagctgct gaagtgctag ttgtgctgag tgaactccct gatttcctgg ctaaaaaagg    7200
tggagaggca atggatacca tcagtgtgtt cctccactct gaggaaggct ctagggctta    7260
ccgcaatgca ctatcaatga tgcctgaggc aatgacaata gtcatgctgt ttatactggc    7320
tggactactg acatcgggaa tggtcatctt tttcatgtct cccaaaggca tcagtagaat    7380
gtctatggcg atgggcacaa tggccggctg tggatatctc atgttccttg gaggcgtcaa    7440
acccactcac atctcctatg tcatgctcat attctttgtc ctgatggtgg ttgtgatccc    7500
cgagccaggg caacaaaggt ccatccaaga caaccaagtg gcatacctca ttattggcat    7560
cctgacgctg gtttcagcgg tggcagccaa cgagctagga atgctggaga aaaccaaaga    7620
ggacctcttt gggaagaaga acttaattcc atctagtgct tcaccctgga gttggccgga    7680
tcttgacctg aagccaggag ctgcctggac agtgtacgtt ggcattgtta caatgctctc    7740
tccaatgttg caccactgga tcaaagtcga atatggcaac ctgtctctgt ctggaatagc    7800
ccagtcagcc tcagtccttt cttcatgga caaggggata ccattcatga agatgaatat    7860
ctcggtcata atgctgctgg tcagtggctg gaattcaata acagtgatgc ctctgctctg    7920
tggcataggg tgcgccatgc tccactggtc tctcattta cctggaatca agcgcagca    7980 gtcaaagctt gcacagagaa gggtgttcca tggcgttgcc gagaaccctg tggttgatgg    8040
gaatccaaca gttgacattg aggaagctcc tgaaatgcct gcccttatg agaagaaact    8100 ggctctatat ctccttcttg ctctcagcct agcttctgtt gccatgtgca gaacgccctt    8160
ttcattggct gaaggcattg tcctagcatc agctgcctta gggccgctca tagagggaaa    8220
caccagcctt ctttggaatg gacccatggc tgtctccatg acaggagtca tgaggggaa    8280 tcactatgct tttgtgggag tcatgtacaa tctatggaag atgaaaactg acgccggggg    8340
gagcgcgaat ggaaaaactt tgggtgaagt ctggaagagg gaactgaatc tgttggacaa    8400
gcgacagttt gagttgtata aaaggaccga cattgtggag gtggatcgtg atacggcacg    8460
```

```
caggcatttg gccgaaggga aggtggacac cggggtggcg gtctccaggg ggaccgcaaa    8520
gttaaggtgg ttccatgagc gtggctatgt caagctggaa ggtagggtga ttgacctggg    8580
gtgtggccgc ggaggctggt gttactacgc tgctgcgcaa aaggaagtga gtggggtcaa    8640
aggatttact cttggaagag acggccatga gaaacccatg aatgtgcaaa gtctgggatg    8700
gaacatcatc accttcaagg acaaaactga tatccaccgc ctagaaccag tgaaatgtga    8760 caccctttg tgtgacattg gagagtcatc atcgtcatcg gtcacagagg gggaaaggac    8820
cgtgagagtt cttgatactg tagaaaaatg gctggcttgt ggggttgaca acttctgtgt    8880
gaaggtgtta gctccataca tgccagatgt tctcgagaaa ctggaattgc tccaaaggag    8940
gtttggcgga acagtgatca ggaaccctct ctccaggaat tccactcatg aaatgtacta    9000
cgtgtctgga gcccgcagca atgtcacatt tactgtgaac caaacatccc gcctcctgat    9060
gaggagaatg aggcgtccaa ctggaaaagt gaccctggag gctgacgtca tcctcccaat    9120
tgggacacgc agtgttgaga cagacaaggg accctggac aaagaggcca tagaagaaag    9180
ggttgagagg ataaaatctg agtacatgac ctcttggttt tatgacaatg acaacccta    9240 caggacctgg cactactgtg gctcctatgt cacaaaaacc tcaggaagtg cggcgagcat    9300
ggtaaatggt gttattaaaa ttctgacata tccatgggac aggatagagg aggtcacaag    9360
aatggcaatg actgacacaa cccctttgg acagcaaaga gtgtttaaag aaaaagttga    9420
caccagagca aaggatccac cagcgggaac taggaagatc atgaaagttg tcaacaggtg    9480
gctgttccgc cacctggcca gagaaaagaa ccccagactg tgcacaaagg aagaatttat    9540
tgcaaaagtc cgaagtcatg cagccattgg agcttacctg gaagaacaag aacagtggaa    9600
gactgccaat gaggctgtcc aagacccaaa gttctgggaa ctggtggatg aagaaaggaa    9660
gctgcaccaa caaggcaggt gtcggacttg tgtgtacaac atgatgggga aaagagagaa    9720
gaagctgtca gagtttggga aagcaaaggg aagccgtgcc atatggtata tgtggctggg    9780
agcgcggtat cttgagtttg aggccctggg attcctgaat gaggaccatt gggcttccag    9840
ggaaaactca ggaggaggag tggaaggcat tggcttacaa tacctaggat atgtgatcag    9900
agacctggct gcaatggatg gtggtggatt ctacgcggat gacaccgctg atgggacac    9960 gcgcatcaca gaggcagacc ttgatgatga acaggagatc ttgaactaca tgagcccaca   10020
tcacaaaaaa ctggcacaag cagtgatgga aatgacatac aagaacaaag tggtgaaagt   10080
gttgagacca gccccaggag ggaaagccta catggatgtc ataagtcgac gagaccagag   10140
aggatccggg caggtagtga cttatgctct gaacaccatc accaacttga agtccaatt   10200 gatcagaatg gcagaagcag agatggtgat acatcaccaa catgttcaag attgtgatga   10260
atcagttctg accaggctgg aggcatggct cactgagcac ggatgtgaca gactgaagag   10320
gatggcggtg agtggagacg actgtgtggt ccggcccatc gatgacaggt tcggcctggc   10380
cctgtcccat ctcaacgcca tgtccaaggt tagaaaggac atatctgaat ggcagccatc   10440
aaaagggtgg aatgattggg agaatgtgcc cttctgttcc caccacttcc atgaactaca   10500
gctgaaggat ggcaggagga ttgtggtgcc ttgccgagaa caggacgagc tcattgggag   10560
aggaaggtgt tctccaggaa acggctggat gatcaaggaa acagcttgcc tcagcaaagc   10620
ctatgccaac atgtggtcac tgatgtattt tcacaaaagg acatgaggc tactgtcatt   10680 ggctgttccc tcagctgttc ccacctcatg ggttccacaa ggacgcacaa catggtcgat   10740
tcatgggaaa ggggagtgga tgaccacgga agacatgctt gaggtgtgga acagagtatg   10800
gataaccaac aacccacaca tgcaggacaa gacaatggtg aaaaaatgga gagatgtccc   10860
```

```
ttatctaacc aagagacaag acaagctgtg cggatcactg attggaatga ccaatagggc  10920
cacctgggcc tcccacatcc atttagtcat ccatcgtatc cgaacgctga ttggacagga  10980
gaaatacact gactacctaa cagtcatgga caggtattct gtggatgctg acctgcaact  11040
gggtgagctt atctgaaaca ccatctaaca ggaataaccg ggatacaaac cacgggtgga  11100
gaaccggact ccccacaacc tgaaaccggg atataaacca cggctggaga accgggctcc  11160
gcacttaaaa tgaaacagaa accgggataa aaactacgga tggagaaccg gactccacac  11220
attgagacag aagaagttgt cagcccagaa ccccacacga gttttgccac tgctaagctg  11280
tgaggcagtg caggctggga cagccgacct ccaggttgcg aaaaacctgg tttctgggac  11340
ctcccacccc agagtaaaaa gaacggagcc tccgctacca ccctcccacg tggtggtaga  11400
aagacggggt ctagaggtta gaggagaccc tccagggaac aaatagtggg accatattga  11460
cgccagggaa agaccggagt ggttctctgc ttttcctcca gaggtctgtg agcacagttt  11520
gctcaagaat aagcagacct ttggatgaca aacacaaaac cact                   11564
```

IDNA VACCINES AND METHODS FOR USING THE SAME

CROSS-REFERENCE TO RELATED APPLICATIONS

This application is a continuation of U.S. application Ser. No. 13/054,372, filed Jun. 15, 2011, now issued as U.S. Pat. No. 8,691,563, which is a national stage filing under 35 U.S.C. § 371 of International Application No. PCT/US 2009/004133, filed on Jul. 17, 2009, which claims the priority of U.S. Provisional Application No. 61/081,482, filed Jul. 17, 2008, the entire contents of which are incorporated by reference herein.

GOVERNMENT INTERESTS

The inventors received material related to the subject matter of this application from the U.S. government under an agreement pursuant to 15 U.S.C. § 3710a, accordingly the U.S. government may have certain rights in the subject matter.

FIELD

Various embodiments described herein relate to live attenuated viral vaccines and systems and methods for making and administering such vaccines.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art.

Many RNA viruses, including Yellow Fever (YF) virus and Venezuelan Equine Encephalitis (VEE) virus, are dangerous human pathogens. VEE is a Category B and YF is a Category C Priority Pathogen as categorized by NIH/NI-AID.

The VEE virus is a positive single-stranded RNA arbovirus that belongs to the Alphavirus genus of the Togaviridae family. The virus is transmitted primarily by mosquitoes, which bite an infected animal and then bite and feed on another animal or human. VEE currently is rare in the U.S. A major epizootic in horses occurred in Texas, but only about 100 laboratory-confirmed cases in humans have been documented. However, changing climate may favor establishment of the virus in warmer areas of the U.S. Additionally, VEE is a potential biological weapon and bioterrorism agent.

The YF virus is also a positive single-stranded RNA arbovirus. However, unlike VEE, the YF virus belongs to the family Flaviviridae. YF disease occurs mostly in Africa and South America. Human infection begins after deposition of viral particles through the skin by an infected mosquito. The disease is frequently severe. More moderate cases can occur as a result of previous infection by another flavivirus. There is a difference between disease outbreaks in rural or forest areas and in urban areas (Barnett, 2007). Disease outbreaks in towns and non-native people can be more serious because of higher densities of mosquito vectors and higher population densities. As of 2001, the World Health Organization (WHO) estimates that YF virus causes 200,000 illnesses and 30,000 deaths every year in unvaccinated populations. In most cases, supportive therapy is required for YF patients. Fluid replacement, transfusion of blood derivates, and other measures are used in severe cases.

Live attenuated viruses have been developed to serve as vaccines for many RNA viruses such as VEE and YF, poliomyelitis, influenza, measles, mumps, rabies, and rubella viruses. Traditional live attenuated RNA virus vaccines comprise live attenuated RNA viruses that are injected into the vaccine recipient. The injected virus delivers its RNA genome into the cells, which results in production of viral antigens as well as progeny attenuated viruses in the tissues of the vaccine recipient. This leads to the elicitation of an immune response that protects against the counterpart non-attenuated virus.

SUMMARY

This application provides vectors comprising DNA encoding an infectious RNA molecule and an RNA polymerase promoter, where the DNA encoding an infectious RNA molecule is operably linked to the RNA polymerase promoter and the infectious RNA molecule encodes a Yellow Fever (YF) virus. In certain embodiments, the YF virus is non pathogenic. Also described are vaccines for Yellow Fever (YF) comprising the vectors described above, and methods for using the vaccines to immunize against a YF virus. Also described are homogeneous clonally purified live attenuated virus prepared from cultured cells transfected with the vector, vaccines for YF comprising the same, and methods for using the vaccines to immunize against a YF virus.

This application also provides vectors comprising DNA encoding an infectious RNA molecule and an RNA polymerase promoter, where the DNA encoding an infectious RNA molecule is operably linked to the RNA polymerase promoter and the infectious RNA molecule encodes a a Venezuelan Equine Encephalitis (VEE) virus. In certain embodiments, the VEE virus is non-pathogenic. Also described are vaccines for Venezuelan Equine Encephalitis (VEE) comprising the vectors described above, and methods for using the vaccines to immunize against a VEE virus. Also described are homogeneous clonally purified live attenuated virus prepared from cultured cells transfected with the vector, vaccines for VEE comprising the same, and methods for using the vaccines to immunize against a VEE virus.

This application also provides vectors comprising a DNA encoding an infectious RNA molecule and a cytomegalovirus (CMV) RNA polymerase promoter, where the DNA encoding an infectious RNA molecule is operably linked to the CMV RNA polymerase promoter, the CMV RNA polymerase promoter is located from about 12 to about 18 nucleic acid residues upstream of the 5' end of said DNA encoding an infectious RNA molecule, and the infectious RNA molecule encodes an attenuated RNA virus. In certain embodiments, the attenuated RNA virus is an alphavirus or a flavivirus.

This application also provides methods for attenuating an RNA virus, comprising inserting two RNA dependent RNA promoters into the cDNA encoding the RNA virus, whereby the nucleocapsid and glycoproteins are separately expressed from independent promoters.

BRIEF DESCRIPTION OF THE DRAWINGS

FIG. 1. Schematic representation of iDNA based VEE TC-83 vaccines. (A) Full-length cDNA corresponding to the TC-83 RNA genome is cloned into the DNA containing functional DNA-dependent RNA polymerase promoter, for example CMV promoter. Location of CMV promoter, 26S promoter, poly-A, transcription termination, and ribozyme (optional) sequences are shown. (B) Example of the modified, iDNA-based TC-83 vaccine, in which TC-83 capsid and glycoprotein genes are expressed from independent promoters. Location of the promoters is shown. The transcription start site can be modified by varying the distance between the 3' end of the CMV promoter and the 5' end of the TC-83 coding sequence.

FIG. 2. Administration of the TC-83 iDNA vaccine into cells in vitro or in vivo. Injection of the TC-83 DNA vaccine under control of DNA-dependent RNA polymerase promoter (see FIG. 1) into cells in vitro or in vivo is shown. As a result of TC-83 iDNA vaccine administration, the TC-83 live attenuated virus vaccine is generated. If administered in vivo, production of TC-83 vaccine in the tissues of the patient elicits immune response to the TC-83 vaccine.

FIG. 3. Schematic representation of iDNA-based YF17D vaccine. Full-length cDNA corresponding to the 17D ANA genome is cloned into the DNA containing functional RNA polymerase promoter, for example CMV promoter. Location of CMV promoter, polyA, transcription termination, and ribozyme sequences are shown.

FIG. 4. Administration of the recombinant YF17D iDNA vaccine into cells in vitro or in vivo. Injection of the 17D iDNA vaccine containing YF17D cDNA under control of DNA-dependent RNA polymerase promoter into cells in vitro or in vivo is shown. As a result of 17D iDNA vaccine administration, the 17D live attenuated virus vaccine is generated. If administered in vivo to the tissues of vaccine recipient, production of YF17D vaccine in the tissues of the patient leads to elicitation of immune response to the 17D vaccine.

FIG. 5. Immunofluorescense assay (IFA) of CHO cells transfected with (A) VEE TC-83 iDNA vaccine, Clone 13-2 (FIG. 6); and (B) p3-40 DNA expressing TC-83 structural proteins (control). Focus of TC-83-positive cells is visible on panel (A), whereas panel (B) shows individual TC-83-positive cells. Cells are transfected with DNA vaccine using Fugene 6 transfection reagent or a similar gene transfer method. Transfected cells are incubated at 37° C. in 5% $CO_2$ incubator. Following 24 hr incubation, cells are fixed with cold acetone, and IFA is done using rabbit antibody specific for TC-83 antigen. Then, cells are incubated using rhodamine-conjugated antibody for rabbit IgG and observed using fluorescent microscopy.

FIG. 6. iDNA sequence fragment from pAA_TC83 plasmid (Clones #13-1; 13-2) containing the TC-83 cDNA downstream from CMV promoter (SEQ ID NO: 1). Locations of CMV promoter, 26 S promoter, and polyA site are indicated.

FIG. 7. iDNA sequence fragment of modified pAA_TC-83_C_GP plasmid (Clone #12) containing two TC-83 26S promoters (SEQ ID NO: 2). Locations of CMV promoter, 26 S promoters, and polyA site are indicated.

FIG. 8. iDNA sequence fragment of pCMV_YF17D containing the YF17D cDNA downstream from CMV promoter and hepatitis a ribozyme and BGH transcription termination and polyadenylation cassettes downstream from 3' end of the YF17D sequence (SEQ ID NO: 3).

FIG. 9. Optimization of the distance between the 3' end of the CMV promoter and the 5' end of the TC-83 cDNA by encapsidation assay using HA- or N-vectors and DNA c-helpers.

FIG. 10. Transfection of CHO cells with TC-83 iDNA #13-1 (wild-type) results in rapid expression of TC-83 antigen in CHO cells.

FIG. 11. Transfection of CHO cells with TC-83 iDNA #12 (double 26S promoter) results in delayed expression of TC-83 antigen in CHO cells.

FIG. 12. TC-83 viruses generated from infectious clones in vitro are avirulent in BALE/c mice. Cloned TC-83 viruses are generated by transfection of CHO cells using electroporation with infectious TC-83 vaccine cDNA clones #12 and #13-1. Viruses are inoculated in mice according to standard USAMRIID protocol (Dr. Michael Parker, USAMRIID, Ft. Detrick, Md.).

FIG. 13. Synthetic oligonucleotides of varying lengths (SEQ ID NOS: 4-14, from top to bottom) for creating a series of "capsid iDNA" plasmids in which the distance between the promoter and the iDNA varies from 8 to 25 base pairs (see Example 8). The capitalized and bolded A shows the 5' end of the VEE sequence (in TC-38, the start codon is ATA rather than ATG; see the ATA nucleotides at positions 704-706 in SEQ ID NO: 1).

DETAILED DESCRIPTION

Described herein are compositions for eliciting an immune response or a protective immunity against Yellow Fever (YF) or Venezuelan Equine Encephalitis (VEE) viruses. In one embodiment, the compositions comprise vaccines for preventing and/or treating YF or VEE virus associated diseases. Also described are methods of making, using and testing the same.

Live attenuated, cell-culture derived TC-83 vaccine for VEE has been developed previously. TC-83 contains attenuating mutations (Kinney et al., 1993). The current TC-83 vaccine is fully licensed for veterinary use in horses and was used successfully during 1970-1971 Texas epizootic. The vaccine has also been approved for use in people as an Investigational New Drag (IND). The TC-83 vaccine provides protection against many epizootic strains. The TC-83 vaccine has been used as part of safety programs and was important in protecting individuals working with infected animals and virus preparations. To date, the vaccine has been administered to ~9,000 people. Another human IND vaccine, C-84, has been prepared from formalin-inactivated TC-83 vaccine. Because of the history of successful use as a vaccine in people, the TC-83 vaccine is also a promising vaccine vector, which can be used as a carrier of therapeutic or vaccine-relevant genes (Pushko P., U.S. Patent Application No. 2006/0198854, Vector platforms derived from the alphavinas vaccines).

Because there is no specific therapy for YF, vaccination is the only effective medical countermeasure. Current YF vaccine is a live, attenuated virus preparation made from the 17D YF virus strain (Smithburn et al., 1956). The 17D live virus vaccines have been considered to be safe and effective (Monath, 2001). The 17D YF vaccine virus is the foundation for both the 17D-204 and 17DD lineages. Vaccine 17D-204 is used in the U.S. and Australia, whereas vaccine 17DD is used in Brazil. Sequencing has revealed that the 17D-204 and 17DD vaccine types are not identical, which reflects accumulation of genetic mutations during multiple passages of virus seeds. With safety record in humans, the YF17D is also a promising vector for the development of vaccines against flavivirus-related pathogens (e.g. chimeric YF17D-based vaccines against Japanese encephalitis, dengue, and West Nile virus (Pugachev et al, 2005) as well as against pathogens outside the flavivirus genus such as malaria (Tao et al., 2005) and Lassa virus (Bredenbeek et al., 2006).

Described herein are iDNA molecules expressing the RNA genome of live attenuated viruses and methods for using the same. In certain embodiments, when iDNA is injected into the cultured cells in vitro, RNA of live attenuated virus is generated in the cells by in vivo transcription. This initiates production of progeny attenuated viruses in the medium from cultured cells. Such homogenous, clonally pure live attenuated virus can be used for vaccination as improved, homogeneous live attenuated vaccine. In other embodiments, when iDNA is injected into the cells of a vaccine recipient, RNA of live attenuated virus is generated by in vivo transcription in the tissues. This initiates production of progeny attenuated viruses in the tissues of vaccine recipient, as well as elicitation of effective immune response to live attenuated virus. Similarly to any DNA, the iDNA can be made in bacterial cells and represents a stable molecule.

In certain embodiments, the iDNA molecules are vectors comprising DNA encoding an infectious RNA molecule, where the infectious RNA molecule in turn encodes a YF or a VEE virus. The DNA encoding an infectious RNA molecule can be operably linked to an RNA polymerase promoter, and is generally modified to encode a non-pathogenic (attenuated) YF or VEE virus.

In certain embodiments, the iDNA (infectious DNA) molecules comprise the VEE TC-83 or the VT YF17D cDNA. For example, an exemplary iDNA-based VEE vaccine comprises a DNA molecule that contains the complete cDNA copy of the RNA genome of the TC-83 live attenuated virus. In this iDNA molecule, the TC-83 cDNA is placed downstream from an RNA polymerase promoter, such as the CMV promoter. When such an iDNA molecule is introduced into cells in vitro, the TC-83 viral RNA is generated in the cells. The resulting TC-83 RNA is "infectious" and initiates production of the TC-83 live attenuated virus vaccine in the cells. Such TC-83 virus vaccine can be harvested from cultured cells and used for vaccination according to current practices. In certain embodiments, the vaccine that is generated from the TC-83 iDNA represents homogeneous progeny virus generated from the same, well-characterized, stable DNA. Because the same, clonally purified, iDNA is used for the production of the vaccine lots, such vaccine will in certain embodiments have greater uniformity and lot-to-lot consistency compared to current vaccines, which can accumulate mutations during virus passages.

Alternatively, iDNA vaccine containing the TC-83 cDNA can be administered to the vaccine recipient directly. Such iDNA administration to the vaccine recipient initiates production of the TC-83 virus vaccine in the tissues of the patient in vivo, which provides successful vaccination against VEE.

Similarly, iDNA-based YF vaccines can comprise a DNA molecule that contains the cDNA copy of the RNA genome of the YF17D live attenuated virus. In this iDNA molecule, the YF17D cDNA copy can be placed downstream from an RNA polymerase promoter, for example the cytomegalovirus (CMV) promoter. When such iDNA molecule is introduced into cells in vitro or administered directly to the tissues of vaccine recipient in vivo, the 17D viral RNA is generated by transcription from the RNA polymerase promoter. The resulting YF17D RNA is infectious and initiates production of the YF17D live attenuated vaccine. When injected into tissues of a vaccine recipient in vivo, such YF17D-based iDNA provides successful vaccination of the patient against YF.

The TC-83 or YF17D cDNA can be modified to ensure sufficient attenuation and/or to introduce other characteristics, while still maintaining infectivity and the desired therapeutic effect. In certain embodiments, the cDNA is modified by insertion, deletion, and/or substitution of one or more of the nucleotides in the TC-83 or YF17D cDNA sequence. For example, the modified cDNA can have at least 50%, 60%, 70%, 80%, or 90% sequence identity with the TC-83 or YF17D sequence, such as at least 91%, 92%, 93%, 94%, 95%, 96%, 97%, 98%, or 99% sequence identity.

Examples of modified cDNAs include a DNA having an additional 26S promoter in the modified TC-83 iDNA Clone 12 (see example 3, Table I). This modification slows the development of TC-83-positive foci, which is a sign of additional attenuation caused by insertion of the additional 26S promoter in this construct (FIG. 1, B). Such additional attenuation can improve the TC-83 vaccine and reduce adverse effects associated with this vaccine. In this example, an additional 26S promoter could be inserted so that the TC-83 nucleocapsid and glycoproteins are generated from independent promoters (FIG. 1B). Thus, the TC-83 26S promoter is duplicated, and the capsid and glycoproteins are generated from the two 26S promoters. Other modification can be made to increase the stability of the iDNA in E. coli or in target cells, or to increase stability of iDNA in E. coli cells.

Additionally, other genes or gene fragments, including genetic material from other alphaviruses, or from unrelated sources such other viruses, bacteria, microorganisms, other organisms, plants, animals, or/and humans could be inserted into the iDNA. In such cases, the modified TC-83 or YF17D iDNA could serve as a vector for expression of heterologous genes in vitro or in vivo.

Described herein are specialized vectors for preparation of iDNA vaccines. However, it will be appreciated by those skilled in the art that the iDNA described herein can be formed using any suitable vector. In general, a vector is a nucleic acid molecule (typically DNA or RNA) that serves to transfer a passenger nucleic acid sequence (i.e., DNA or RNA) into a host cell. Three common types of vectors include plasmids, phages and viruses. In an exemplary embodiment, the vector is a plasmid. The present iDNA vaccines can be comprised of DNA that is produced as a plasmid that can be introduced into animal tissue and therein is expressed by animal cells to produce a messenger ribonucleic acid (mRNA) molecule approximately the size of the YF or the VEE genome, which is translated to produce viral polyproteins. The viral polyproteins in turn are processed by cellular machinery to provide a full set of YF or VEE proteins that are capable of initiating replication of the above primary RNA transcript and thus initiating the virus replication cycle in animal tissue into which the above DNA plasmid was introduced.

Suitable and exemplary plasmid vectors that have been used in conventional DNA vaccines include, but are not limited to pBR322 (ATCC #31344); pUC19 (ATCC #37254); pcDNA3.1 (Invitrogen, Carlsbad Calif. 92008; Cat. NO. V385-20); pNGVL (National Gene Vector Laboratory, University of Michigan, Mich.); p414cyc (ATCC #87380), p414GALS (ATCC #87344), pBAD18 (ATCC #87393), pBLCAT5 (ATCC #77412), pBluescriptIIKS, (ATCC #87047), pBSL130 (ATCC #87145), pCM182 (ATCC #87656), pCMVtkLUC (ATCC #87633), pECV25 (ATCC #77187), pGEM-7zf (ATCC #87048), pGEX-KN (ATCC #77332), pIC20 (ATCC #87113, pUB110 (ATCC #37015), pUB18 (ATCC #37253).

The iDNA described herein is also under the control of a suitable promoter. For eukaryotic expression, examples of suitable promoters include the cytomegalovirus ("CMV") early promoter, the Rous sarcoma virus ("RSV") LTR promoter, and the SV40 promoter.

The following describes exemplary methods for making iDNA vectors and vaccines:

The cDNA fragment corresponding to the full-length TC-83 RNA is derived by reverse transcription and polymerase chain reaction (RT-PCR) by using the TC-83 viral RNA and the TC-83 sequence-specific oligonucleotide primers. TC-83 viral RNA is extracted from the TC-83 vaccine using phenol extraction or other methods. The TC-83-specific oligonucleotide primers can contain additional functional elements, including, but not limited to, restriction enzyme sites, transcription terminators, polyadenilation signals, ribozymes, etc.

Alternatively, two or more cDNA fragments encompassing the entire TC-83 RNA are generated using RT-PCR. Then, such cDNA fragments are assembled within a single plasmid so that they comprise the full-length cDNA corresponding to the full-length TC-83 RNA, as described in the previous paragraph.

Alternatively, the TC-83 cDNA, as described in the previous paragraphs, is generated by using chemical synthesis or a combination of chemical synthesis or/and PCR or/and RT-PCR.

The cDNA fragment corresponding to the full-length RNA is cloned into the DNA containing a functional RNA polymerase promoter, for example CMV promoter (FIG. 1A). An example of such resulting recombinant iDNA sequence is shown (FIG. 6). As a result of transcription in vitro or in vivo of such iDNA, functional infectious TC-83 RNA containing one or more attenuating mutations is generated. The distance between the promoter and the TC-83 cDNA can be optimized to ensure the desired level of RNA expression. In certain embodiments, the distance between the GAGCTC 3'-end of the CMV promoter (indicated at nucleotide (nt) 687 with an arrow in FIG. 6), and the 5'-end of the TC-83 cDNA (indicated at nucleotide 703 with another arrow in FIG. 6), is 15(±3) base pairs (bp). This allows efficient transcription and production of TC-83 RNA. For comparison, according to Invitrogen, the CMV transcription start site would be located at nt 697, which is 9 at from the GAGCTC 3' end of the CMV promoter within the pcDNA3.1(−) plasmid. Similarly, the 3' end of the TC-83 cDNA can be followed by ribozymes, transcription termination sequences, poly-A, as well as other nucleotides and signals to ensure optimal production of functionally active RNA. In a preferred embodiment, the distance between the 3' end of TC-82 cDNA (at 12170, FIG. 6) and the poly-A site is 184 bp and can vary from between 0 to about 500 bp.

Alternatively, the TC-83 nucleocapsid and glycoproteins are expressed from independent promoters (FIG. 1B).

The resulting recombinant plasmid iDNA containing the TC-83 cDNA under control of the RNA polymerase promoter (FIG. 1A,B) is generated and purified from *E. coli* cells. Purified iDNA is then introduced into cultured eukaryotic cells, for example into Chinese hamster ovary (CHO) cells, baby hamster kidney (BHK-21), or other susceptible cells (FIG. 2). DNA is administered to cells by injection, gene gun, electroporation, liposome transfection, or other gene transfer method. In the cells, the full-length infectious TC-83 RNA is generated by transcription, which initiates the production of TC-83 live attenuated virus in cultured cells and release of TC-83 virus in the medium (FIG. 2). The TC-83 virus is harvested from the cell cultures, formulated, and used as a VEE vaccine according to the current practice.

Alternatively, the recombinant iDNA containing the TC-83 cDNA (FIG. 1) is introduced into the vaccine recipient directly in vivo. The iDNA is administered into vaccine recipient tissues by injection, electroporation, liposome transfection, gene gun, or other genetic transfer method. In the tissues of vaccine recipient, the full-length infectious TC-83 RNA is generated by transcription, which initiates production of TC-83 live attenuated virus in vivo. The TC-83 virus antigens are released from the cells in vivo in the tissues, which initiates induction of effective immune response to TC-83 vaccine.

Similar to the TC-83 iDNA described above, a YF17D iDNA includes the YF17D cDNA. Full-length YF17D cDNA is derived from the full-length viral RNA or assembled from two or more fragments or synthesized by chemical means as described above for the TC-83. The full-length YF17D cDNA is placed under the control of a functional RNA polymerase promoter, as shown in FIG. 4A. In certain embodiments, the distance between the GAGCTC 3'-end of the CMV promoter and the 5'-end of the TC-83 cDNA, is 15(±3) by as described above for TC-83. This allows for efficient transcription and production of YF 17D RNA. Ribozyme, transcription termination and poly (A) cassettes are placed as required downstream from the 3' end of the YF17D cDNA to ensure correct transcription and polyadenylation of functional YF17D RNA transcripts. As a result of YF17D iDNA transcription in vitro or in vivo, functional infectious YF17D RNA (optionally containing one or more additional attenuating mutations) is generated. As seen in FIG. 4, transfection of BHK-21 cells with a full-length YF17D iDNA containing YF17D cDNA under control of the CMV promoter results in transcription of infectious RNA, translation, correct post-translational processing of polyprotein, assembly and release of infectious YF17D particles.

As noted above, modifications can be made to the full-length YF17D as well TC-83 cDNA constructs. Optimization of attenuation may additionally improve the YF17D iDNA vaccine and reduce adverse effects including viscerotropic disease associated with YF17D vaccination (Monath, 2007).

In certain embodiments, the methods described herein comprise administering a composition or a DNA vaccine comprising iDNA encoding for an attenuated YF or VEE virus in an acceptable pharmaceutical carrier to a subject in need thereof.

The amount of iDNA present in the compositions or in the DNA vaccines described herein is preferably a therapeutically or pharmaceutically effective amount. A "therapeutically effective amount" of iDNA is that amount necessary so that the nucleotide sequence coding for the YF or VEE polypeptide performs its immunological role without causing overly negative effects in the host to which the composition is administered. The exact amount of plasmid to be used and the composition/vaccine to be administered will vary according to factors such as the strength of the transcriptional and translational promoters used, the type of condition being treated, the mode of administration, as well as the other ingredients in the composition. In one embodiment, the composition or the vaccine formulation comprises from about 1 ng to about 1 mg of plasmid.

The immunogenicity of the DNA vaccines and pharmaceutical compositions can be modified by formulating with one or more pharmaceutically acceptable adjuvants or immunostimulants, such as alpha-interferon, beta-interferon, gamma-interferon, granulocyte macrophage colony stimulator factor ("GM-CSF"), macrophage colony stimulator factor ("M-CSF"), interleukin 2 ("IL-2"), interleukin 12 ("IL-12"), and CpG oligonucleotides. For preparing such compositions, methods well known in the art can be used. In certain embodiments, the iDNA is generated in *E. coli* cells as a plasmid DNA, containing unmethylated CpG motifs and itself constitutes an immunostimulating molecule that activates the immune system via toll-like receptors.

Subcutaneous injection, intradermal introduction, impression through the skin, and other modes of administration such as intraperitoneal, intravenous, oral, or inhalation delivery are also suitable. For example, vectors containing the iDNA can be introduced into the desired host by methods known in the art, for example, transfection, electroporation, microinjection, microparticles, microcapsules, transduction, cell fusion, DEAE dextran, calcium phosphate precipitation, lipofection (lyposome fusion), use of a gene gun (particle bombardment), or a DNA vector transporter (see, e.g., Wu et al., 1992, J. Biol. Chem. 267:963.967; Wu and Wu, 1988, J. Biol. Chem. 263:14621-14624).

As used herein, the term "treating," "treatment" and the like are used herein to generally mean obtaining a desired pharmacological and/or physiological effect, and refer to a process by which the symptoms of a YF or VEE associated disease are completely eliminated or ameliorated to any clinically and/or quantitatively measurable degree. The term "preventing" refers to a process by which a YF or VEE associated disease is obstructed and/or delayed. The compositions and vaccines described herein comprise iDNA (iDNA) capable of producing a live attenuated virus. In one embodiment, the live attenuated virus is produced in vivo.

As used herein, the term "immune response" includes a T cell response, increased serum levels of antibodies to an antigen, the presence of neutralizing antibodies to an antigen (such as a YF or VEE polypeptide), or combinations thereof. The term "protection" or "protective immunity" includes the ability of the serum antibodies or T cell response induced during immunization to protect (partially or totally) against disease or death caused by YF or VEE viruses.

The "subject" is a vertebrate, such as a mammal. Mammals include, but are not limited to, humans, other primates, rodents, farm animals, sport animals (horses, etc.) and pets. In certain embodiments, the subject is a human. In other embodiments, the methods find use in experimental animals (such as all species of monkeys), in veterinary application and/or in the development of animal models for disease. In certain embodiments, the vaccine is a VEE (such as TC-83) vaccine and the subject is a horse. A "subject in need thereof" refers to any subject, patient, or individual who could benefit from the methods described herein.

The term "therapeutically (or "pharmaceutically") effective dose" or "therapeutically (or "pharmaceutically") effective amount" means a dose or amount that produces the desired effect for which it is administered. The exact dose will depend on the purpose of the treatment, and will be ascertainable by one skilled in the art using known techniques.

The term "pharmaceutically acceptable" means approved by a regulatory agency of the federal or a state government or listed in the U.S. Pharmacopeia or other generally recognized pharmacopeia for use in animals, and more particularly, in humans.

The term "carrier" refers to a diluent, adjuvant, excipient, or vehicle with which the iDNA is administered. Such pharmaceutical carriers can be sterile liquids, such as water and oils, including those of petroleum, animal, vegetable or synthetic origin, such as peanut oil, soybean oil, mineral oil, sesame oil, combinations thereof and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, combinations thereof and the like. The composition, if desired, can also contain minor amounts of wetting or emulsifying agents, or pH buffering agents. These compositions can take the form of solutions, suspensions, emulsion, tablets, pills, capsules, powders, sustained-release formulations, combinations thereof and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, combinations thereof, etc. Examples of suitable pharmaceutical carriers are described in "Remington's Pharmaceutical Sciences" by E. W. Martin.

Thus, as used herein, the term "pharmaceutically acceptable carrier" means, but is not limited to, a vehicle for containing the iDNA that can be injected into a mammalian host without adverse effects. Suitable pharmaceutically acceptable carriers known in the art include, but are not limited to, gold particles, sterile water, saline, glucose, dextrose, or buffered solutions, combinations thereof and the like. Carriers may include auxiliary agents including, but not limited to, diluents, stabilizers (i.e., sugars and amino acids), preservatives, wetting agents, emulsifying agents, pH buffering agents, viscosity enhancing additives, colors, combinations thereof and the like.

As used herein, the singular forms "a", "an", and "the" include plural referents unless the context clearly dictates otherwise. Thus, for example, reference to "vaccine" includes a plurality of such vaccines and reference to "the dosage" includes reference to one or more dosages and equivalents thereof known to those skilled in the art, and so forth.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates, which may need to be independently confirmed. All publications, patents, patent applications and other references cited herein are hereby incorporated by reference.

While the disclosure has been described in detail with reference to certain embodiments thereof, it will be apparent to one skilled in the art that various changes can be made, and equivalents employed, without departing from the scone of the disclosure. In addition, the following examples are illustrative of the methods described herein and should not be considered as limiting the foregoing disclosure in any way.

EXAMPLES

Example 1. Preparation of TC-83 iDNA

Total RNA is extracted from the TC-83 vaccine using phenol extraction. The cDNA corresponding to the frill-length TC-83 RNA is derived by reverse transcription and polymerase chain reaction (RT-PCR) using extracted TC-83 viral RNA and the TC-83 sequence-specific oligonucleotide primers.

The cDNA fragment corresponding to the full length TC-83 RNA is cloned into the plasmid vector pASP5 containing a functional CMV promoter (FIG. 1A, FIG. 6), which yields the TC-83 iDNA, clone 13-1 and clone 13-2. The distance between the 3' end of the CMV promoter to the 5'end of the TC-83 cDNA is 15 bp as shown in FIG. 6. After transcription of such TC-83 iDNA in vitro or in vivo by cellular transcription machinery, functional infectious TC-83 RNA and TC-83 virus are generated.

The TC-83 iDNA can be easily modified to optimize functional characteristics, for example, the level of attenuation. For example, modified TC-83 cDNA, clone 12, is generated by duplicating the 26S promoter and placing the second 26S promoter upstream from the TC-83 glycoprotein genes (FIG. 1B, FIG. 7). In such a construct, the RNA that is generated from the CMV promoter expresses the TC-83 capsid and glycoproteins from independent 26S promoters. In order to ensure expression of the TC-83 proteins from such modified TC-83 RNA, appropriate changes are made, for example, ATG codon is introduced at the 5' terminus of the glycoprotein genes. The full-length RNA encoding cDNA of modified TC-83 (Clone 12) is introduced into the claimed plasmid vector pASP5 containing functional CMV promoter (FIG. 1B, FIG. 7). The distance between the 3' end of CMV promoter to the 5'end of modified TC-83 cDNA is 15 bp as shown in FIG. 7.

Example 2. Preparation of YF17D iDNA

Total RNA is extracted from the YF17D vaccine using phenol extraction or a similar method. The cDNAs corresponding to the full-length 17D RNA is derived by reverse transcription and polymerase chain reaction (RT-PCR) using extracted 17D viral RNA and the 17D sequence-specific oligonucleotide primers. Alternatively, the full-length YF17D cDNA is assembled from two or more plasmids.

The cDNA fragment corresponding to the full-length RNA is transferred into the claimed plasmid vector pASP5 containing functional CMV promoter (FIG. 3), which results in YF17D iDNA (FIG. 8). The distance between the 3' end of CMV promoter to the 5'end of YF 17D cDNA is 15 bp as shown in FIG. 8 and described above for the TC-83 constructs. After transcription of YF17D iDNA in cells in vitro or in vivo, functional infectious YF17D RNA and YF17D virus are generated.

Example 3. Transfection of CHO Cells with TC-83 iDNA Vaccine

Plasmid DNA containing TC-83 iDNA is transfected into CHO cells using Fugene 6 transfection reagent (Roche Applied Sciences). Briefly, CHO cells are grown in 75 cm² flasks, then rinsed with phosphate buffered saline (PBS) and trypsinized. Aliquot of CHO cell suspension is transferred into 6-well cell culture plates. Then, mixture of plasmid DNA and Fugene 6 reagent is added according to manufacturer's instructions. As plasmid DNA, the following constructs are used:
(1) VEE TC-83 modified iDNA, Clone 12 (FIG. 1B, FIG. 7);
(2) VEE TC-83 iDNA, Clone 131 (FIG. 1A, FIG. 6);
(3) VEE TC-83 iDNA, Clone 13-2 (FIG. 1A, FIG. 6);
(4) As a control, p3-10 DNA expressing TC-83 structural proteins only, is used.
As an additional control, untransfected CHO cells (5) are used. The iDNAs (1) through (3) contain the complete TC-83 cDNA and are expected to generate live TC-83 virus.

As described above, the Clone 12 iDNA (1) contains duplicated 26S promoter to express TC-83 capsid and glycoproteins from two independent 26S promoters (FIG. 1B). In contrast, DNA (4) contain only a fragment of TC-83 corresponding to the TC-83 structural genes only and is not expected to generate live TC-83 virus.

An aliquot (0.3 ml) from transfected CHO cells from 6-well plates is seeded into 8-well chamber slides. Transfected CHO cells are incubated at 37° C. in 5% $CO_2$. Cell mortality is determined in 6-well plates daily by visual microscopy. Immunofluoresense assay (IFA) is performed at 24 hr posttransfection using 8-well chamber slides with antiserum that recognizes the TC-83 antigens, according to the method described in Pushko et al. (1997). The results are shown in Table I. Cells transfected with iDNAs (1) through (3) die within 5 days posttransfection, whereas CHO cells with control transfections (4) and (5) remain alive. Also, foci of cells expressing TC-83 antigens are detected by IFA at 24 hr posttransfection in the cells transfected with DNAs (2) and (3), thus indicating presence of live TC-83 virus (FIG. 5). The result indicates that introduction of iDNA-based TC-83 vaccines into cultured cells resulted in production of live TC-83 virus.

TABLE I

Transfection of CHO cells with the TC-83 vaccine iDNA

| iDNA Vaccine* | CHO Cell Mortality after DNA transfection** | Foci of infected cells, By IFA*** |
|---|---|---|
| 1. VEE TC-83 modified iDNA, Clone 12 (FIG. 7) | Yes | None, only positive individual cells |
| 2. VEE TC-83 iDNA, Clone 13-1 (FIG. 6) | Yes | Yes |
| 3. VEE TC-83 iDNA, Clone 13-2 (FIG. 6) | Yes | Yes |
| 4. p3-10 DNA expressing TC-83 structural proteins only (control) | No | None, only positive individual cells |
| 5. Untransfected CHO cells (control) | No | No |

*DNA transfected into CHO cells is done in 6-well plates using Fugene 6 transfection reagent (Roche Applied Sciences)
**Observed on day 5 after transfection.
***IFA, immunofluorescence assay, by using antiserum for TC-83 structural proteins.

Example 4. Transfection of BHK-12 Cells with YF17D iDNA Vaccine

Briefly, plasmid DNA containing YF17D iDNA is transfected into cultured cells (CHO, BHK-21, or similar cell lines) and assayed using standard methods as described in Example 3. The results are shown in Table II. Plaque assay is used to determine the titer of live YF17D virus generated in cells transfected with plasmid iDNA. These results indicate that introduction of iDNA-based 17D vaccine into cultured cells results in synthesis of virus-specific RNA and in production of live YF17D virus (Table II).

TABLE II

Transfection of BHK-21 cells with plasmid DNA containing YF17D iDNA

| | iDNA Vaccine* | BHK Cell Mortality after DNA transfection in vitro** | YF17D titer, by plaque assay*** |
|---|---|---|---|
| 1. | YF17D iDNA | Yes | $10^8$ pfu/ml |
| 6. | Untransfected BHK-21 cells (control) | No | Not detected |

*DNA transfected into BHK cells is done in 6-well plates using Fugene 6 transfection reagent (Roche Applied Sciences)
**Observed on day 5 after transfection
***Assay performed on media collected from transfected cells 5 days post transfection.

Example 5. Infection of CHO Cells with TC-83 Virus Derived from iDNA-Transfected Cells In order to confirm that live TC-83 virus is generated in the cells transfected with plasmid DNA containing the complete TC-83 cDNA, the medium is harvested from transfected cells (see example 3) and used to infect fresh CHO cells. Fresh CHO cells are infected in 8-well chamber slides with 100-fold diluted media harvested from transfected cells, and expression of TC-83 antigens is detected by IFA at 24 hr postinfection (Table III). The results indicate that media from cells transfected with iDNA-based TC-83 vaccines contain live, infectious TC-83 virus.

TABLE III

Infection of fresh CHO cells with medium collected from CHO cells transfected with iDNA containing the full-length cDNA of TC-83 vaccine downstream from the CMV promoter*

| | DNA Vaccine Transfected | % cells positive for TC-83 Antigen, by IFA |
|---|---|---|
| 1. | VEE TC-83 modified iDNA, Clone 12 | 100 |
| 2. | VEE TC-83 iDNA, Clone 13-1 | 80 |
| 3. | VEE TC-83 iDNA, Clone 13-2 | 100 |
| 4. | p3-10 DNA expressing TC-83 structural proteins only (control) | 0 |
| 5. | Untransfected CHO cells (control) | 0 |

*Medium collected from transfected cells 5 days posttransfection (Table I) is diluted 100-fold, then 100 mcL are used to infect fresh CHO cells in 8-well chamber slides for 1 hr at 37° C., 5% $CO_2$. Then, 300 mcL of complete medium is added and incubation is continued for 24 hr.
**IFA 24 hr postinfection, by using antiserum for TC-83 structural proteins.

Example 6. Vaccination of Mice with TC-83 iDNA Vaccine

Experimental mice (BALB/c, C57BL/6, Swiss Webster outbred, or other susceptible strain) are injected intramuscularly, subcutaneously, and intradermally with a dose of each TC-83 iDNA vaccine (Clones 12, 13-1, 13-2, as indicated in Table I) ranging from 1 ng to 1 mg. The TC-83 iDNA vaccines are isolated from E. coli as plasmid DNA by using Promega Endo-free DNA isolation method. In 30 days, animals receive a second identical dose of the TC-83 iDNA vaccine. Serum samples from anesthetized animals are taken from the retroorbital sinus on days 0, 30, and 60. Immune response is determined by standard immunological methods including determination of serum antibody to TC-83 antigens in the serum of vaccinated animals by ELISA. Serum antibody to TC-83 antigens is detected suggesting successful vaccination with TC-83 iDNA vaccine.

Example 7. Vaccination of Mice with YF17D iDNA Vaccine

Experimental mice (BALB/c, C57BL/6, Swiss Webster outbred, or other susceptible strain) are injected intramuscularly, subcutaneously, and intradermally with a dose of each 17D iDNA vaccine (see DNA sequence on FIG. 7) ranging from 1 ng to 1 mg. The 17D iDNA vaccine is isolated from E. coli as plasmid DNA by using Promega Endo-free DNA isolation method. In 30 days, animals receive a second identical dose of the 17D iDNA vaccine. Serum samples from anesthetized animals are taken from the retroorbital sinus on days 0, 30, and 60. Immune response is determined by standard immunological methods including determination of serum antibody to YF 17D antigens in the serum of vaccinated animals by ELISA. Serum antibody to YF antigens is detected suggesting successful vaccination with YF17D iDNA vaccine.

Example 8. Optimization of Distance Between the 3' End of CMV Promoter and the 5' End of cDNA by Encapsidation Assay Using HA- or N-Vectors and the DNA c-Helpers For the successful function of the iDNA, it is important to achieve efficient transcription of the functional, full-length TC-83 RNA from the iDNA plasmid. Therefore, it is important to optimize transcription including the distance between the end of the promoter and the start of the cDNA, in order to maximize the efficacy of synthesis of functional RNA. We construct a "small iDNA" that encodes only the capsid gene of TC-83 virus including regulatory regions. All other TC-83 genes are deleted from such "capsid iDNA". Then, we insert synthetic oligonucleotides of varying lengths (see FIG. 13) between the CMV promoter and the "capsid iDNA" using SacI site at the 3' terminus of the CMV promoter. Thus, a series of "capsid iDNA" plasmids is made in which the distance between the promoter and the iDNA varies from 8 to 25 base pairs. Each capsid iDNA construct is transfected by electroporation into CHO cells along with (1) GP-helper RNA and (2) HA-vector RNA. The GP-helper RNA encodes the TC-83 glycoproteins, whereas HA-vector RNA encodes the HA gene of influenza. In the cotransfected CHO cells, the TC-83 capsid and GP proteins encapsidates the HA-vector into single-cycle particles. By titration of such particles using immunofluorescence assay (IFA) and HA antiserum, the titer of the particles is detected. In this system, the level of expression of capsid from the "capsid iDNA" is a rate-limiting factor and affects the titer of the particles.

We find that the optimal distance between the 3'-terminus of the CMV promoter and the 5' end of the TC-83 capsid cDNA is 15 base pairs between the SacI site (the end of CMV promoter) and the start of cDNA (FIG. 9). We find that this optimal distance provided expression of functional capsid antigen at a maximum level. However, other capsid iDNA constructs with distances of 12 to 18 bp also provide detectable level of expression and high titers of particles. The data are confirmed in several experiments using titration of HA-vector. We also confirm these optimization results when we use for quantitation the N-vector expressing nucleoprotein gene instead of HA gene.

Example 9. TC-83 Viruses Generated from Infectious Clones In Vitro are Avirulent in BALB/c Mice TC-83 viruses are generated by transfection of CHO cells with infectious TC-83 vaccine cDNA (iDNA), clones #12 and #13-1. Expression of TC-83 antigens is shown by IFA at 24 hr post transfection in cells transfected with either iDNA (#12 and #13-1). Viruses are harvested from CHO cell cultures at 96 hr post transfection, after and the cytopathic effect (CPE) is apparent. The titer of each virus is determined by standard plaque assay in Vero cell monolayers. The virus generated from iDNA #13-1 has the titer of 7×107 PFU/ml, whereas the virus generated from iDNA #12 does not show the plaques, suggesting slower formation of plaques and possibly, higher level of attenuation. Then, $10^5$ plaque forming units (PFU) of #13-1 virus are inoculated in BALB/c mice intramuscularly according to standard protocol. Virus generated from DNA #12 is not used for inoculation of animals, because the plaque titer cannot be determined. As a control, the wild type VEE virus (Trinidad strain) is inoculated into animals.

In the control VEE group, 10 out of 10 animals dies following inoculation, demonstrating the virulent nature of the control virus (FIG. 12). In contrast, virus generated from iDNA (#13-1) is avirulent in mice, as mice show no signs of disease. This result confirms that iDNA contains attenuated mutations derived from the TC-83 vaccine and that these attenuating mutations do not revert to the wild-type virulent phenotype during virus production from iDNA.

REFERENCES

Barnett E D. Yellow fever: epidemiology and prevention. Clin Infect Dis. 2007 Mar. 15; 44(6):850-6. Epub 2007 Feb. 1. Review, Bredenbeek P J, Molenkamp R, Spaan W J, Deubel V, Marianneau P, Salvato M S, Moshkoff D, Zapata J, Tikhonov I, Patterson J, Carrion R, Ticer A, Brasky K, Lukashevich I S. A recombinant Yellow Fever 17D vaccine expressing Lassa virus glycoproteins. Virology. 2006 Feb. 20; 345(2)199-304.

Kinney R M, Chang G J, Tsuchiya K R, Sneider J M, Roehrig J T, Woodward T M, Trent D W. Attenuation of Venezuelan equine encephalitis virus strain TC-83 is encoded by the 5'-noncoding region and the E2 envelope glycoprotein, J Virol. 1993; 67(3):1269-77.

Monath T P. Yellow fever: an update. Lancet Infect Dis. 2001 August; 1(1):11-20.

Monath T P. Dengue and yellow fever—challenges for the development and use of vaccines. N Engl J Med. 2007 Nov. 29; 357(22)2222-5.

Pugachev K V, Guirakhoo F, Monath T P. New developments in flavivirus vaccines with special attention to yellow fever. Curr Opin Infect Dis. 2005 October; 18(5): 387-94.

Pushko P, Parker M, Ludwig G V, Davis N L, Johnston R E, Smith N. Replicon-helper systems from attenuated Venezuelan equine encephalitis virus: expression of heterologous genes in vitro and immunization against heterologous pathogens in vivo. Virology 1997; 239(2):389-401.

Smithburn K C, Durieux C, Koerber R, et al. Yellow fever vaccination. Geneva, Switzerland: World Health Organization, 1956. WHO monograph series no. 30.

Tao D, Barba-Spaeth G, Rai U, Nussenzweig V, Rice C M, Nussenzweig R S. Yellow fever 17D as a vaccine vector for microbial CTL epitopes: protection in a rodent malaria model, J Exp Med. 2005 Jan. 17; 201(2):201-9.

The invention claimed is:

1. A vector comprising DNA encoding:
   (a) an infectious RNA molecule that encodes an alphavirus; and
   (b) a eukaryotic RNA polymerase promoter;
   wherein the DNA encoding the infectious RNA molecule is operably linked to the RNA polymerase promoter.

2. The vector of claim 1, wherein the infectious RNA molecule encodes a non-pathogenic alphavirus.

3. The vector of claim 1, wherein the RNA polymerase promoter is a cytomegalovirus (CMV) promoter.

4. The vector of claim 3, wherein the CMV promoter is located from about 12 to about 18 nucleic acid residues upstream of the 5' end of the DNA encoding the infectious RNA molecule.

5. The vector of claim 4, wherein the CMV promoter is located 15(±3) nucleic acid residues upstream of the 5' end of the DNA encoding the infectious RNA molecule.

6. The vector of claim 5, wherein the vector is a pASP5 vector.

7. The vector of claim 1, wherein the vector comprises a poly-A tail downstream of the DNA encoding the infectious RNA molecule.

8. The vector of claim 7, wherein the poly-A tail is located from about 0 to about 500 nucleic acid residues downstream of the 3' end of the DNA encoding the infectious RNA molecule.

9. A vaccine comprising a therapeutically effective amount of the vector of claim 2.

10. The vaccine of claim 9, further comprising a pharmaceutically acceptable carrier.

11. A method of preparing a clonally pure live attenuated alphavirus, wherein the method comprises transfecting the vector of claim 2 into a eukaryotic cell and isolating at least one clonally pure infectious alphavirus from a culture medium comprising the transfected eukaryotic cell, thereby obtaining at least one clonally pure live attenuated alphavirus.

12. A method for immunizing a mammal against an alphavirus, wherein the method comprises the step of administering to the mammal the vaccine of claim 10.

13. The method of claim 12, wherein the mammal is a human or a horse.

14. The method of claim 13, wherein the mammal is a human.

15. A method of preparing a vaccine for immunizing a mammal against an alphavirus, wherein the method comprises transfecting the vector of claim 2 into a eukaryotic cell and isolating at least one clonally pure infectious alphavirus from a culture medium comprising the transfected eukaryotic cell, thereby obtaining a vaccine.

16. A vector comprising a DNA encoding:
   (a) an infectious RNA molecule that encodes a Venezuelan Equine Encephalitis (VEE) virus; and
   (b) a CMV promoter located 15(±3) nucleic acid residues upstream of the 5' end of the DNA encoding the infectious RNA molecule;
   wherein the DNA encoding the infectious RNA molecule is operably linked to the CMV promoter.

17. The vector of claim 16, wherein the vector is a pASP5 vector.

18. The vector of claim 16, wherein the vector comprises a poly-A tail downstream of the DNA encoding the infectious RNA molecule.

19. The vector of claim 17, wherein the vector comprises a poly-A tail downstream of the DNA encoding the infectious RNA molecule.

20. A vaccine comprising a therapeutically effective amount of the vector of claim 16; and wherein the encoded VEE virus is non-pathogenic.

21. A vaccine comprising a therapeutically effective amount of the vector of claim 17; and wherein the encoded VEE virus is non-pathogenic.

22. A method of preparing a clonally pure live attenuated VEE virus, wherein the method comprises transfecting the vector of claim 16 into a eukaryotic cell and isolating a clonally pure infectious virus from a culture medium comprising the transfected eukaryotic cell, thereby obtaining clonally pure live attenuated VEE virus.

23. A method of preparing clonally pure live attenuated VEE virus, wherein the method comprises transfecting the vector of claim 17 into a eukaryotic cell and isolating clonally a pure infectious virus from a culture medium comprising the transfected eukaryotic cell, thereby obtaining a clonally pure live attenuated VEE virus.

24. A method of preparing a vaccine for immunizing a mammal against a VEE virus, wherein the method comprises transfecting the vector of claim 16 into a eukaryotic cell and isolating clonally pure infectious virus from a culture medium comprising the transfected eukaryotic cell, thereby obtaining a vaccine; and wherein the encoded VEE virus is non-pathogenic.

25. A method of preparing a vaccine for immunizing a mammal against a VEE virus, wherein the method comprises transfecting the vector of claim 17 into a eukaryotic cell and isolating clonally pure infectious viruses from a culture medium comprising the transfected eukaryotic cell, thereby obtaining a vaccine; and wherein the encoded VEE virus is non-pathogenic.

26. A vector comprising a DNA encoding:
   (a) an infectious RNA molecule that encodes a Yellow Fever virus; and
   (b) a CMV promoter located from 15(±3) nucleic acid residues upstream of the 5' end of the DNA encoding the infectious RNA molecule;
   wherein the DNA encoding the infectious RNA molecule is operably linked to the CMV promoter.

27. A human vaccine comprising a therapeutically effective amount of the a DNA vector encoding:
   (a) an infectious RNA molecule that encodes a nonpathogenic alphavirus or a nonpathogenic flavivirus; and
   (b) a CMV promoter located from 15(±3) nucleic acid residues upstream of the 5' end of the DNA encoding the infectious RNA molecule;
   wherein the DNA encoding the infectious RNA molecule is operably linked to the CMV promoter, and the vaccine is pharmaceutically acceptable for a human.

28. A human vaccine comprising an effective amount of a DNA vector encoding:
   (a) an infectious RNA molecule that encodes a nonpathogenic flavivirus; and
   (b) a CMV promoter located from 15(±3) nucleic acid residues upstream of the 5' end of the DNA encoding the infectious RNA molecule;
   wherein the DNA encoding the infectious RNA molecule is operably linked to the CMV promoter, and the vaccine is pharmaceutically acceptable for a human.

29. The vector of claim 26, wherein the infectious RNA molecule encodes a non-pathogenic Yellow Fever virus.

30. A vaccine comprising an effective amount of the vector of claim 29.

31. A vector comprising a DNA encoding:
   (a) an infectious RNA molecule, wherein
      (i) the RNA molecule encodes a non-pathogenic alphavirus; and
      (ii) the RNA molecule comprises a first 26S promoter and a second 26S promoter; and
   (b) a CMV promoter located from about 12 to about 18 nucleic acid residues upstream of the 5' end of the DNA encoding the infectious RNA molecule.

32. The vector of claim 31, wherein the first 26S promoter is located upstream from a gene encoding a capsid protein and the second 26S promoter is located upstream from one or more genes encoding one or more glycoproteins.

* * * * *

UNITED STATES PATENT AND TRADEMARK OFFICE
CERTIFICATE OF CORRECTION

PATENT NO. : 9,968,672 B2
APPLICATION NO. : 14/168788
DATED : May 15, 2018
INVENTOR(S) : Peter Pushko et al.

Page 1 of 1

It is certified that error appears in the above-identified patent and that said Letters Patent is hereby corrected as shown below:

In the Claims

Column 50, Line 21, please replace "268" with —26S—.

Signed and Sealed this
Twenty-fourth Day of December, 2019

Andrei Iancu
*Director of the United States Patent and Trademark Office*